US009328356B2

(12) United States Patent
Bowen et al.

(10) Patent No.: US 9,328,356 B2
(45) Date of Patent: May 3, 2016

(54) PESTICIDAL NUCLEIC ACIDS AND PROTEINS AND USES THEREOF

(75) Inventors: David J. Bowen, Glencoe, MO (US); Gregory J. Bunkers, Wildwood, MO (US); Catherine Chay, Ballwin, MO (US); John W. Pitkin, Wildwood, MO (US); Timothy J. Rydel, St. Charles, MO (US); Eric J. Sturman, Wildwood, MO (US); Uma R. Sukuru, Chesterfield, MO (US); Brook Van Scoyoc, St. Louis, MO (US); Stanislaw Flasinski, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 739 days.

(21) Appl. No.: 13/369,723

(22) Filed: Feb. 9, 2012

(65) Prior Publication Data

US 2012/0278954 A1 Nov. 1, 2012

Related U.S. Application Data

(60) Provisional application No. 61/441,709, filed on Feb. 11, 2011, provisional application No. 61/441,697, filed on Feb. 11, 2011.

(51) Int. Cl.

| | |
|---|---|
| ***C12N 15/82*** | (2006.01) |
| ***C07K 14/325*** | (2006.01) |
| ***A01N 63/02*** | (2006.01) |

(52) U.S. Cl.

CPC ............ *C12N 15/8285* (2013.01); *A01N 63/02* (2013.01); *C07K 14/325* (2013.01); *C12N 15/8286* (2013.01)

(58) Field of Classification Search

None

See application file for complete search history.

(56) References Cited

U.S. PATENT DOCUMENTS

| | | | | |
|---|---|---|---|---|
| 5,770,431 | A * | 6/1998 | Liu et al. | 435/252.3 |
| 6,028,246 | A * | 2/2000 | Lambert et al. | 800/279 |
| 6,063,756 | A | 5/2000 | Donovan et al. | |
| 2003/0049243 | A1 | 3/2003 | Liu et al. | |
| 2003/0144192 | A1 | 7/2003 | Donovan et al. | |
| 2006/0191034 | A1 | 8/2006 | Baum et al. | |

FOREIGN PATENT DOCUMENTS

WO 9408010 A1 4/1994

OTHER PUBLICATIONS

Argôlo-Filho et al, 2014, Insects 5:62-91.*

Guo et al (2004, Proc. Natl. Acad. Sci. USA 101: 9205-9210).*

Böckenhoff et al.," Studies on the Nutrient Uptake by the Beet Cyst Nematode Heterodera schachtii by in situ Microinjection of Fluorescent Probes into the Feeding Structures in Arabidopsis thaliana", Parasitology, 1994, pp. 249-255, vol. 109, No. 2.

Urwin et al., "Resistance to Both Cyst and Root-Knot Nematodes Conferred by Transgenic Arabidopsis Expressing a Modified Plant Cystatin", The Plant Journal, 1997, pp. 455-461, vol. 12, No. 2.

* cited by examiner

*Primary Examiner* — Anne Kubelik

(74) *Attorney, Agent, or Firm* — Thompson Coburn LLP; J. Wendy Davis

(57) ABSTRACT

The invention provides compositions comprising polynucleotide molecules encoding certain pesticidal polypeptides which exhibit plant parasitic nematode and/or insect control properties, and are particularly directed to controlling plant parasitic pest species of nematodes and insects known to infest crop plant species. Methods for controlling pests are disclosed in which the toxic proteins are provided in the diet of the targeted plant pests. The invention also provides compositions such as nucleic acids, proteins, and plant and bacterial cells, plants, and seeds containing the nucleic acid and protein compositions, as well as methods and kits for identifying, detecting, and isolating the compositions of the present invention. The invention further provides a method of producing crops from recombinant seeds which contain the polynucleotide molecules encoding the pesticidal polypeptides of the present invention.

15 Claims, No Drawings

PESTICIDAL NUCLEIC ACIDS AND PROTEINS AND USES THEREOF

CROSS REFERENCE TO RELATED APPLICATIONS

This application claims priority to U.S. Provisional Application Ser. No. 61/441,697 and U.S. Provisional Application Ser. No. 61/441,709, both filed Feb. 11, 2011, which are incorporated herein by reference.

INCORPORATION OF SEQUENCE LISTING

The Sequence Listing accompanying this application is contained within the computer readable file "38-21(57560) SEQUENCE LISTING_ST25.txt" submitted electronically and contemporaneously with the filing of this application through the USPTO EFS-Web. The file is 105 kilobytes (measured in MS-Windows), was created on 19 Jan. 2012, and is incorporated herein by reference.

FIELD OF THE INVENTION

The invention relates to novel polynucleotide and protein compositions that, when expressed and or produced in plants, impart resistance to plant pathogenic nematodes and insect infestation. The polynucleotides and proteins can be expressed in plant and bacterial cells, and the plant cells can be regenerated into transgenic (recombinant) plants, plant tissues, plant parts, and seeds. Compositions derived from such plants, plant materials, and seed that contain detectable amounts of such polynucleotides and proteins are included within the scope of the invention. The invention also relates to compositions and methods for controlling plant pathogenic nematodes and insect pests of crop plants.

BACKGROUND OF THE INVENTION

The increasing human population will require higher yields of food, feed, and fiber from crop plants on decreasing amounts of arable land. Several types of insects and nematodes are known to reduce yield of crops produced from plants. Plant pests damage plant parts, including roots, developing flower buds, flowers, leaves, stems, and seeds, which leads to lower yields.

Traditional approaches for controlling plant pests have used chemical control agents and construction of inter-specific hybrids between crops and their wild-type relatives as sources of resistant germplasm. Chemical pest control agents, although effective, have several disadvantages. Many chemical control agents are expensive to manufacture, and are characterized as pollutants because they persist in the environment as a result of their resistance to microbial degradation. Chemical control agents require on-farm formulation, which increases the safety risk to the farmer due to the exposure to chemical agent formulations. The chemical agent formulations have to be applied at least once and often, more than once per growing season, increasing the carbon footprint related to these compositions. Methods and compositions employing plant biotechnology pest control agents are also effective means for controlling plant pests, for instance through plant expression of one or more pest control agents that are generally selectively toxic to a particular target pest when ingested by the pest. Unlike chemical agents, biotech approaches have been demonstrated to be environmentally friendly, have no known safety risks when used by farmers, and are economical in terms of carbon footprint impact and ease of use for deployment by the farmer. However, there are only a few examples of such biotech compositions and methods for controlling such pests, and even fewer if any examples of any biotechnology approaches that have demonstrated efficacy in controlling plant pathogenic nematodes. Thus, there is a need for new compositions and methods for protecting plants from such pest infestation, generally for the purpose of maintaining and enhancing yields of crops produced from such plants, and for sustaining and providing food, feed and fiber for the increasing human population.

SUMMARY OF THE INVENTION

Polynucleotide molecules are provided encoding exemplary pesticidal polypeptides as set forth in SEQ ID NO:2, SEQ ID NO:6, SEQ ID NO:10, SEQ ID NO:14, SEQ ID NO:18, SEQ ID NO:22, SEQ ID NO:26, SEQ ID NO:30, SEQ ID NO:34, SEQ ID NO:38, SEQ ID NO:42, SEQ ID NO:46, SEQ ID NO:50, SEQ ID NO:54, SEQ ID NO:58, and SEQ ID NO:60. Polypeptides having an amino acid sequence exhibiting from at least about 45% to about 99.9% identity to the pesticidal protein (polypeptide) sequences as set forth in any of the foregoing protein sequences (any percentage in between 45 and 99.9) and exhibiting substantially equivalent (biologically functional equivalent) pesticidal activity as any one of these sequences are specifically contemplated. Fragments of these polypeptide sequences that exhibit the requisite pesticidal activity are intended to be within the scope of the present invention. Such polynucleotides may be extracted and/or obtained directly from a host cell or made artificially through various means of synthesis, and in either case, are considered to be recombinant polynucleotides.

Polynucleotides containing one or more nucleotide sequence segments encoding the pesticidal proteins of the present invention are provided, which may be operably linked to a heterologous promoter that initiates expression of the sequence region in a designated host cell, resulting in the production or manufacture of the pesticidal protein in the host cell. The promoter may include a plant-expressible promoter, a promoter that functions in one or more species of bacteria, and a yeast functional promoter, or combinations thereof. The plant-expressible promoter may include any number of promoters known in the art, including but not limited to corn sucrose synthetase 1 promoter, corn alcohol dehydrogenase 1 promoter, corn light harvesting complex promoter, corn heat shock protein promoter, pea small subunit RuBP carboxylase promoter, Ti plasmid mannopine synthase promoter, Ti plasmid nopaline synthase promoter, petunia chalcone isomerase promoter, bean glycine rich protein 1 promoter, Potato patatin promoter, lectin promoter, CaMV 35S promoter, FMV promoter, ubiquitin promoters promoter, and the S E9 small subunit RuBP carboxylase promoter.

Isolated polynucleotide segments are provided for use as probes and/or primers, which may be from about 20 to about 1000 contiguous nucleotides in length or any length in between twenty and one thousand contiguous nucleotides, and exhibit at least about 90% identity to the same contiguous length of nucleotides as set forth in any of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, and SEQ ID NO:63, or the complement of any of the foregoing polynucleotide sequences.

In another aspect of the invention, polynucleotides encoding any of the pesticidal polypeptides set forth above are provided in recombinant expression cassettes. The expression cassettes can be provided in vectors for use in replicating, maintaining and transferring the nucleic acid component encoding the pesticidal proteins of the present invention. The vectors of the present invention contain at least a sequence region that encodes the polypeptide as set forth above. The vector includes a plasmid, baculovirus, artificial chromosome, virion, cosmid, phagemid, phage, or viral vector.

Host cells may be any appropriate transgenic host cell including but not limited to microbial cells (microorganisms) such as an *Agrobacterium*, a *Bacillus*, an *Escherichia*, a *Salmonella*, a *Pseudomonas*, a *Rhizobium* bacterial cell, a yeast cell such as a *pichia* yeast or *saccharomyces* species yeast cell, or a plant cell. Vectors as described above can be provided in a transgenic microbial host cell. The transgenic microbial host cell includes a prokaryotic or eukaryotic host cell. The transgenic prokaryotic host cell is a bacterial cell and the transgenic eukaryotic host cell is a plant or a fungal/yeast cell. The transgenic bacterial cell includes a recombinant bacterium including a *Bacillus thuringiensis, Bacillus subtilis, Bacillus megaterium, Bacillus cereus, Bacillus laterosperous, Escherichia, Salmonella, Agrobacterium, Rhizobium*, or *Pseudomonas* cell. The transgenic plant host cell includes a monocotyledonous or dicotyledonous plant cell and may include any plant cell from the Group of Plants or Plant Group set forth below. To the extent that a microbial cell is a plant cell, the cell can be obtained from any plant, plant tissue, plant part or seed from a plant selected from the group consisting of any of the following, including but not limited to barley, bean, broccoli, cabbage, canola (rapeseed), carrot, cassava, castor, cauliflower, celery, chickpea, Chinese cabbage, coffee, corn (including sweet corn), clover, cotton, a cucurbit, cucumber, deciduous trees (including but not limited to banana, citrus, eucalyptus, nut trees (including but not limited to hickory, pecan, and walnut trees), oak trees (including but not limited to live oak, pin oak, and post oak trees), olive, palm (including coconut palm), poplar, sweet gum, and rootstocks of all of the preceding trees), eggplant, evergreen trees (including but not limited to Douglas fir), flax, garlic, grape, grasses (including but not limited to alfalfa, pasture grass, switchgrass, and turf grass), hops, leek, lettuce, millets, melons (including but not limited to cantaloupe, honeydew melon, and watermelon), oat, onion, pea, peanut, pepper, pigeonpea, pine (including Loblolly pine, Radiata pine, and Southern pine), potato, pumpkin, radish, rice, rye, safflower, shrub, sorghum, soybean, spinach, squash, strawberry, sugar beet, sugarcane, sunflower, sweet corn, sweet potato, tea, tobacco, tomato, triticale, or wheat. The aforementioned are referenced herein as the "Group of Plants" or the "Plant Group".

Recombinant plants, plant tissue, plant parts, or seed contain the polynucleotides of the present invention and express the proteins of the present invention from such polynucleotides. The plant part is a leaf, a stem a flower, a sepal, a fruit, a root, or a seed. Products produced from a recombinant plant of the present invention are also contemplated, and can include at least any of the following: oil, meal, lint and seed of the recombinant plant. The polynucleotides and proteins of the present invention are present in a detectable amount in the plants and plant products, and are useful at least as markers for tracking the presence of seeds and plant tissues containing the polynucleotide and proteins through trade and commerce, in fields of crops, and in various embodiments referenced herein.

There is provided a method of detecting and/or isolating in or from a biological sample, a polynucleotide molecule encoding a pesticidal polypeptide of the present invention in which the steps of the method include (i) selecting a pair of oligonucleotide primers that produce an amplicon encoding all or a representative amount of the pesticidal polypeptide of the present invention when used together in an amplification reaction with the biological sample containing the polynucleotide; (ii) producing the amplicon from the polynucleotide; (iii) detecting and/or isolating the amplicon; and (iv) generating nucleotide sequence information corresponding to the amplicon to identify and confirm the presence (or absence) of a segment of a polynucleotide molecule encoding all or a representative amount of the pesticidal polypeptide. Alternatively, the detecting and/or isolating step can be conducted by providing a polynucleotide probe derived from a sufficient length of DNA or RNA encoding the pesticidal polypeptide that hybridizes under specific or under stringent hybridization conditions to such a polynucleotide encoding a pesticidal polypeptide of the present invention.

Methods of controlling or killing a target lepidopteran pest, coleopteran pest, or plant pathogenic nematode pest population are provided and include contacting the pest population with a pesticidally-effective amount of the polypeptide as set forth above. The "lepidopteran pest population" includes *Spodoptera frugiperda, Spodoptera exigua*), *Mamestra configurata, Agrotis ipsilon, Trichoplusia ni, Pseudoplusia includens, Anticarsia gemmatalis, Hypena scabra, Heliothis virescens, Agrotis subterranea, Pseudaletia unipuncta, Agrotis orthogonia, Ostrinia nubilalis, Amyelois transitella Crambus caliginosellus, Herpetogramma licarsisalis, Homoeosoma electellum, Elasmopalpus lignosellu, Cydia pomonella, Endopiza viteana, Grapholita molesta, Suleima helianthana, Plutella xylostella, Pectinophora gossypiella, Lymantria dispar, Blatta orientalis, Blatella asahinai, Blattella germanica, Supella longipalpa, Periplaneta americana, Periplaneta brunnea, Leucophaea maderae, Alabama argillacea, Archips argyrospila, A. rosana, Chilo suppressalis, Cnaphalocrocis medinalis, Crambus caliginosellus, C. teterrellus, Diatraea grandiosella, D. saccharalis, Earias insulana, E. vittella, Helicoverpa armigera, H. zea, Heliothis virescens, Herpetogramma licarsisalis, Lobesia botrana, Pectinophora gossypiella, Phyllocnistis citrella, Pieris brassicae, P. rapae, Plutella xylostella, Spodoptera exigua, S. litura, S. frugiperda, Tuta absoluta*. The "coleopteran pest population" includes *Anthonomus grandis, Lissorhoptrus oryzophilu, Sitophilus granaries, Sitophilus oryzae, Hypera punctata, Sphenophorus maidis, Leptinotarsa decemlineata, Diabrotica virgifera virgifera, Diabrotica barberi, Diabrotica undecimpunctata howardi, Chaetocnema pulicaria, Phyllotreta cruciferae, Colaspis brunnea, Oulema melanopus, Zygogramma exclamationis, Epilachna varivestis, Popillia japonica, Cyclocephala boreali, Cyclocephala immaculata, Rhizotrogus majalis, Phyllophaga crinita, Ligyrus gibbosus, Melanotus* spp., *Conoderus* spp., *Limonius* spp., *Agriotes* spp., *Ctenicera* spp., *Aeolus* spp., *Eleodes* spp. The "plant pathogenic nematode population" includes *Heterodera glycines* (soybean cyst nematode), *Heterodera schachtii* (beet cyst nematode), *Heterodera avenae, Globodera rostochiensis, Globodera pailida, Pratylenchus zeae* (a root knot nematode), *Meloidogyne javanica, Pratylenchus brachyurus* (a root knot nematode), *Meloidogyne hapla, Meloidogyne incognita.*

An alternative method for controlling such plant pest infection includes providing a pest inhibitory amount of a pesticidal polypeptide of the present invention to a pest susceptible to the polypeptide, thereby controlling the pest. The pest is an insect or a nematode. The insect may be any insect within the taxonomical orders including Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, or Trichoptera (hereinafter, the "Insect Orders"). The nematode may be from any genus of nematodes referred to as *Acontylus, Anguina, Aorolaimus, Aphasmatylenchus, Aphelenchoides, Aphelenchus, Atalodera, Atylenchus, Bakernema, Belonolaimus, Brachydorus, Bursaphelenchus, Cacopaurus, Caloosia, Carphodorus, Criconema, Criconemella, Cryphodera, Ditylenchus, Dolichodorus, Eutylenchus, Globodera, Gracilacus, Helicotylenchus, Hemicriconemoides, Hemicycliophora, Heterodera, Hirschmanniella, Histotylenchus, Hoplolaimus, Hoplotylus, Longidorus, Macrotrophurus, Meloidodera, Meloidogyne, Merlinius, Morulaimus, Nacobbus, Nothanguina, Nothotylenchus, Paralongidorus, Paratrichodorus, Paratrophurus, Paratylenchus, Peltamigratus, Pratylenchoides, Pratylenchus, Psilenchus, Radopholoides, Radopholus, Rhadinaphelenchus, Rototylenchus, Rotylenchoides, Rotylenchus, Sarisodera, Scutellonema, Sphaeronema, Subanguina, Telotylenchoides, Telotylenchus, Trichotylenchus, Trophonema, Trophotylenculus, Trophurus, Tylenchorhynchus, Tylenchulus, Tylenchus, Tylodorus, Xiphinema*, or *Zygotylenchus* (hereinafter, the "Nematode Species"). In related embodiments, the nematode species includes cyst and related nematodes such as *Heterodera glycines* (soybean cyst nematode), *Heterodera schachtii* (beet cyst nematode), *Heterodera avenae* (cereal cyst nematode), and *Globodera rostochiensis* and *Globodera pailida* (potato cyst nematodes), *Pratylenchus zeae, Meloidogyne javanica, Pratylenchus brachyurus, Meloidogyne hapla*, or *Meloidogyne incognita* (hereinafter, the "Cyst Nematode" group). The pest inhibitory amount of the pesticidal polypeptide is provided in the diet of the pest, and the diet of the pest can be a part of a recombinant plant, seed of such plant, or product of the plant. The pest inhibitory amount of the polypeptide may also be provided in a topical formulation to a plant. Such formulation could include a preparation containing bacterial cells, bacterial spores, and parasporal crystals which contain or are producing one or more of the polypeptides/toxic agents of the present invention in a sufficient amount to inhibit the pest infestation of the plant to which the formulation is applied. A formulation for controlling nematode or insect species within the scope of the present invention may consist of recombinant bacterial cells and/or spores which may be producing the toxic proteins of the present invention, or parasporal crystals that contain pesticidal amounts of the polypeptide. The bacterial cells, spores, or parasporal crystals are typically from *Bacillus* species. Antibodies are contemplated that specifically bind to a polypeptide having the amino acid sequence as set forth in any of SEQ ID NO:2, SEQ ID NO:6, SEQ ID NO:10, SEQ ID NO:14, SEQ ID NO:18, SEQ ID NO:22, SEQ ID NO:26, SEQ ID NO:30, SEQ ID NO:34, SEQ ID NO:38, SEQ ID NO:42, SEQ ID NO:46, SEQ ID NO:50, SEQ ID NO:54, SEQ ID NO:58, and/or SEQ ID NO:60, or a peptide, or an epitope derived therefrom. Particularly, purified antibodies that specifically bind to one or more of the polypeptides of the present invention, or to a peptide or epitope derived from the proteins of the present invention are contemplated.

Such antibodies are useful at least in methods of detecting pesticidal polypeptides such as those set forth in SEQ ID NO:2, SEQ ID NO:6, SEQ ID NO:10, SEQ ID NO:14, SEQ ID NO:18, SEQ ID NO:22, SEQ ID NO:26, SEQ ID NO:30, SEQ ID NO:34, SEQ ID NO:38, SEQ ID NO:42, SEQ ID NO:46, SEQ ID NO:50, SEQ ID NO:54, SEQ ID NO:58, and/or SEQ ID NO:60 in a biological sample. A method of detecting such proteins could include the steps of contacting the biological sample with an antibody that specifically binds to one or more of the proteins of the present invention, and detecting the binding of the antibody to the pesticidal polypeptide. Alternatively, proteins of the present invention, or proteins that are substantially related to the proteins of the present invention can be detected in or isolated from a biological sample either by directly identifying the protein in the sample using for example, antibodies as indicated above, or by screening for the presence of a polynucleotide encoding the pesticidal protein. Detecting the polynucleotide encoding such protein could include the steps of: i) selecting a pair of primers that produce an amplicon encoding the pesticidal protein when used together in an amplification reaction with the polynucleotide; ii) producing the amplicon by using the polynucleotide as a template in the amplification reaction; iii) detecting/isolating the amplicon; iv) generating DNA sequence information corresponding to the amplicon to confirm that the amplicon encodes the pesticidal protein; and v) testing the pesticidal protein to confirm pesticidal activity. Alternatively, a method for detecting the protein of the present invention, or a related pesticidal protein such as a δ-endotoxin polypeptide, in a biological sample could include the steps of: i) obtaining a biological sample suspected of containing a δ-endotoxin polypeptide; ii) contacting the sample with an antibody that specifically binds to the polypeptide under conditions effective to allow the formation of immune complexes; and iii) detecting the immune complexes so formed. Another alternative method for detecting a target pesticidal polypeptide of the present invention in a sample may include the steps of: i) contacting the sample with an antibody that specifically binds the target pesticidal polypeptide; ii) detecting the binding of the antibody to the target in the sample; and iii) identifying the target as a pesticidal polypeptide exhibiting at least 90% amino acid sequence identity to any one of the proteins set forth in SEQ ID NO:2, SEQ ID NO:6, SEQ ID NO:10, SEQ ID NO:14, SEQ ID NO:18, SEQ ID NO:22, SEQ ID NO:26, SEQ ID NO:30, SEQ ID NO:34, SEQ ID NO:38, SEQ ID NO:42, SEQ ID NO:46, SEQ ID NO:50, SEQ ID NO:54, SEQ ID NO:58, and/or SEQ ID NO:60.

Detection methods can be conducted using reagents and instructions packaged together in kit form and are useful for detecting the proteins and polynucleotides of the present invention. Such kits could include a first reagent or antibody that binds specifically to the polypeptide, or specifically to a peptide or an epitope derived therefrom; and a second reagent such as a control polypeptide corresponding to any of the proteins as set forth in any of SEQ ID NO:2, SEQ ID NO:6, SEQ ID NO:10, SEQ ID NO:14, SEQ ID NO:18, SEQ ID NO:22, SEQ ID NO:26, SEQ ID NO:30, SEQ ID NO:34, SEQ ID NO:38, SEQ ID NO:42, SEQ ID NO:46, SEQ ID NO:50, SEQ ID NO:54, SEQ ID NO:58, and/or SEQ ID NO:60, or a peptide, or an epitope derived therefrom.

In another aspect of the present invention, there is provided a method of preparing insect resistant plants. Such plants can be prepared by contacting a recipient plant cell with a transgene that encodes one or more of the polypeptides of the present invention under conditions permitting the uptake of the transgene by the cell, and selecting a recipient cell in which the transgene has been incorporated into the cell genome, and regenerating a plant from the selected recipient cell. The regenerated plant is confirmed to be a fertile transgenic plant exhibiting pest resistance, and the pest resistance includes resistance to plant pathogenic nematode infestation and one other pest resistance selected from resistance against to a coleopteran insect or to a lepidopteran insect. The contacting step includes any one or ore of the methods known in the art, including microprojectile bombardment, electroporation or *Agrobacterium*-mediated plant cell transformation. The regenerated plant is resistant to at least one of the members of the plant parasitic nematode group including *Heterodera* species, *Globodera* species, *Meloidogyne* species, *Rotylenchulus* species, *Hoplolaimus* species, *Belonolaimus* species, *Pratylenchus* species, *Longidorus* species, *Paratrichodorus* species, *Ditylenchus* species, *Xiphinema* species, *Dolichodorus* species, *Helicotylenchus* species, *Radopholus* species, *Hirschmanniella* species, *Tylenchorhynchus* species, or *Trichodorus* species.

Transgenic seed containing one or more polynucleotide segments encoding one or more of the proteins of the present invention may be produced comprising the steps of: transforming a plant with a transgene that encodes the polypeptide as set forth above, the transgene operably linked to a promoter that expresses the transgene in a plant, thereby obtaining a fertile transgenic plant comprising the transgene; and growing the plant under appropriate conditions to produce the transgenic seed.

Progeny of any generation of a pest resistance-enhanced fertile transgenic plant can be produced from such transgenic plants and seeds of the foregoing plants and seed, wherein the progeny contain the polynucleotide and encode the protein(s) of the present invention, and has enhanced pest resistance against a coleopteran insect, lepidopteran insect, or a plant pathogenic nematode relative to the corresponding non-transgenic plant.

Pest resistant plants can be produced by following the method of: (a) crossing a pest resistant plant comprising a transgene that encodes the polypeptide as set forth above with another plant; (b) obtaining at least one progeny plant derived from the cross of (a); and (c) selecting progeny that comprises the transgene, wherein the progeny is resistant against a coleopteran insect, lepidopteran insect, or a plant pathogenic nematode.

Seed can be produced from the plants of the present invention. Seed containing a polynucleotide molecule encoding one or more of the proteins of the present invention, whether homozygous or heterozygous for the particular transgenic allele, can be packaged for planting in a field, and a crop can be produced from the planted seed. The crop from such plants can be harvested, and if seed of the harvested generation are the crop (such as soybean, rice, wheat, canola or corn and the like), at least 50% of the harvested crop are seed containing the polynucleotide molecule.

Commodity products (or biological samples) containing a plant or plant part as set forth above that can be shown to contain a detectable amount of a polypeptide having the amino acid sequence of any of the proteins of the present invention, or polynucleotides encoding any such protein. The detection of the polypeptide or the polynucleotide in the commodity (or biological sample) is determinative of the presence of the plant or plant part in the commodity (or biological sample), and all such commodity products in which the polypeptide is detectable to a level of at least about (i) one part per million, (ii) or one nanogram per gram fresh weight of tissue, are within the scope of the present invention. A plant cell of the present invention may be regenerated into a recombinant plant which can produce a plant part containing any of the proteins of the present invention. The plant part includes a leaf, a stem a flower, a sepal, a fruit, a root, or a seed. Products produced from a recombinant plant or plant part contain a detectable amount of any one of the proteins of the present invention, or polynucleotide segments encoding such proteins. Such products include oil, meal, lint and seed of such recombinant plants. The detectable amount of the proteins and/or polynucleotides are useful as molecular markers for tracking and/or identifying the presence of seeds and plant tissues of the present invention as these are moved through commerce.

The proteins of the present invention originate from *Bacillus thuringiensis* species of bacteria, and as such, are likely to be characterized as delta-endotoxins, and are typically produced from a recombinant polynucleotide. Such delta endotoxin proteins will have an amino acid sequence that exhibits at least from about 45%, 50%, 55%, 60%, 65%, 70%, 75%, 80%, 85%, 90%, 95%, 99%, 99.9%, or 100% amino acid sequence identity to the amino acid sequence as set forth in any of the sequences shown in SEQ ID NO:2, SEQ ID NO:6, SEQ ID NO:10, SEQ ID NO:14, SEQ ID NO:18, SEQ ID NO:22, SEQ ID NO:26, SEQ ID NO:30, SEQ ID NO:34, SEQ ID NO:38, SEQ ID NO:42, SEQ ID NO:46, SEQ ID NO:50, SEQ ID NO:54, SEQ ID NO:58, and SEQ ID NO:60. Each such protein will preferably include at least 50, or from about 50 to about 100, or from about 50 to about 300 contiguous amino acids present in any full length protein sequence set forth in the sequences referenced above, and the toxin proteins are preferably encoded by a polynucleotide segment that hybridizes under stringent conditions to the polynucleotide coding sequences as set forth in any of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, and SEQ ID NO:63.

Compositions containing the proteins of the present invention are provided in an agriculturally-acceptable carrier. The composition may contain a recombinant *Bacillus thuringiensis* cell extract, cell suspension, cell homogenate, cell lysate, cell supernatant, cell filtrate, or cell pellet in which at least a pest inhibitory amount of one or more of the proteins of the present invention are provided, and the composition can be provided in the form of a powder, dust, pellet, granule, spray, emulsion, colloid, or solution. The composition may be prepared by desiccation, lyophilization, homogenization, extraction, filtration, centrifugation, sedimentation, or concentration of a culture of recombinant *Bacillus thuringiensis* cells or spore crystals containing one or more of the proteins of the present invention. The pesticidal composition preferably contains from about 1% to about 99% by weight of one or more of the pesticidal proteins described herein.

The proteins of the present invention can be obtained in substantially concentrated and/or purified form by a process which may include the steps of i) culturing recombinant *Bacillus thuringiensis* cells containing one or more recombinant polynucleotide as set forth above under conditions effective to produce the pesticidal protein, and obtaining the pesticidal polypeptide so produced. The polypeptide will preferably contain the contiguous amino acid sequence as set forth in any of SEQ ID NO:2, SEQ ID NO:6, SEQ ID NO:10, SEQ ID NO:14, SEQ ID NO:18, SEQ ID NO:22, SEQ ID NO:26, SEQ ID NO:30, SEQ ID NO:34, SEQ ID NO:38, SEQ ID NO:42, SEQ ID NO:46, SEQ ID NO:50, SEQ ID NO:54, SEQ ID NO:58, and SEQ ID NO:60.

BRIEF DESCRIPTION OF THE SEQUENCES

SEQ ID NO 1 represents a native Bt nucleotide sequence encoding a ET34 protein.

SEQ ID NO 2 represents an amino acid sequence translation of SEQ ID NO 1.

SEQ ID NO 3 represents an artificial sequence encoding a ET34 protein.

SEQ ID NO 4 represents an amino acid sequence translation of SEQ ID NO 3 from nucleotide position 1 through nucleotide position 378.

SEQ ID NO 5 represents a nucleotide sequence encoding a P139 secretion signal peptide (nucleotide position 1-75) fused in frame to a native Bt nucleotide sequence encoding a ET34 protein (nucleotide position 76-450).

SEQ ID NO 6 represents the amino acid sequence translation of SEQ ID NO 5.

SEQ ID NO 7 represents a nucleotide sequence encoding a P139 secretion signal peptide (nucleotide position 1-75) fused in frame to a synthetic nucleotide sequence encoding a ET34 protein (nucleotide position 76-450).

SEQ ID NO 8 represents the amino acid sequence translation of SEQ ID NO 7.

SEQ ID NO 9 represents the native Bt nucleotide sequence encoding a TIC1506 protein.

SEQ ID NO 10 represents the amino acid sequence translation of SEQ ID NO 9.

SEQ ID NO 11 represents an artificial nucleotide sequence encoding a TIC1506 protein.

SEQ ID NO 12 represents the amino acid sequence translation of SEQ ID NO 11.

SEQ ID NO 13 represents the native Bt nucleotide sequence encoding a TIC1501 protein.

SEQ ID NO 14 represents the amino acid sequence translation of SEQ ID NO 13.

SEQ ID NO 15 represents an artificial nucleotide sequence encoding a TIC1501 protein.

SEQ ID NO 16 represents the amino acid sequence translation of SEQ ID NO 15.

SEQ ID NO 17 represents the native Bt nucleotide sequence encoding a TIC1503 protein.

SEQ ID NO 18 represents the amino acid sequence translation of SEQ ID NO 17.

SEQ ID NO 19 represents an artificial nucleotide sequence encoding a TIC1503 protein.

SEQ ID NO 20 represents the amino acid sequence translation of SEQ ID NO 19.

SEQ ID NO 21 represents a native Bt nucleotide sequence encoding a TIC614 protein.

SEQ ID NO 22 represents an amino acid sequence translation of SEQ ID NO 21.

SEQ ID NO 23 represents an artificial nucleotide sequence encoding a TIC614 protein.

SEQ ID NO 24 represents an amino acid sequence translation of SEQ ID NO 23.

SEQ ID NO 25 represents a nucleotide sequence encoding a TIC615 protein.

SEQ ID NO 26 represents the amino acid sequence translation of SEQ ID NO 25.

SEQ ID NO 27 represents an artificial nucleotide sequence encoding a TIC615 protein.

SEQ ID NO 28 represents the amino acid sequence translation of SEQ ID NO 27.

SEQ ID NO 29 represents the native Bt nucleotide sequence encoding a TIC1277 protein.

SEQ ID NO 30 represents the amino acid sequence translation of SEQ ID NO 29.

SEQ ID NO 31 represents an artificial nucleotide sequence encoding a TIC1277 protein.

SEQ ID NO 32 represents the amino acid sequence translation of SEQ ID NO 31.

SEQ ID NO 33 represents the native Bt nucleotide sequence encoding a TIC TIC1278 protein.

SEQ ID NO 34 represents the amino acid sequence translation of SEQ ID NO 33.

SEQ ID NO 35 represents an artificial nucleotide sequence encoding a TIC TIC1278 protein.

SEQ ID NO 36 represents the amino acid sequence translation of SEQ ID NO 35.

SEQ ID NO 37 represents the native Bt nucleotide sequence encoding a TIC TIC1310 protein.

SEQ ID NO 38 represents the amino acid sequence translation of SEQ ID NO 37.

SEQ ID NO 39 represents an artificial nucleotide sequence encoding a TIC1310 protein.

SEQ ID NO 40 represents the amino acid sequence translation of SEQ ID NO 39.

SEQ ID NO 41 represents the native Bt nucleotide sequence encoding a TIC TIC1311 protein.

SEQ ID NO 42 represents the amino acid sequence translation of SEQ ID NO 41.

SEQ ID NO 43 represents an artificial nucleotide sequence encoding a TIC1311 protein.

SEQ ID NO 44 represents the amino acid sequence translation of SEQ ID NO 43.

SEQ ID NO 45 represents the native Bt nucleotide sequence encoding a TIC1324 protein.

SEQ ID NO 46 represents the amino acid sequence translation of SEQ ID NO 45.

SEQ ID NO 47 represents an artificial nucleotide sequence encoding a TIC1324 protein.

SEQ ID NO 48 represents the amino acid sequence translation of SEQ ID NO 47.

SEQ ID NO 49 represents the native Bt nucleotide sequence encoding a TIC1407 protein.

SEQ ID NO 50 represents the amino acid sequence translation of SEQ ID NO 49.

SEQ ID NO 51 represents an artificial nucleotide sequence encoding a TIC TIC1407 protein.

SEQ ID NO 52 represents the amino acid sequence translation of SEQ ID NO 51.

SEQ ID NO 53 represents the native Bt nucleotide sequence encoding a TIC TIC1408 protein.

SEQ ID NO 54 represents the amino acid sequence translation of SEQ ID NO 53.

SEQ ID NO 55 represents an artificial nucleotide sequence encoding a TIC1408 protein.

SEQ ID NO 56 represents the amino acid sequence translation of SEQ ID NO 56.

SEQ ID NO 57 represents a native Bt nucleotide sequence encoding a TIC1308 protein.

SEQ ID NO 58 represents an amino acid sequence translation of SEQ ID NO 57.

SEQ ID NO 59 represents a native Bt nucleotide sequence encoding a TIC1442 protein.

SEQ ID NO 60 represents an amino acid sequence translation of SEQ ID NO 59.

SEQ ID NO 61 represents an artificial nucleotide sequence encoding a TIC1308 protein.

SEQ ID NO 62 represents an amino acid sequence translation of SEQ ID NO 61.

SEQ ID NO 63 represents an artificial nucleotide sequence encoding a TIC1442 protein.

SEQ ID NO 64 represents an amino acid sequence translation of SEQ ID NO 63.

DETAILED DESCRIPTION OF THE INVENTION

The invention relates to methods and compositions for pest control in plants, in particular nematode and/or insect control.

In one aspect, the invention relates to controlling, preventing or treating nematode and/or insect infection in transgenic plants. The method comprises, in one embodiment, generation of transgenic plants containing a recombinant construct and expression of such construct to impart such pest resistance to plants. The recombinant construct may comprise a nucleotide sequence encoding one or more proteins, wherein the sequence is operably linked to a heterologous promoter functional in a plant cell, and to cells transformed with the recombinant construct. Cells comprising (meaning including but not limited to) the recombinant construct may be prokaryotic or eukaryotic. In particular, eukaryotic cells may be plant cells. Plants and seeds derived from such transformed plant cells are also contemplated. The transgenic plants or parts thereof of the present invention, in one embodiment, produce one or more pesticidal proteins derived from *Bacillus thuringiensis* bacterial strains.

The present invention provides heterologous molecules that are expressed in the cytoplasm of the host cell, or if used in a eukaryotic cell such as a plant cell, may also be directed into the plastid of the plant to provide production of the toxic protein, and including, but not limited to, nucleotide segments that encode polypeptides such as SEQ ID NO:2, SEQ ID NO:6, SEQ ID NO:10, SEQ ID NO:14, SEQ ID NO:18, SEQ ID NO:22, SEQ ID NO:26, SEQ ID NO:30, SEQ ID NO:34, SEQ ID NO:38, SEQ ID NO:42, SEQ ID NO:46, SEQ ID NO:50, SEQ ID NO:54, SEQ ID NO:58, and SEQ ID NO:60 having pesticidal activity. In certain embodiments, the polypeptide having pesticidal activity may share at least about 45%, or at least about 50%, or at least about 51-79%, or at least 80%, or at least 85%, or at least 90%, or at least 95%, or at least 98%, or at least 99%, or 100% sequence identity, to any one or more amino acid sequence(s) set forth in SEQ ID NO:2, SEQ ID NO:6, SEQ ID NO:10, SEQ ID NO:14, SEQ ID NO:18, SEQ ID NO:22, SEQ ID NO:26, SEQ ID NO:30, SEQ ID NO:34, SEQ ID NO:38, SEQ ID NO:42, SEQ ID NO:46, SEQ ID NO:50, SEQ ID NO:54, SEQ ID NO:58, or SEQ ID NO:60. The function of the encoded polypeptide may also be determined by measuring the efficacy of the presence of the transgene that encodes it in reducing nematode and/or insect infection, growth, reproduction, or symptomology. For instance, a reduction in root galls, cysts, or worm number of 20% or more, 25% or more, 50% or more, 80% or more, or 95% or more, in a transgenic plant comprising a heterologous nucleotide construct encoding any of the proteins of the present invention, relative to a control plant, for instance an otherwise isogenic plant not comprising the heterologous molecule, under similar conditions, indicates the presence of a functional molecule.

In certain embodiments, a heterologous molecule provided by the present invention that is directed into the plastid of a plant to provide production of a toxin protein of the present invention may share at least from about 60 to about 79%, or at least 80%, or at least 85%, or at least 90%, or at least 95%, or at least 98%, or at least 99%, or 100% sequence identity at the nucleotide level with one or more sequence(s) as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, and SEQ ID NO:63.

Thus, in particular embodiments, the heterologous molecule may comprise a sequence encoding a heterologous chloroplast transit peptide.

Yet another aspect of the invention provides methods for production and for use of one or more of the proteins of the present invention to control nematode and/or insect infestation. Thus, methods for production of a toxin, for instance in a plant cell, are provided. The toxin may then be applied to soil prior to, during, or subsequent to planting of a crop, in order to control or reduce nematode infestation or symptomotology of crop plants grown in that soil.

Unless otherwise noted, terms are to be understood according to conventional usage by those of ordinary skill in the relevant art. Definitions of common terms in molecular biology may also be found in Rieger et al., *Glossary of Genetics: Classical and Molecular,* 5th edition, Springer-Verlag: New York, 1991; and Lewin, Genes V, Oxford University Press: New York, 1994. The nomenclature for DNA bases as set forth at Title 37 of the United States Code of Federal Regulations, Part 1, section 1.822.

As used herein, a “transgenic plant” is any plant in which one or more, or all, of the cells of the plant include a transgene. A transgene may be integrated within a nuclear genome or organelle genome, or it may be extra-chromosomally replicating DNA. The term “transgene” means a nucleic acid that is partly or entirely heterologous, foreign, to a transgenic microbe, plant, animal, or cell into which it is introduced. Cells that make up various cell and tissue types of plants include but are not limited to seed, root, leaf, shoot, flower, pollen and ovule.

“Recombinant DNA” is a polynucleotide having a genetically engineered modification introduced through combination of endogenous and/or exogenous molecules in a transcription unit, manipulation via mutagenesis, restriction enzymes, and the like or simply by inserting multiple copies of a native transcription unit. Recombinant DNA may comprise DNA segments obtained from different sources, or DNA segments obtained from the same source, but which have been manipulated to join DNA segments which do not naturally exist in the joined form. An isolated recombinant polynucleotide may exist, for example as a purified molecule, or integrated into a genome, such as a plant cell, or organelle genome or a microbe plasmid or genome. The polynucleotide comprises linked regulatory molecules that cause transcription of an RNA in a plant cell.

As used herein, “percent identity” means the extent to which two optimally aligned DNA or protein segments are invariant throughout a window of alignment of components, for example nucleotide sequence or amino acid sequence. An “identity fraction” for aligned segments of a test sequence and a reference sequence is the number of identical components that are shared by sequences of the two aligned segments divided by the total number of sequence components in the reference segment over a window of alignment which is the smaller of the full test sequence or the full reference sequence. “Percent identity” (“% identity”) is the identity fraction times 100.

“Expression” means transcription of DNA to produce RNA. The resulting RNA may be without limitation mRNA encoding a protein, antisense RNA, or a double-stranded RNA for use in RNAi technology. Expression also may refer to translation of RNA, i.e. the production of encoded protein from an mRNA.

As used herein, “promoter” means regulatory DNA molecules for initializing transcription. A “plant promoter” is a promoter capable of initiating transcription in plant cells whether or not its origin is a plant cell. For example it is well known that certain *Agrobacterium* promoters are functional in plant cells. Thus, plant promoters include promoter DNA obtained from plants, plant viruses (in particular, double stranded DNA viruses) and bacteria such as *Agrobacterium* and *Bradyrhizobium* bacteria. Constitutive promoters generally provide transcription in most or all of the cells of a plant. In particular, promoters such as the FMV promoter (FMV, U.S. Pat. No. 6,051,753), the enhanced 35S promoter (E35S, U.S. Pat. No. 5,359,142), rice actin promoter (U.S. Pat. No. 5,641,876), and various chimeric promoters (U.S. Pat. No. 6,660,911) are useful in the present invention. Examples of promoters under developmental control include promoters that preferentially initiate transcription in certain tissues, such as leaves, roots, or seeds. Such promoters are referred to as "tissue-preferred". Promoters that initiate transcription only in certain tissues are referred to as "tissue specific."

A number of root-specific or root-enhanced promoters or fragments of such that provide enhanced expression in root tissues relative to other plant tissues have been identified and are known in the art (e.g. U.S. Pat. Nos. 5,110,732, 5,837,848, 5,837,876; 5,633,363; 5,459,252; 5,401,836; 7,196,247; 7,232,940; 7,119,254; and 7,078,589). Examples include root-enhanced or root-specific promoters such as the CaMV-derived as-1 promoter or the wheat POX1 promoter (U.S. Pat. No. 5,023,179), the acid chitinase gene promoter (Samac et al., *Plant Mol. Biol.* 25:587-596 (1994); the root specific subdomains of the CaMV35S promoter (Lam et al., *Proc. Natl. Acad. Sci.* (*U.S.A.*) 86:7890-7894 (1989); the root-enhanced ORF13 promoter from *Agrobacterium rhizogenes* (Hansen et al., *Mol. Gen. Genet.* 254:337-343 (1997); the promoter for the tobacco root-specific gene RB7 (U.S. Pat. No. 5,750,386); and the root cell-specific promoters reported by Conkling et al. (*Plant Physiol.* 93:1203-1211 (1990). Additional examples include RCc2 and RCc3, promoters that direct root-specific gene transcription in rice (Xu et al., *Plant Mol. Biol.* 27:237, 1995); soybean root-specific glutamine synthetase promoter (Hire et al., *Plant Mol. Biol.* 20:207-218, 1992); root-specific control element in the GRP 1.8 gene of French bean (Keller and Baumgartner, *Plant Cell* 3:1051-1061, 1991.); a root-specific promoter of the mannopine synthase (MAS) gene of *Agrobacterium tumefaciens* (Sanger et al., *Plant Mol. Biol.* 14:433-443, 1990); and full-length cDNA clone encoding cytosolic glutamine synthetase (GS), which is expressed in roots and root nodules of soybean (Miao et al., *Plant Cell* 3:11-22, 1991). See also Bogusz et al., *Plant Cell* 2:633-641, 1990, where two root-specific promoters isolated from hemoglobin genes from the nitrogen-fixing non-legume *Parasponia andersonii* and the related non-nitrogen-fixing non-legume *Trema tomentosa* are described. Leach and Aoyagi (1991) describe their analysis of the promoters of the highly expressed rolC and rolD root-inducing genes of *Agrobacterium rhizogenes* (see *Plant Science* (Limerick) 79:69-76). Additional root-preferred promoters include the VfENOD-GRP3 gene promoter (Kuster et al., *Plant Mol. Biol.* 29(4):759-772, 1995); and rolB promoter (Capana et al., *Plant Mol. Biol.* 25:681-691, 1994). Examples of nematode-induced promoters include, for instance, the TobRB7 promoter (Opperman et al., *Science* 263:221-223, 1994), and promoters described in U.S. Pat. Nos. 6,262,344, and 7,193,136.

The term "resistance," or "tolerance" when used in the context of comparing the effectiveness of a transgene in a transgenic plant, refers to the ability of the transgenic plant to maintain a desirable phenotype when exposed to nematode infestation pressures relative to the phenotype presented by a nematode sensitive non-transgenic plant under similar conditions. The level of resistance can be determined by comparing the physical characteristics of the transgenic plant to non-transgenic plants that either have or have not been exposed to nematode and/or insect infection. Exemplary physical characteristics to observe include plant height, an increase in population of plants that have ability to survive nematode or insect challenge (that is, plants that come in contact with a parasitic nematode or insect may have enhanced root growth, enhanced fruit or grain yield, and decreased reproduction of the nematode or insect infesting the plant or crop, or a decrease in the rate of increase if the pest population). The product of expression of the recombinant DNA may be directly toxic to the nematode (nematicidal) or insect (insecticidal), or may affect the mobility, host finding, feeding site establishment, fecundity or have other nematistatic and/or insectic inhibitory effects.

"Transformed seed" is the seed which has been generated from the transformed plant. A transformed plant contains transformed cells. A transformed cell is a cell that has been altered by the introduction of an exogenous DNA molecule or in the present invention comprises a heterologous DNA encoding one or more of the proteins of the present invention.

Pests intended to be within the scope of the present invention include the "lepidopteran pest population" such as *Spodoptera frugiperda, Spodoptera exigua, Mamestra configurata, Agrotis ipsilon, Trichoplusia ni, Pseudoplusia includens, Anticarsia gemmatalis, Hypena scabra, Heliothis virescens, Agrotis subterranea, Pseudaletia unipuncta, Agrotis orthogonia, Ostrinia nubilalis, Amyelois transitella Crambus caliginosellus, Herpetogramma licarsisalis, Homoeosoma electellum, Elasmopalpus lignosellu, Cydia pomonella, Endopiza viteana, Grapholita molesta, Suleima helianthana, Plutella xylostella, Pectinophora gossypiella, Lymantria dispar, Blatta orientalis, Blatella asahinai, Blattella germanica, Supella longipalpa, Periplaneta americana, Periplaneta brunnea, Leucophaea maderae, Alabama argillacea, Archips argyrospila, A. rosana, Chilo suppressalis, Cnaphalocrocis medinalis, Crambus caliginosellus, C. teterrellus, Diatraea grandiosella, D. saccharalis, Earias insulana, E. vittella, Helicoverpa armigera, H. zea, Heliothis virescens, Herpetogramma licarsisalis, Lobesia botrana, Pectinophora gossypiella, Phyllocnistis citrella, Pieris brassicae, P. rapae, Plutella xylostella, Spodoptera exigua, S. litura, S. frugiperda*, and *Tuta absoluta*. The "coleopteran pest population" includes *Anthonomus grandis, Lissorhoptrus oryzophilu, Sitophilus granaries, Sitophilus oryzae, Hypera punctata, Sphenophorus maidis, Leptinotarsa decemlineata, Diabrotica virgifera virgifera, Diabrotica barberi, Diabrotica undecimpunctata howardi, Chaetocnema pulicaria, Phyllotreta cruciferae, Colaspis brunnea, Oulema melanopus, Zygogramma exclamationis, Epilachna varivestis, Popillia japonica, Cyclocephala boreali, Cyclocephala immaculata, Rhizotrogus majalis, Phyllophaga crinita, Ligyrus gibbosus, Melanotus* spp., *Conoderus* spp., *Limonius* spp., *Agriotes* spp., *Ctenicera* spp., and *Aeolus* spp., *Eleodes* spp. The "plant pathogenic nematode population" includes plant parasitic species, for example, *Heterodera* species, *Globodera species, Meloidogyne* species, *Rotylenchulus* species, *Hoplolaimus* species, *Belonolaimus* species, *Pratylenchus* species, *Longidorus* species, *Paratrichodorus* species, *Ditylenchus* species, *Xiphinema* species, *Dolichodorus* species, *Helicotylenchus* species, *Radopholus* species, *Hirschmanniella* species, *Tylenchorhynchus* species, and *Trichodorus* species, and the like, and specifically includes *Heterodera glycines* (soybean cyst nematode), *Heterodera schachtii* (beet cyst nematode), *Heterodera avenae, Globodera rostochiensis, Globodera pailida, Pratylenchus zeae* (a root knot nematode), *Meloidogyne javanica, Pratylenchus brachyurus* (a root knot nematode), *Meloidogyne hapla*, and *Meloidogyne incognita.*

The present invention provides recombinant DNA constructs comprising a polynucleotide that, when incorporated in a plant cell, imparts to the plant resistance to nematode and/or insect infection or plant disease caused by such infection (also referred to as infestation). Such constructs also typically comprise a promoter operatively linked to said polynucleotide to provide for expression in the plant cells. Other construct components may include additional regulatory molecules, such as 5' leader regions or 3' untranslated regions (such as polyadenylation sites), intron regions, and transit or signal peptides. Such recombinant DNA constructs can be assembled using methods known to those of ordinary skill in the art.

Recombinant constructs prepared in accordance with the present invention also generally include a 3' untranslated DNA region (UTR) that typically contains a polyadenylation sequence following the polynucleotide coding region. Examples of useful 3' UTRs include but are not limited to those from the nopaline synthase gene of *Agrobacterium tumefaciens* (nos), a gene encoding the small subunit of a ribulose-1,5-bisphosphate carboxylase-oxygenase (rbcS), and the T7 transcript of *Agrobacterium tumefaciens.*

Constructs and vectors may also include a transit peptide for targeting of a protein product, particularly to a chloroplast, leucoplast or other plastid organelle, mitochondria, peroxisome, or vacuole or an extracellular location. For descriptions of the use of chloroplast transit peptides, see U.S. Pat. No. 5,188,642 and U.S. Pat. No. 5,728,925. Many chloroplast-localized proteins are expressed from nuclear genes as precursors and are targeted to the chloroplast by a chloroplast transit peptide (CTP). Examples of other such isolated chloroplast proteins include, but are not limited to those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS) and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide, such as, the *Arabidopsis thaliana* EPSPS CTP (CTP2, Klee et al., *Mol. Gen. Genet.* 210:437-442, 1987), and the *Petunia hybrida* EPSPS CTP (CTP4, della-Cioppa et al., *Proc. Natl. Acad. Sci. USA* 83:6873-6877, 1986) has been show to target heterologous EPSPS protein sequences to chloroplasts in transgenic plants. The production of glyphosate tolerant plants by expression of a fusion protein comprising an amino-terminal CTP with a glyphosate resistant EPSPS enzyme is well known by those skilled in the art, (U.S. Pat. No. 5,627,061, U.S. Pat. No. 5,633,435, U.S. Pat. No. 5,312,910, EP 0218571, EP 189707, EP 508909, and EP 924299). Those skilled in the art will recognize that various chimeric constructs can be made that utilize the functionality of a CTP to import various pesticidal proteins of the present invention into the plant cell plastid.

Stable methods for plant transformation include virtually any method by which DNA can be introduced into a cell, such as by direct delivery of DNA (for example, by PEG-mediated transformation of protoplasts, by electroporation, by agitation with silicon carbide fibers, and by acceleration of DNA coated particles), by *Agrobacterium*-mediated transformation, by viral or other vectors. One preferred method of plant transformation is microprojectile bombardment, for example, as illustrated in U.S. Pat. No. 5,015,580 (soy), U.S. Pat. No. 5,550,318 (maize), U.S. Pat. No. 5,538,880 (maize), U.S. Pat. No. 6,153,812 (wheat), U.S. Pat. No. 6,160,208 (maize), U.S. Pat. No. 6,288,312 (rice) and U.S. Pat. No. 6,399,861 (maize), and U.S. Pat. No. 6,403,865 (maize).

Detailed procedures for *Agrobacterium*-mediated transformation of plants, especially crop plants, include, for example, procedures disclosed in U.S. Pat. Nos. 5,004,863, 5,159,135, 5,518,908, 5,846,797, and 6,624,344 (cotton); U.S. Pat. Nos. 5,416,011, 5,569,834, 5,824,877, 5,914,451 6,384,301, and 7,002,058 (soy); U.S. Pat. Nos. 5,591,616 5,981,840, and 7,060,876 (maize); U.S. Pat. Nos. 5,463,174 and 5,750,871 (*Brassica* species, including rapeseed and canola), and in U.S. Patent Application Publications 2004/0244075 (maize), 2004/0087030 (cotton) and 2005/0005321 (soybean). Additional procedures for *Agrobacterium*-mediated transformation are disclosed in WO9506722 (maize). Similar methods have been reported for many plant species, both dicots and monocots, including, among others, peanut (Cheng et al., *Plant Cell Rep.,* 15:653, 1996); asparagus (Bytebier et al., *Proc. Natl. Acad. Sci. U.S.A.,* 84:5345, 1987); barley (Wan and Lemaux, *Plant Physiol.,* 104:37, 1994); rice (Toriyama et al., *Bio/Technology,* 6:10, 1988; Zhang et al., *Plant Cell Rep.,* 7:379, 1988; wheat (Vasil et al., *Bio/Technology,* 10:667, 1992; Becker et al., *Plant J.,* 5:299, 1994), alfalfa (Masoud et al., *Transgen. Res.,* 5:313, 1996); *Brassica* species (Radke et al., *Plant Cell Rep.,* 11:499-505, 1992); and tomato (Sun et al., *Plant Cell Physiol.,* 47:426-431, 2006). Transgenic plant cells and transgenic plants can also be obtained by transformation with other vectors, such as but not limited to viral vectors (for example, tobacco etch virus (TEV), barley stripe mosaic virus (BSMV), and the viruses referenced in Edwardson and Christie, "The Potyvirus Group Monograph No. 16", 1991, Agric. Exp. Station, Univ. of Florida), plasmids, cosmids, YACs (yeast artificial chromosomes), BACs (bacterial artificial chromosomes) or any other suitable cloning vector, when used with an appropriate transformation protocol such as but not limited to bacterial infection (for example, with *Agrobacterium* as described above), binary bacterial artificial chromosome constructs, direct delivery of DNA (for example, via PEG-mediated transformation, desiccation/inhibition-mediated DNA uptake, electroporation, agitation with silicon carbide fibers, and microprojectile bombardment). It would be clear to one of ordinary skill in the art that various transformation methodologies can be used and modified for production of stable transgenic plants from any number of plant species of interest. For example the construction of stably inherited recombinant DNA constructs and mini-chromosomes can be used as vectors for the construction of transgenic plants (U.S. Pat. No. 7,235,716).

Plants of the present invention include, but are not limited to, *Acacia*, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassava, cauliflower, celery, cherry, cilantro, citrus, clementine, coffee, corn, cotton, cucumber, Douglas fir, eggplant, endive, escarole, eucalyptus, fennel, figs, forest trees, gourd, grape, grapefruit, honey dew, jicama, kiwifruit, lettuce, leeks, lemon, lime, loblolly pine, mango, melon, mushroom, nut, oat, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, turf, a vine, watermelon, wheat, yams, and zucchini. Crop plants are defined as plants which are cultivated to produce one or more commercial products. Examples of such crops or crop plants include but are not limited to soybean, canola, rape, cotton (cottonseeds), peanut, sunflower, pigeon pea, chickpea, and the like, and grains such as corn, wheat, rice, oat, millet, and rye, and the like. Rape, rapeseed and canola are used synonymously in the present disclosure.

Transformation methods to provide transgenic plant cells and transgenic plants containing stably integrated recombinant DNA are preferably practiced in tissue culture on media and in a controlled environment. Recipient cell targets include but are not limited to meristem cells, callus, immature embryos or parts of embryos, gametic cells such as microspores, pollen, sperm, and egg cells. Any cell from which a fertile plant can be regenerated is contemplated as a useful recipient cell for practice of the invention. Callus can be initiated from various tissue sources, including, but not limited to, immature embryos or parts of embryos, seedling apical meristems, microspores, and the like. Those cells which are capable of proliferating as callus can serve as recipient cells for genetic transformation. Practical transformation methods and materials for making transgenic plants of this invention (for example, various media and recipient target cells, transformation of immature embryos, and subsequent regeneration of fertile transgenic plants) are disclosed, for example, in U.S. Pat. Nos. 6,194,636 and 6,232,526 and U.S. Patent Application Publication 2004/0216189.

In general transformation practice, DNA is introduced into only a small percentage of target cells in any one transformation experiment. Marker genes are generally used to provide an efficient system for identification of those cells that are transformed by a transgenic DNA construct. Preferred marker genes provide selective markers which confer resistance to a selective agent, such as an antibiotic or herbicide. Any of the antibiotics or herbicides to which a plant cell may be resistant can be a useful agent for selection. Potentially transformed cells are exposed to the selective agent. In the population of surviving cells will be those cells where, generally, the resistance-conferring gene is expressed at sufficient levels to permit cell survival in the presence of the selective agent. Cells can be tested further to confirm integration of the recombinant DNA. Commonly used selective marker genes include those conferring resistance to antibiotics such as kanamycin or paromomycin (val), hygromycin B (aph IV), gentamycin (aac3 and aacC4) and glufosinate (bar or pat), glyphosate (EPSPS), and dicamba (dicamba monooxygenase). Examples of useful selective marker genes and selection agents are illustrated in U.S. Pat. Nos. 5,550,318, 5,633,435, 5,780,708, and 6,118,047. Screenable markers or reporters, such as markers that provide an ability to visually identify transformants can also be employed. Non-limiting examples of useful screenable markers include, for example, a gene expressing a protein that produces a detectable color by acting on a chromogenic substrate (for example, beta-glucuronidase, GUS, uidA, or luciferase, luc) or that itself is detectable, such as green fluorescent protein (GFP, gfp) or an immunogenic molecule. Those of skill in the art will recognize that many other useful markers or reporters are available for use.

The recombinant DNA constructs of the invention can be stacked with other recombinant DNA for imparting additional agronomic traits (such as in the case of transformed plants, traits including but not limited to herbicide resistance, insect resistance, cold germination tolerance, water deficit tolerance, enhanced yield, enhanced quality, fungal, viral, and bacterial disease resistance) for example, by expressing other transgenes. The recombinant DNA constructs of the present invention can also be transformed into plant varieties that carry natural pest or pathogen resistance genes to enhance the efficacy of the resistance phenotype. Constructs for coordinated decrease and/or increase of gene expression are disclosed in U.S. Patent Application Publication 2004/0126845 A1. Seeds of transgenic, fertile plants can be harvested and used to grow progeny generations, including hybrid generations, of transgenic plants of this invention that include the recombinant DNA construct in their genome. Thus, in addition to direct transformation of a plant with a recombinant DNA construct of this invention, transgenic plants of the invention can be prepared by crossing a first plant having the recombinant DNA with a second plant lacking the construct. For example, the recombinant DNA can be introduced into a plant line that is amenable to transformation to produce a transgenic plant, which can be crossed with a second plant line to introgress the recombinant DNA into the resulting progeny. A transgenic plant of the invention can be crossed with a plant line having other recombinant DNA or naturally occurring genetic regions that confers one or more additional trait(s) (such as, but not limited to, herbicide resistance, pest or disease resistance, environmental stress resistance, modified nutrient content, and yield improvement) to produce progeny plants having recombinant DNA that confers both the desired target sequence expression behavior and the additional trait(s). Typically, in such breeding for combining traits the transgenic plant donating the additional trait is a male line and the transgenic plant carrying the base traits is the female line. The progeny of this cross segregate such that some of the plant will carry the DNA for both parental traits and some will carry DNA for one parental trait; such plants can be identified by markers associated with parental recombinant DNA. Progeny plants carrying DNA for both parental traits can be crossed back into the female parent line multiple times, for example, usually 6 to 8 generations, to produce a progeny plant with substantially the same genotype as one original transgenic parental line but for the recombinant DNA of the other transgenic parental line.

Other proteins and toxic agents can be used together with one or more proteins of the present invention to control plant pathogenic nematode and/or insect infestation and to reduce the likelihood of development of resistance to any single method of control. Such other proteins and toxic agents include but are not limited to, as applicable to either nematode or insect control, methylketone synthase, dsRNA expressed in the cell and targeting for suppression one or more essential, housekeeping, reproductive or developmental gene, other proteins that are known in the art to be toxic to plant pathogenic nematodes or insects such as Cry and VIP proteins (lifesci.sussex.ac.uk/home/Neil_Crickmore/Bt/index.html" on the world wide web, which is properly referenced as Crickmore et. al. (2010) "*Bacillus thuringiensis* toxin nomenclature"), as well as chemical nematicides used in seed treatments or soil drenches. Topically applied dsRNA methods are also known in the art that can be applied to a plant expressing one or more of the proteins of the present invention. Such topical applications can be effective in causing a systemic effect in the plant that result in nematode or insect control by applying to the plant a dsRNA molecule that targets for regulation a gene in the plant involved in such resistance. All such combinations are within the scope of the present invention.

The transgenic plant, plant part, seed or progeny plants of the present invention can be processed into products useful in commerce. These products, commodity products, include but are not limited to meal, flour, oil, hay, starch, juice, protein extract, and fiber.

The proteins of the present invention have been identified using a variety of methods. One method has been to identify previously known Bt proteins that exhibit a mass less than about 40 kDa, or less than about 35 kDa, or less than about 30 kDa, or less than about 28 kDa, or less than about 25 kDa, or less than about 20 kDa, or less than about 15 kDa. Such proteins include but are not limited to the smaller component of most known binary Bt toxins, such as Cry34/35 (PS149B1), TIC100/101, ET33/34, ET80/76, and the like. Other proteins known in the art include TIC901, TIC1201, TIC407, TIC417, TIC431, ET70, VIP proteins such as VIP3Aa and the like, which are all generally small toxin proteins that are known to exhibit insecticidal activity. The inventors herein have identified that such smaller toxin molecules, when provided in the diet of a *C. elegans* nematode, exhibit various levels of inhibitory effects. Surprisingly, it has also been observed that the nematidical activity of these proteins can be imparted through the diet of a cyst nematode more effectively by truncating the proteins to smaller sizes, whether truncated at the C terminus, the N terminus, or both. Truncated versions typically exhibit a mass of from about 14 to about 28-30 kDa, and exhibit improved bioactivity likely because the ability of the cyst nematode to uptake proteins larger than about 30 kDa is limited (Urwin et al. ((1997) Plant J. 12:455) and Bockenhoff & Grundler ((1994) Parasitology 109:249). TIC1501 (about 27 kDa), TIC1503 (about 34 kDa), and TIC1506 (about 36 kDa) represent various fragments of the TIC1201 protein, 1201 being previously shown to exhibit coleopteran toxic effects. Surprisingly, the truncated versions less than 36 kDa exhibit significant nematicidal effects.

Proteins of the present invention have also been identified de novo, and these include the proteins listed herein as TIC614, TIC615, TIC1277, TIC1278, TIC1308, TIC1310, TIC1311, TIC1324, TIC1407, TIC1408, and TIC1442. Such proteins were identified by various methods, whether being directly amplified from various Bt strain genomes, or identified by high throughput sequence analysis of various Bt genomes. In either case, genomic DNA segments are obtained and analyzed using bioinformatic techniques that result in the identification of all or portions of open reading frames encoding protein segments. The resulting protein segments are then characterized versus all known protein sequences in the art, and to the extent that there is any similarity to a toxin molecule, the complete sequence of the open reading frame encoding the protein is obtained. Proteins that are identified that exhibit a mass of less than about 40 kDa, or preferably less than about 30 kDa are then evaluated in a *C. elegans* assay to determine if any effects are observed relative to *C. elegans* survival. Toxins exhibiting nematicidal properties are then evaluated for other pesticidal properties, particularly insecticidal activity. Surprisingly, the above referenced proteins all exhibited nematicidal activity, and some exhibited insecticidal activity as reported in the examples below.

EXAMPLES

The following examples are illustrative of the invention, which may be embodied in various forms and are not to be interpreted as limiting the scope or content of the disclosure in any way.

Example 1

DNA Molecules Encoding Bt Toxin Proteins

Toxin ET34 (SEQ ID NO:1) has been previously described (U.S. Pat. No. 6,063,756). A secretion signal from the gene P139 (First 75 nucleotide of SEQ ID NO:1 from the WIPO Publication Number WO9408010) was operably linked to the 5' end of the ET34 (SEQ ID NO:5) to enable its secretion outside the plasma membrane to avoid potential toxicity to the plant cell and to allow easy access of the protein to the pest.

TIC1506 (SEQ ID NO:9), TIC1501 (SEQ ID NO:13), and TIC 1503 (SEQ ID NO:17) are Bt nucleotide of various fragments of TIC1201 which is 364 amino acids long as set forth in SEQ ID NO 6 of US Patent Application Publication Number US2006-0191034 A1. TIC1506 is 321 amino acids long without the putative N terminal signal peptide of TIC1201 and contains amino acid 44 to 364 of TIC1201 with a methionine residue substituted for the native alanine residue at amino acid position 44. TIC1501 is 227 amino acids long without the putative N terminal signal peptide and a portion of the C terminal of TIC1201 and contains amino acids 44 to 270 of TIC1201 with a methionine residue substituted for the native alanine residue at position 44. TIC1503 is 301 amino acids long without the putative N terminal signal peptide and a portion of the C terminal of TIC1201 and contains amino acids 44 to 344 of TIC1201 with a methionine residue substituted for the native alanine residue at position 44.

Proteins exhibiting pesticidal properties have been identified in various Bt strains. Open reading frames encoding the amino acid sequences, TIC614 (SEQ ID NO: 22), TIC615 (SEQ ID NO: 26), TIC1277 (SEQ ID NO: 30), TIC1278 (SEQ ID NO: 34), TIC1310 (SEQ ID NO: 38), TIC1311 (SEQ ID NO: 42), TIC1324 (SEQ ID NO: 46), TIC1407 (SEQ ID NO: 50), and TIC1408 (SEQ ID NO: 54), exhibiting various degrees of homology to previously known Bt toxin segments were identified. Complete forward and reverse sequence analysis of such open reading frames resulted in the identification of deduced amino acid compositions that exhibit the size and potential for pesticidal (nematicidal and/or insecticidal) activity.

Proteins exhibiting pesticidal properties have been identified in various Bt strains. Open reading frames encoding the amino acid sequences, TIC1308 (SEQ ID NO: 58) and TIC1442 (SEQ ID NO: 60), exhibiting various degrees of homology to previously known Bt toxin segments were identified. Complete forward and reverse sequence analysis of such open reading frames resulted in the identification of deduced amino acid compositions that exhibit the size and potential for pesticidal (nematicidal and/or insecticidal) activity.

Example 2

Expression of Pesticidal Polypeptides from Polynucleotides

Open reading frames of ET34 (SEQ ID NO: 1), P139-ET34 (SEQ ID NO: 5), TIC1506 (SEQ ID NO:9), TIC1501 (SEQ ID NO:13), TIC 1503 (SEQ ID NO:17), TIC614 (SEQ ID NO:21), TIC615 (SEQ ID NO:25), TIC1277 (SEQ ID NO:29), TIC1278 (SEQ ID NO:33), TIC1310 (SEQ ID NO:37), TIC1311 (SEQ ID NO:41), TIC1324 (SEQ ID NO:45), TIC1407 (SEQ ID NO:49), TIC1408 (SEQ ID NO:53), TIC1308 (SEQ ID NO: 57), and TIC1442 (SEQ ID NO: 59) encoding the deduced amino acid compositions exemplified in Example 1 were cloned into a Bt/*E. coli* shuttle plasmid enabling the expression of the deduced amino acid composition in either an acrystalliferous Bt strain or in an *E. coli* bacterium. Recombinant plasmids were transformed into an acrystalliferous Bt expression host after confirming the DNA sequence of the polynucleotide encoding the polypeptide. The gene of interest was cloned downstream of either a *Bacillus* vegetative stage or sporulation stage specific promoter to allow the protein to be expressed respectively during vegetative growth or during sporulation of the recombinant Bt strain. Conditions for vegetative expression of the protein included growing the cells for 24-48 hrs in Terrific Broth medium at 25-28° C. Crystal formation is one characteristic of certain Bt toxin proteins. Proteins that were confirmed to produce crystals when expressed in the acrystalliferous Bt strain were further evaluated. Certain proteins accumulated in the cells and/or were secreted into the culture medium. Both the cell pellets and the culture were analyzed by SDS-PAGE for expression of the expected protein. Conditions for expression from a sporulation specific promoter included growing the cells for 96 hrs at 25-28° C. in C2 medium. Protein crystals were formed during sporulation and released from lysed cells as sporulation was completed. Spores and crystals were collected by centrifugation at 4000×g for 20 minutes, resuspended in wash buffer (10 mM Tris, 0.1 mM EDTA and 0.005% Triton X100 pH 6.8) and collected again by centrifugation. The spore-crystals pellets were then resuspended in $1/10^{th}$ of the original culture volume. The 10× concentrated spore-crystal preparation were analyzed by SDS-PAGE the presence of the expected protein.

Example 3

Nematode and Insect Bioassays

*C. elegans* feeding screens have been successfully used to identify plant pathogenic nematode-active toxins, for example for SCN and RKN from the order Tylenchida (Wei et al., 2003, PNAS, USA, 100: 2760). The proteins of the present invention were expressed and provided in the diet of a *C. elegans* nematode, essentially following the method of Wei et al. Efficacy was scored on a scale of 1-3, where a score of 1 represents normal health and reproduction of *C. elegans*, and a score of 3 represents no reproduction or poor health of *C. elegans*. Toxins ET34 (SEQ ID NO: 2), TIC1501 (SEQ ID NO: 14), TIC1503 (SEQ ID NO: 18), TIC614 (SEQ ID NO:22), TIC615 (SEQ ID NO:26), TIC1277 (SEQ ID NO:30), TIC1278 (SEQ ID NO:34), TIC1310 (SEQ ID NO:38), TIC1311 (SEQ ID NO:42), TIC1324 (SEQ ID NO:46), and TIC1407 (SEQ ID NO:50), each exhibited a score of 3 where as TIC1408 (SEQ ID NO:54) exhibited a score of 2.75. Proteins TIC1308 (SEQ ID NO: 58) and TIC1442 (SEQ ID NO: 60), each exhibited a score of 1. Proteins were expressed from a vegetative specific promoter and fed to insects by applying sporulated bacterial cells or culture supernatant to artificial insect diet. For polypeptides expressed from a sporulation specific promoter a 10-20× spore-crystal preparation with about 500-4000 ppm protein was applied to the insect diet. Stunting or mortality was observed on one or more of these insects: CEW (Corn Ear Worm); SCR (Southern corn Root worm); WCR (western corn root worm); ECB (European corn borer); WTPB (Western tarnished plant bug); TPB (Tarnished plant bug); FAW (Fall army worm); CPB (Colorado potato beetle). TIC1277 and TIC1311 were found to cause significant stunting of ECB and TIC1310 was found to cause significant stunting of WTPB and significant stunting and mortality of CPB.

Example 4

Transformed Plants

Nucleotide segments encoding TIC1506 (SEQ ID NO:11), TIC1503 (SEQ ID NO: 19), TIC614 (SEQ ID NO:3), TIC1324 (SEQ ID NO:27), TIC1407 (SEQ ID NO:31), TIC1408 (SEQ ID NO:35), are codon-optimized for plant expression and operably linked to one or more plant functional promoters and introduced into plant cells. Recombinant plants are regenerated from such transformed plant cells, and the regenerated plants are evaluated for resistance to pest infestation, such as insect tolerance and/or plant pathogenic nematode tolerance.

Nucleotide segments encoding ET34 (SEQ ID NO:3), ET34+P139 secretion signal (SEQ ID NO:7), TIC1501 (SEQ ID NO:15), TIC615 (SEQ ID NO:7), TIC1277 (SEQ ID NO:11), TIC1278 (SEQ ID NO:15), TIC1310 (SEQ ID NO:19), TIC1311 (SEQ ID NO:23), TIC1308 (SEQ ID NO: 61), and TIC1442 (SEQ ID NO: 63) were codon-optimized for plant expression and operably linked to one or more plant functional promoters and introduced into plant cells. Recombinant plants were regenerated from such transformed plant cells, and the regenerated plants were evaluated for resistance to pest infestation, such as insect tolerance and/or plant pathogenic nematode tolerance.

Example 5

Transformation of Soybean

This example describes a method of producing transgenic soybean plants and transgenic plant parts such as seeds. Other methods are known in the art of plant cell transformation that can be applied to transform plant cells and regenerate transgenic plants using the recombinant constructs of the invention. The methods of obtaining transgenic soybean plants and seeds are used as essentially disclosed in US Patent Application Publication Number US2009-0138985A1. Briefly, *Agrobacterium* containing a construct of Example 5 are grown in Luria Burtani (LB) media containing spectinomycin at about 28° C. for over night. The bacterial culture is centrifuged, pellet washed, and resuspended in INO medium for inoculating wet or dry mature embryos explants. The explants are mixed with the *Agrobacterium* cell suspensions and briefly exposed to sonication energy from a standard laboratory water bath cleaning sonicator. The explants are drained of any liquid and transferred to containers containing filter paper moistened with INO media and co-cultured in a lighted chamber at about 16 hours of light (≥5 uE) at about 23° to 28 C.° for 1 to 5 days. After co-culture, the explants are placed directly onto regeneration media containing a selective agent such as spectinomycin from about 7 to about 42 days. The cultures are subsequently transferred to a media suitable for the recovery of transformed plantlets. Spectinomycin resistant shoots that have green buds or leaves are considered transformed and placed in soil or on a soil substitute for rooting in the presence or absence of the selective agent. Progeny transgenic plants and seed are selected that provide pest resistance, especially nematode resistance.

Example 6

Testing of Transgenic Plant for Soybean Cyst Nematode (SCN) Resistance

An SCN pot assay was used to evaluate the resistance of transgenic soybean plants comprising one or more of the polynucleotide sequences of SEQ ID NOs: 3, 7, and 15 to infection by and reproduction of the SCN (*Heterodera glycines*) on roots. Three or four inch diameter square pots were filled with clean sand and watered thoroughly. Transgenic and control soybean seeds, or alternatively any rooted plant parts, were planted one per pot in the center of the pot and watered well to remove air pockets. The pots were incubated in the greenhouse or growth chamber at 20° C. to 30° C. until the plants reached a suitable age for inoculation. Soybeans started from seed were typically inoculated 2-3 weeks after planting, while transplants were inoculated 1-3 days after planting. The test inoculum consisted of eggs from ripe *H. glycines* cysts collected from the soil and roots of infested soybean plants. An 80 micron mesh sieve was used to collect the cysts, which were then crushed in a Tenbroeck glass tissue homogenizer to release the eggs. The eggs were further purified by sieving and centrifugation over 40 percent sucrose solution at 4000 RPM for 5 minutes. Inoculum for an experiment consisted of water containing 500 vermiform eggs per mL. Five mL of the egg suspension was applied over the surface of the sand containing the test plants and the eggs were lightly watered in. The test plants were then returned to the greenhouse or growth chamber and incubated for 3-4 weeks to allow for root infection and cyst formation. The roots were then harvested. The severity of nematode infection was measured by counting the number of nematode cysts adhering to the root system.

Transgenic soybean plants comprising SEQ ID NO: 3 were tested in six different constructs, where in each construct SEQ ID NO: 3 was operably linked to a different promoter. Transgenic soybean plants comprising SEQ ID NO: 7 were tested in two different constructs, each construct having a different promoter. Transgenic soybean plants comprising SEQ ID NO: 15 were tested expressed from one construct.

Table 1 reports data illustrating plants from multiple events per multiple constructs that were evaluated for and determined to have significant cyst reduction against SCN when compared to the untransformed soybean cultivar. The number of plant roots tested was about equally distributed among the number of events tested.

Plates were incubated at 23-25° C. with a 16 hour light/8 hour dark cycle for 7-10 days. BCN eggs were placed on the sterile filter paper and hatched in 5 mM ZnSO4 solution for 5-7 days at 25° C. J2 stage juvenile nematodes were collected, rinsed in sterile water, and treated with 0.5% chlorhexidine diacetate for 10-15 minutes. Treated juvenile J2 nematodes were collected and rinsed twice in sterile water and stored in sterile water for infestation purposes.

For the infestation assay, about 10-15 *Arabidopsis* seeds were sprinkled on steamed sand in a pot and covered with a clear plastic dome. Several such dome/flat combos were placed in a flat and then covered with a black tray and transferred to a cold room for vernalization. On day 4, the flat was taken out of the cold room, the black tray is removed, and the flat was placed in a growth chamber for acclimating seeds at 26° C., 70% humidity, 140-180 μE light, 12 hours day length. The pots were watered and fertilized as needed. Three weeks after planting, the *Arabidopsis* plants were inoculated with 3,000 BCN eggs. About 35 days after inoculation the plants were harvested and cysts extracted by washing the plant's roots in a bucket of water and filtering the water through a 16 mesh sieve on top of a 50 mesh sieve. The cysts were collected off the top of the 50 mesh sieve and counted. Plants with lesser number of cysts compared to non-transgenic or transgenic control were considered resistant to BCN.

Table 2 reports data illustrating plants from multiple events per multiple constructs that were evaluated for and determined to have lesser number of BCN cysts compared to the untransformed *Arabidopsis* parental background. The number of plant roots tested was nearly equally distributed among the number of events tested.

TABLE 1

Severity of Soybean Cyst Nematode cyst infection on soybean plant roots

| Protein Name | SEQ ID NO: | Construct Name | Number of Events tested | Number of plant roots tested | Result (compared to control non-transgenic plants) |
|---|---|---|---|---|---|
| ET34 | 3 | 128213 | 14 | 177 | 1 of 14 events showed 35.4% cyst reduction |
| ET34 | 3 | 126168 | 15 | 389 | 7 of 15 events showed more than 46.7% cyst reduction |
| ET34 | 3 | 126626 | 15 | 191 | 0 of 15 events showed significant cyst reduction |
| ET34 | 3 | 126630 | 16 | 204 | 1 of 16 events showed 42.0% cyst reduction |
| ET34 | 3 | 127056 | 15 | 191 | 3 of 15 events showed more than 41.5% cyst reduction |
| ET34 | 3 | 128296 | 14 | 168 | 2 of 14 events showed more than 33% cyst reduction |
| P139 + ET34 | 7 | 126169 | 15 | 176 | 0 of 15 events showed the significant cyst reduction |
| P139 + ET34 | 7 | 126628 | 16 | 192 | 0 of 16 events showed the significant cyst reduction |
| TIC1501 | 15 | 133535 | 5 | 18 | 3 of 5 events showed more than 45% cyst reduction |

Example 7

Testing of Transgenic *Arabidopsis* Plant for Beet Cyst Nematode (BCN) Resistance Transgenic *Arabidopsis* seeds and plants comprising one or more of the polynucleotide sequences of SEQ ID NOs 3, 15, 27, 31, 35, 39, 43, 61, and 63 were produced by the method of Clough et al., 1998 (Plant J. 16:735-743) and tested for Beet Cyst Nematode (BCN) resistance by the method of Sijmons et al., 1991 (Plant J. 1: 245-254) and Vaghchhipawala et al., 2004 (Genome 47: 404-13).

*Arabidopsis* (variety Columbia-0) seeds were surface sterilized and rinsed with sterile water and plated on B5 medium.

TABLE 2

Severity of Beet Cyst Nematode cyst infection on *Arabidopsis thaliana* plant roots

| Protein Name | SEQ ID NO: | Construct Name | Number of Events tested | Number of plant roots tested | Resulting number of events having a lower mean cyst count compared to non-transgenic control |
|---|---|---|---|---|---|
| ET34 | 3 | 140057 | 6 | 72 | 3 |
| TIC1501 | 15 | 140056 | 6 | 72 | 3 |
| TIC615 | 27 | 139822 | 6 | 72 | 4 |
| TIC1277 | 31 | 142259 | 6 | 71 | 2 |
| TIC1278 | 35 | 141647 | 6 | 72 | 4 |

TABLE 2-continued

| Severity of Beet Cyst Nematode cyst infection on *Arabidopsis thaliana* plant roots | | | | | |
|---|---|---|---|---|---|
| Protein Name | SEQ ID NO: | Construct Name | Number of Events tested | Number of plant roots tested | Resulting number of events having a lower mean cyst count compared to non-transgenic control |
| TIC1310 | 39 | 142255 | 6 | 72 | 1 |
| TIC1311 | 43 | 141644 | 6 | 71 | 6 |
| TIC1308 | 61 | 141250 | 6 | 70 | 2 |
| TIC1422 | 63 | 141205 | 6 | 72 | 2 |

Various patent and non-patent publications are cited herein, the disclosures of each of which are incorporated herein by reference in their entireties. Documents cited herein as being available from the World Wide Web at certain internet addresses are also incorporated herein by reference in their entireties.

As various modifications could be made in the compositions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A DNA construct comprising a polynucleotide operably linked to a heterologous promoter, wherein said polynucleotide encodes a pesticidal polypeptide that comprises the amino acid sequence as set forth in SEQ ID NO:50.

2. The DNA construct of claim 1, wherein said polynucleotide is codon-optimized for expression in a plant.

3. The DNA construct of claim 2, wherein said polynucleotide comprises the nucleic acid sequence as set forth in SEQ ID NO:51.

4. A host cell comprising a DNA construct that comprises a polynucleotide operably linked to a heterologous promoter, wherein said polynucleotide encodes a pesticidal polypeptide that comprises the amino acid sequence as set forth in SEQ ID NO:50.

5. The host cell of claim 4, wherein said host cell is a bacterial cell or a plant cell.

6. The host cell of claim 5, wherein said bacterial cell is selected from the group consisting of an *Agrobacterium*, a *Bacillus*, an *Escherichia*, a *Salmonella*, a *Pseudomonas*, and a *Rhizobium* cell, and wherein said plant cell is selected from the group consisting of a alfalfa, banana, barley, bean, broccoli, cabbage, canola, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and a wheat plant cell.

7. A plant, or part thereof, comprising a polynucleotide encoding a pesticidal polypeptide that comprises the amino acid sequence as set forth in SEQ ID NO:50.

8. The plant, or part thereof, of claim 7, wherein said plant is elected from the group consisting of a alfalfa, banana, barley, bean, broccoli, cabbage, canola, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and a wheat plant, and wherein said part is selected from the group consisting of a leaf, a stem a flower, a sepal, a fruit, a root, or a seed.

9. A method of controlling a pest infection of a plant, said method comprising providing in a diet of said pest a plant, or part thereof, said plant or part comprising a polynucleotide encoding a pesticidal polypeptide that comprises the amino acid sequence as set forth in SEQ ID NO:50.

10. The method of claim 9, wherein said pest is an insect or a nematode.

11. The method of claim 10, wherein said insect is an insect from the insect order selected from the group consisting of Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, and Trichoptera, and wherein said nematode is selected from the group consisting of *Acontylus, Anguina, Aorolaimus, Aphasmatylenchus, Aphelenchoides, Aphelenchus, Atalodera, Atylenchus, Bakernema, Belonolaimus, Brachydorus, Bursaphelenchus, Cacopaurus, Caloosia, Carphodorus, Criconema, Criconemella, Cryphodera, Ditylenchus, Dolichodorus, Eutylenchus, Globodera, Gracilacus, Helicotylenchus, Hemicriconemoides, Hemicycliophora, Heterodera, Hirschmanniella, Histotylenchus, Hoplolaimus, Hoplotylus, Longidorus, Macrotrophurus, Meloidodera, Meloidogyne, Merlinius, Morulaimus, Nacobbus, Nothanguina, Nothotylenchus, Paralongidorus, Paratrichodorus, Paratrophurus, Paratylenchus, Peltamigratus, Pratylenchoides, Pratylenchus, Psilenchus, Radopholoides, Radopholus, Rhadinaphelenchus, Rototylenchus, Rotylenchoides, Rotylenchus, Sarisodera, Scutellonema, Sphaeronema, Subanguina, Telotylenchoides, Telotylenchus, Trichotylenchus, Trophonema, Trophotylenculus, Trophurus, Tylenchorhynchus, Tylenchulus, Tylenchus, Tylodorus, Xiphinema*, and *Zygotylenchus* nematode.

12. The method of claim 9, said method further comprising providing in the diet of said pest a pesticidally effective amount of one or more other toxic agents selected from the group consisting of methylketone synthase, a Cry protein, a VIP protein, and a chemical nematicide.

13. The method of claim 9, said method further comprising providing in a diet of said pest a pesticidally effective amount of one or more pesticidal polypeptides, wherein said one or more pesticidal polypeptides comprise SEQ ID NO:2, SEQ ID NO:6, SEQ ID NO:10, SEQ ID NO:14, SEQ ID NO:18, SEQ ID NO:22, SEQ ID NO:26, SEQ ID NO:30, SEQ ID NO:34, SEQ ID NO:38, SEQ ID NO:42, SEQ ID NO:46, SEQ ID NO:54, SEQ ID NO:58, or SEQ ID NO:60, or a pesticidal fragment thereof.

14. The method of claim 13, wherein the pesticidally effective amount of said one or more pesticidal polypeptides is provided by the plant, which is a recombinant plant, a part of the plant, or a product of the plant or the plant part.

15. The method of claim 13, wherein the pesticidally effective amount of said one or more pesticidal polypeptides is provided in one or more formulations topically applied on the plant or a part of the plant, said one or more formulations comprising bacterial cells, spores, or parasporal crystals that comprise said one or more pesticidal polypeptides.

* * * * *

SEQUENCE LISTING

```
<160> NUMBER OF SEQ ID NOS: 64

<210> SEQ ID NO 1
<211> LENGTH: 381
<212> TYPE: DNA
<213> ORGANISM: Bacillus thuringiensis

<400> SEQUENCE: 1

atgacagtat ataacgcaac tttcaccatt aatttctata atgaaggaga atgggggggg      60

ccagaaccat atggttatat aaaagcatat cttacaaatc cagatcatga ttttgaaatt     120

tggaaacaag atgattgggg gaaaagtact cctgagagaa gtacttatac gcaaacgatt     180

aaaataagta gcgacactgg ttcccctata aaccaaatgt gtttttatgg tgatgtgaaa     240

gaatacgacg taggaaatgc agatgatatt ctcgcttatc caagtcaaaa agtatgcagt     300

acacctggtg taacagtacg acttgatggc gatgagaaag gttcttatgt gacaattaag     360

tattccttga ctccagcata a                                               381


<210> SEQ ID NO 2
<211> LENGTH: 126
<212> TYPE: PRT
<213> ORGANISM: Bacillus thuringiensis

<400> SEQUENCE: 2

Met Thr Val Tyr Asn Ala Thr Phe Thr Ile Asn Phe Tyr Asn Glu Gly
1               5                   10                  15

Glu Trp Gly Gly Pro Glu Pro Tyr Gly Tyr Ile Lys Ala Tyr Leu Thr
            20                  25                  30

Asn Pro Asp His Asp Phe Glu Ile Trp Lys Gln Asp Asp Trp Gly Lys
        35                  40                  45

Ser Thr Pro Glu Arg Ser Thr Tyr Thr Gln Thr Ile Lys Ile Ser Ser
    50                  55                  60

Asp Thr Gly Ser Pro Ile Asn Gln Met Cys Phe Tyr Gly Asp Val Lys
65                  70                  75                  80

Glu Tyr Asp Val Gly Asn Ala Asp Asp Ile Leu Ala Tyr Pro Ser Gln
                85                  90                  95

Lys Val Cys Ser Thr Pro Gly Val Thr Val Arg Leu Asp Gly Asp Glu
            100                 105                 110

Lys Gly Ser Tyr Val Thr Ile Lys Tyr Ser Leu Thr Pro Ala
        115                 120                 125


<210> SEQ ID NO 3
<211> LENGTH: 381
```

<212> TYPE: DNA
<213> ORGANISM: Artificial sequence
<220> FEATURE:
<223> OTHER INFORMATION: recombinant polynucleotide encoding an ET34 protein.

<400> SEQUENCE: 3

```
atgactgttt acaacgctac tttcactatt aacttctaca acgagggtga gtggggtgga     60

cctgagcctt acggttacat taaggcttac ttgactaatc cagatcatga tttcgagatt    120

tggaagcaag atgattgggg caagagcact ccagagcgct ctacctacac ccaaaccatt    180

aagatttcat ccgataccgg atcacccatc aatcagatgt gcttctacgg agatgttaag    240

gagtatgatg ttggcaatgc tgacgacatc cttgcctatc cctcccagaa ggtctgtagt    300

acacccggcg tcacagtgag gctcgacggc gacgagaagg gttcctatgt aaccatcaag    360

tattcgctga cgcctgcatg a                                               381
```

<210> SEQ ID NO 4
<211> LENGTH: 126
<212> TYPE: PRT
<213> ORGANISM: Artificial sequence
<220> FEATURE:
<223> OTHER INFORMATION: an amino acid sequence translation of SEQ ID NO 3 from nucleotide position 1 through nucleotide position 378

<400> SEQUENCE: 4

```
Met Thr Val Tyr Asn Ala Thr Phe Thr Ile Asn Phe Tyr Asn Glu Gly
1               5                   10                  15

Glu Trp Gly Gly Pro Glu Pro Tyr Gly Tyr Ile Lys Ala Tyr Leu Thr
            20                  25                  30

Asn Pro Asp His Asp Phe Glu Ile Trp Lys Gln Asp Asp Trp Gly Lys
        35                  40                  45

Ser Thr Pro Glu Arg Ser Thr Tyr Thr Gln Thr Ile Lys Ile Ser Ser
    50                  55                  60

Asp Thr Gly Ser Pro Ile Asn Gln Met Cys Phe Tyr Gly Asp Val Lys
65                  70                  75                  80

Glu Tyr Asp Val Gly Asn Ala Asp Asp Ile Leu Ala Tyr Pro Ser Gln
                85                  90                  95

Lys Val Cys Ser Thr Pro Gly Val Thr Val Arg Leu Asp Gly Asp Glu
            100                 105                 110

Lys Gly Ser Tyr Val Thr Ile Lys Tyr Ser Leu Thr Pro Ala
        115                 120                 125
```

<210> SEQ ID NO 5
<211> LENGTH: 453
<212> TYPE: DNA
<213> ORGANISM: Artificial sequence
<220> FEATURE:
<223> OTHER INFORMATION: recombinant polynucleotide encoding a P139 secretion signal peptide (nucleotide position 1-75) fused in frame to a native Bt nucleotide sequence encoding a ET34 protein (nucleotide position 76-450)

<400> SEQUENCE: 5

```
atgaggagtt tcgccgtctt gttgccgctt ctcgtcacct tctgcgtggt ggcgcctcct     60

tccgacgccg ccaccacagt atataacgca actttcacca ttaatttcta taatgaagga    120

gaatgggggg ggccagaacc atatggttat ataaaagcat atcttacaaa tccagatcat    180

gattttgaaa tttggaaaca agatgattgg gggaaaagta ctcctgagag aagtacttat    240

acgcaaacga ttaaaataag tagcgacact ggttccccta taaaccaaat gtgtttttat    300
```

```
ggtgatgtga aagaatacga cgtaggaaat gcagatgata ttctcgctta tccaagtcaa    360

aaagtatgca gtacacctgg tgtaacagta cgacttgatg gcgatgagaa aggttcttat    420

gtgacaatta agtattcctt gactccagca taa                                 453


<210> SEQ ID NO 6
<211> LENGTH: 150
<212> TYPE: PRT
<213> ORGANISM: Artificial sequence
<220> FEATURE:
<223> OTHER INFORMATION: an amino acid sequence translation of SEQ ID
      NO: 5.

<400> SEQUENCE: 6

Met Arg Ser Phe Ala Val Leu Leu Pro Leu Leu Val Thr Phe Cys Val
1               5                   10                  15

Val Ala Pro Pro Ser Asp Ala Ala Thr Thr Val Tyr Asn Ala Thr Phe
            20                  25                  30

Thr Ile Asn Phe Tyr Asn Glu Gly Glu Trp Gly Gly Pro Glu Pro Tyr
        35                  40                  45

Gly Tyr Ile Lys Ala Tyr Leu Thr Asn Pro Asp His Asp Phe Glu Ile
    50                  55                  60

Trp Lys Gln Asp Asp Trp Gly Lys Ser Thr Pro Glu Arg Ser Thr Tyr
65                  70                  75                  80

Thr Gln Thr Ile Lys Ile Ser Ser Asp Thr Gly Ser Pro Ile Asn Gln
                85                  90                  95

Met Cys Phe Tyr Gly Asp Val Lys Glu Tyr Asp Val Gly Asn Ala Asp
            100                 105                 110

Asp Ile Leu Ala Tyr Pro Ser Gln Lys Val Cys Ser Thr Pro Gly Val
        115                 120                 125

Thr Val Arg Leu Asp Gly Asp Glu Lys Gly Ser Tyr Val Thr Ile Lys
    130                 135                 140

Tyr Ser Leu Thr Pro Ala
145                 150


<210> SEQ ID NO 7
<211> LENGTH: 453
<212> TYPE: DNA
<213> ORGANISM: Artificial sequence
<220> FEATURE:
<223> OTHER INFORMATION: a recombinant polynucleotide sequence encoding
      a P139 secretion signal peptide (nucleotide position 1-75) fused
      in frame to a synthetic nucleotide sequence encoding a ET34
      protein (nucleotide position 76-450)

<400> SEQUENCE: 7

atgaggagtt tcgccgtctt gttgccgctt ctcgtcacct tctgcgtggt ggcgcctcct     60

tccgacgccg ccaccactgt ttacaacgct actttcacta ttaacttcta caacgagggt    120

gagtggggtg gacctgagcc ttacggttac attaaggctt acttgactaa tccagatcat    180

gatttcgaga tttggaagca agatgattgg ggcaagagca ctccagagcg ctctacctac    240

acccaaacca ttaagatttc atccgatacc ggatcaccca tcaatcagat gtgcttctac    300

ggagatgtta aggagtatga tgttggcaat gctgacgaca tccttgccta tccctcccag    360

aaggtctgta gtacacccgg cgtcacagtg aggctcgacg gcgacgagaa gggttcctat    420

gtaaccatca agtattcgct gacgcctgca tga                                 453


<210> SEQ ID NO 8
```

<211> LENGTH: 150
<212> TYPE: PRT
<213> ORGANISM: Artificial sequence
<220> FEATURE:
<223> OTHER INFORMATION: an amino acid sequence translation of SEQ ID NO: 7.

<400> SEQUENCE: 8

```
Met Arg Ser Phe Ala Val Leu Leu Pro Leu Leu Val Thr Phe Cys Val
1               5                   10                  15

Val Ala Pro Pro Ser Asp Ala Ala Thr Thr Val Tyr Asn Ala Thr Phe
            20                  25                  30

Thr Ile Asn Phe Tyr Asn Glu Gly Glu Trp Gly Gly Pro Glu Pro Tyr
        35                  40                  45

Gly Tyr Ile Lys Ala Tyr Leu Thr Asn Pro Asp His Asp Phe Glu Ile
    50                  55                  60

Trp Lys Gln Asp Asp Trp Gly Lys Ser Thr Pro Glu Arg Ser Thr Tyr
65                  70                  75                  80

Thr Gln Thr Ile Lys Ile Ser Ser Asp Thr Gly Ser Pro Ile Asn Gln
                85                  90                  95

Met Cys Phe Tyr Gly Asp Val Lys Glu Tyr Asp Val Gly Asn Ala Asp
            100                 105                 110

Asp Ile Leu Ala Tyr Pro Ser Gln Lys Val Cys Ser Thr Pro Gly Val
        115                 120                 125

Thr Val Arg Leu Asp Gly Asp Glu Lys Gly Ser Tyr Val Thr Ile Lys
    130                 135                 140

Tyr Ser Leu Thr Pro Ala
145                 150
```

<210> SEQ ID NO 9
<211> LENGTH: 966
<212> TYPE: DNA
<213> ORGANISM: Bacillus thuringiensis

<400> SEQUENCE: 9

```
gcaataactc catatgctga atcttatatt gatactgttc aagatagaat gaaacaaaga     60

gatagggaat caaaactaac tggtaaacca ataaatatgc aagaacaaat aatagatgga    120

tggtttttag ctagattctg gatatttaaa gatcaaaata acaatcatca aacaaataga    180

tttatatcct ggtttaaaga taatcttgct agttcgaagg ggtatgacag tatagcagaa    240

caaatgggct taaaaataga agcattaaat gatatggatg taacaaatat tgattataca    300

tctaaaacag gtgataccat atataatgga atttctgaac taacaaatta tacaggaaca    360

acccaaaaaa tgaaaaccga tagttttcaa agagattata caaaatctga atccacttca    420

gtaacaaatg ggttacaatt aggatttaaa gttgctgcta agggagtagt tgcattagca    480

ggtgcagatt ttgaaacaag tgttacctat aatttatcat ctactacaac tgaaacaaat    540

acaatatcgg ataagtttac tgttccatct caagaagtta cattatcccc aggacataaa    600

gcagtggtga aacatgattt gagaaaaatg gtgtattttg ggactcatga tttaaagggt    660

gatttaaaag taggttttaa tgataaagag attgtacaaa aatttattta tccaaattat    720

agatcaattg atttatctga tattcgtaaa acaatgattg aaattgataa atggaatcat    780

gtaaatacca ttgactttta tcaattagtt ggagttaaaa atcatataaa aaatggtgat    840

actttatata tagatacccc ggccgaattt acatttaatg gagctaatcc atattataga    900

gcaacattta cagaatacga cgagaacgga aatcctgttc aaacaaagat tttaagtgga    960
```

-continued aattaa 966

<210> SEQ ID NO 10
<211> LENGTH: 321
<212> TYPE: PRT
<213> ORGANISM: Artificial sequence
<220> FEATURE:
<223> OTHER INFORMATION: an amino acid sequence translation of SEQ ID NO: 9.

<400> SEQUENCE: 10

```
Met Ile Thr Pro Tyr Ala Glu Ser Tyr Ile Asp Thr Val Gln Asp Arg
1               5                   10                  15

Met Lys Gln Arg Asp Arg Glu Ser Lys Leu Thr Gly Lys Pro Ile Asn
            20                  25                  30

Met Gln Glu Gln Ile Ile Asp Gly Trp Phe Leu Ala Arg Phe Trp Ile
        35                  40                  45

Phe Lys Asp Gln Asn Asn Asn His Gln Thr Asn Arg Phe Ile Ser Trp
    50                  55                  60

Phe Lys Asp Asn Leu Ala Ser Ser Lys Gly Tyr Asp Ser Ile Ala Glu
65                  70                  75                  80

Gln Met Gly Leu Lys Ile Glu Ala Leu Asn Asp Met Asp Val Thr Asn
                85                  90                  95

Ile Asp Tyr Thr Ser Lys Thr Gly Asp Thr Ile Tyr Asn Gly Ile Ser
            100                 105                 110

Glu Leu Thr Asn Tyr Thr Gly Thr Thr Gln Lys Met Lys Thr Asp Ser
        115                 120                 125

Phe Gln Arg Asp Tyr Thr Lys Ser Glu Ser Thr Ser Val Thr Asn Gly
    130                 135                 140

Leu Gln Leu Gly Phe Lys Val Ala Ala Lys Gly Val Val Ala Leu Ala
145                 150                 155                 160

Gly Ala Asp Phe Glu Thr Ser Val Thr Tyr Asn Leu Ser Ser Thr Thr
                165                 170                 175

Thr Glu Thr Asn Thr Ile Ser Asp Lys Phe Thr Val Pro Ser Gln Glu
            180                 185                 190

Val Thr Leu Ser Pro Gly His Lys Ala Val Val Lys His Asp Leu Arg
        195                 200                 205

Lys Met Val Tyr Phe Gly Thr His Asp Leu Lys Gly Asp Leu Lys Val
    210                 215                 220

Gly Phe Asn Asp Lys Glu Ile Val Gln Lys Phe Ile Tyr Pro Asn Tyr
225                 230                 235                 240

Arg Ser Ile Asp Leu Ser Asp Ile Arg Lys Thr Met Ile Glu Ile Asp
                245                 250                 255

Lys Trp Asn His Val Asn Thr Ile Asp Phe Tyr Gln Leu Val Gly Val
            260                 265                 270

Lys Asn His Ile Lys Asn Gly Asp Thr Leu Tyr Ile Asp Thr Pro Ala
        275                 280                 285

Glu Phe Thr Phe Asn Gly Ala Asn Pro Tyr Tyr Arg Ala Thr Phe Thr
    290                 295                 300

Glu Tyr Asp Glu Asn Gly Asn Pro Val Gln Thr Lys Ile Leu Ser Gly
305                 310                 315                 320

Asn
```

<210> SEQ ID NO 11
<211> LENGTH: 966
<212> TYPE: DNA

-continued

<213> ORGANISM: Artificial sequence
<220> FEATURE:
<223> OTHER INFORMATION: recombinant polynucleotide encoding a TIC1506
      protein.

<400> SEQUENCE: 11

```
atgattactc cttacgctga gtcttacatt gatactgttc aagatcgcat gaagcaacgt     60

gatcgtgagt ctaagttgac tggcaagcct attaacatgc aagagcaaat tatcgacggt    120

tggttcctag ccagattctg gatcttcaag gatcagaaca ataaccacca gaccaaccgc    180

ttcatcagtt ggttcaagga taacttggct agttctaagg gttacgatag tattgctgag    240

caaatgggtt tgaagattga ggctttgaac gatatggatg ttaccaacat tgattacact    300

tccaagactg gtgatacgat ctacaacggt atttctgagt tgactaacta cactggtact    360

actcagaaga tgaagaccga cagcttccag agggattaca ccaagtctga gtcaacctca    420

gttaccaacg gacttcagct tggattcaag gttgcagcca agggagttgt ggcacttgct    480

ggagcagatt tcgagacctc agttacctac aacctttcat ccaccacaac cgaaacgaac    540

accatctccg ataagtttac cgttccatcc caggaagtga cactttcccc aggacacaag    600

gccgtggtca agcacgatct caggaagatg gtgtacttcg gaacacacga cctcaaaggc    660

gacctcaaag tgggctttaa cgacaaagaa atcgtgcaga agttcatcta tccaaattat    720

cgcagcatcg acctcagcga catccgaaag acaatgatcg aaatcgacaa atggaatcac    780

gtcaacacaa tcgacttcta tcaactggtc ggcgtaaaga accacatcaa gaacggcgac    840

acactctaca tcgacacacc cgccgagttt acattcaatg gggccaatcc ctattatcgg    900

gcgacattca cggaatacga cgagaatggg aatccggtac agacgaagat cctgtcgggg    960

aattga                                                               966
```

<210> SEQ ID NO 12
<211> LENGTH: 321
<212> TYPE: PRT
<213> ORGANISM: Artificial sequence
<220> FEATURE:
<223> OTHER INFORMATION: an amino acid sequence translation of SEQ ID
      NO: 11.

<400> SEQUENCE: 12

```
Met Ile Thr Pro Tyr Ala Glu Ser Tyr Ile Asp Thr Val Gln Asp Arg
1               5                   10                  15

Met Lys Gln Arg Asp Arg Glu Ser Lys Leu Thr Gly Lys Pro Ile Asn
            20                  25                  30

Met Gln Glu Gln Ile Ile Asp Gly Trp Phe Leu Ala Arg Phe Trp Ile
        35                  40                  45

Phe Lys Asp Gln Asn Asn Asn His Gln Thr Asn Arg Phe Ile Ser Trp
    50                  55                  60

Phe Lys Asp Asn Leu Ala Ser Ser Lys Gly Tyr Asp Ser Ile Ala Glu
65                  70                  75                  80

Gln Met Gly Leu Lys Ile Glu Ala Leu Asn Asp Met Asp Val Thr Asn
                85                  90                  95

Ile Asp Tyr Thr Ser Lys Thr Gly Asp Thr Ile Tyr Asn Gly Ile Ser
            100                 105                 110

Glu Leu Thr Asn Tyr Thr Gly Thr Thr Gln Lys Met Lys Thr Asp Ser
        115                 120                 125

Phe Gln Arg Asp Tyr Thr Lys Ser Glu Ser Thr Ser Val Thr Asn Gly
    130                 135                 140
```

-continued

```
Leu Gln Leu Gly Phe Lys Val Ala Ala Lys Gly Val Val Ala Leu Ala
145                 150                 155                 160

Gly Ala Asp Phe Glu Thr Ser Val Thr Tyr Asn Leu Ser Ser Thr Thr
                165                 170                 175

Thr Glu Thr Asn Thr Ile Ser Asp Lys Phe Thr Val Pro Ser Gln Glu
            180                 185                 190

Val Thr Leu Ser Pro Gly His Lys Ala Val Val Lys His Asp Leu Arg
        195                 200                 205

Lys Met Val Tyr Phe Gly Thr His Asp Leu Lys Gly Asp Leu Lys Val
    210                 215                 220

Gly Phe Asn Asp Lys Glu Ile Val Gln Lys Phe Ile Tyr Pro Asn Tyr
225                 230                 235                 240

Arg Ser Ile Asp Leu Ser Asp Ile Arg Lys Thr Met Ile Glu Ile Asp
                245                 250                 255

Lys Trp Asn His Val Asn Thr Ile Asp Phe Tyr Gln Leu Val Gly Val
            260                 265                 270

Lys Asn His Ile Lys Asn Gly Asp Thr Leu Tyr Ile Asp Thr Pro Ala
        275                 280                 285

Glu Phe Thr Phe Asn Gly Ala Asn Pro Tyr Tyr Arg Ala Thr Phe Thr
    290                 295                 300

Glu Tyr Asp Glu Asn Gly Asn Pro Val Gln Thr Lys Ile Leu Ser Gly
305                 310                 315                 320

Asn


<210> SEQ ID NO 13
<211> LENGTH: 681
<212> TYPE: DNA
<213> ORGANISM: Bacillus thuringiensis

<400> SEQUENCE: 13

gcaataactc catatgctga atcttatatt gatactgttc aagatagaat gaaacaaaga     60

gatagggaat caaaactaac tggtaaacca ataaatatgc aagaacaaat aatagatgga    120

tggtttttag ctagattctg gatatttaaa gatcaaaata acaatcatca aacaaataga    180

tttatatcct ggtttaaaga taatcttgct agttcgaagg ggtatgacag tatagcagaa    240

caaatgggct taaaaataga agcattaaat gatatggatg taacaaatat tgattataca    300

tctaaaacag gtgataccat atataatgga atttctgaac taacaaatta tacaggaaca    360

acccaaaaaa tgaaaaccga tagttttcaa agagattata caaaatctga atccacttca    420

gtaacaaatg ggttacaatt aggatttaaa gttgctgcta agggagtagt tgcattagca    480

ggtgcagatt ttgaaacaag tgttacctat aatttatcat ctactacaac tgaaacaaat    540

acaatatcgg ataagtttac tgttccatct caagaagtta cattatcccc aggacataaa    600

gcagtggtga aacatgattt gagaaaaatg gtgtattttg ggactcatga tttaaagggt    660

gatttaaaag taggttttaa t                                              681


<210> SEQ ID NO 14
<211> LENGTH: 227
<212> TYPE: PRT
<213> ORGANISM: Artificial sequence
<220> FEATURE:
<223> OTHER INFORMATION: an amino acid sequence translation of SEQ ID
      NO: 13.

<400> SEQUENCE: 14

Met Ile Thr Pro Tyr Ala Glu Ser Tyr Ile Asp Thr Val Gln Asp Arg
```

-continued

```
1               5                   10                  15

Met Lys Gln Arg Asp Arg Glu Ser Lys Leu Thr Gly Lys Pro Ile Asn
            20                  25                  30

Met Gln Glu Gln Ile Ile Asp Gly Trp Phe Leu Ala Arg Phe Trp Ile
        35                  40                  45

Phe Lys Asp Gln Asn Asn Asn His Gln Thr Asn Arg Phe Ile Ser Trp
    50                  55                  60

Phe Lys Asp Asn Leu Ala Ser Ser Lys Gly Tyr Asp Ser Ile Ala Glu
65                  70                  75                  80

Gln Met Gly Leu Lys Ile Glu Ala Leu Asn Asp Met Asp Val Thr Asn
                85                  90                  95

Ile Asp Tyr Thr Ser Lys Thr Gly Asp Thr Ile Tyr Asn Gly Ile Ser
            100                 105                 110

Glu Leu Thr Asn Tyr Thr Gly Thr Thr Gln Lys Met Lys Thr Asp Ser
        115                 120                 125

Phe Gln Arg Asp Tyr Thr Lys Ser Glu Ser Thr Ser Val Thr Asn Gly
    130                 135                 140

Leu Gln Leu Gly Phe Lys Val Ala Ala Lys Gly Val Val Ala Leu Ala
145                 150                 155                 160

Gly Ala Asp Phe Glu Thr Ser Val Thr Tyr Asn Leu Ser Ser Thr Thr
                165                 170                 175

Thr Glu Thr Asn Thr Ile Ser Asp Lys Phe Thr Val Pro Ser Gln Glu
            180                 185                 190

Val Thr Leu Ser Pro Gly His Lys Ala Val Val Lys His Asp Leu Arg
        195                 200                 205

Lys Met Val Tyr Phe Gly Thr His Asp Leu Lys Gly Asp Leu Lys Val
    210                 215                 220

Gly Phe Asn
225
```

<210> SEQ ID NO 15
<211> LENGTH: 684
<212> TYPE: DNA
<213> ORGANISM: Artificial sequence
<220> FEATURE:
<223> OTHER INFORMATION: a recombinant polynucleotide sequence encoding a TIC1501 protein.

<400> SEQUENCE: 15

```
atgattactc cttacgctga gtcttacatt gatactgttc aagatcgcat gaagcaacgt     60

gatcgtgagt ctaagttgac tggcaagcct attaacatgc aagagcaaat tatcgacggt    120

tggttcctag ccagattctg gatcttcaag gatcagaaca ataaccacca gaccaaccgc    180

ttcatcagtt ggttcaagga taacttggct agttctaagg gttacgatag tattgctgag    240

caaatgggtt tgaagattga ggctttgaac gatatggatg ttaccaacat tgattacact    300

tccaagactg gtgatacgat ctacaacggt atttctgagt tgactaacta cactggtact    360

actcagaaga tgaagaccga cagcttccag agggattaca ccaagtctga gtcaacctca    420

gttaccaacg gacttcagct tggattcaag gttgcagcca agggagttgt ggcacttgct    480

ggagcagatt tcgagacctc agttacctac aacctttcat ccaccacaac cgaaacgaac    540

accatctccg ataagtttac cgttccatcc caggaagtga cactttcccc aggacacaag    600

gccgtggtca agcacgatct caggaagatg gtgtacttcg gaacacacga cctcaaaggc    660

gacctcaaag tgggctttaa ctga                                           684
```

<210> SEQ ID NO 16
<211> LENGTH: 227
<212> TYPE: PRT
<213> ORGANISM: Artificial sequence
<220> FEATURE:
<223> OTHER INFORMATION: an amino acid sequence translation of SEQ ID NO: 15.

<400> SEQUENCE: 16

```
Met Ile Thr Pro Tyr Ala Glu Ser Tyr Ile Asp Thr Val Gln Asp Arg
1               5                   10                  15

Met Lys Gln Arg Asp Arg Glu Ser Lys Leu Thr Gly Lys Pro Ile Asn
            20                  25                  30

Met Gln Glu Gln Ile Ile Asp Gly Trp Phe Leu Ala Arg Phe Trp Ile
        35                  40                  45

Phe Lys Asp Gln Asn Asn Asn His Gln Thr Asn Arg Phe Ile Ser Trp
    50                  55                  60

Phe Lys Asp Asn Leu Ala Ser Ser Lys Gly Tyr Asp Ser Ile Ala Glu
65                  70                  75                  80

Gln Met Gly Leu Lys Ile Glu Ala Leu Asn Asp Met Asp Val Thr Asn
                85                  90                  95

Ile Asp Tyr Thr Ser Lys Thr Gly Asp Thr Ile Tyr Asn Gly Ile Ser
            100                 105                 110

Glu Leu Thr Asn Tyr Thr Gly Thr Thr Gln Lys Met Lys Thr Asp Ser
        115                 120                 125

Phe Gln Arg Asp Tyr Thr Lys Ser Glu Ser Thr Ser Val Thr Asn Gly
    130                 135                 140

Leu Gln Leu Gly Phe Lys Val Ala Ala Lys Gly Val Val Ala Leu Ala
145                 150                 155                 160

Gly Ala Asp Phe Glu Thr Ser Val Thr Tyr Asn Leu Ser Ser Thr Thr
                165                 170                 175

Thr Glu Thr Asn Thr Ile Ser Asp Lys Phe Thr Val Pro Ser Gln Glu
            180                 185                 190

Val Thr Leu Ser Pro Gly His Lys Ala Val Val Lys His Asp Leu Arg
        195                 200                 205

Lys Met Val Tyr Phe Gly Thr His Asp Leu Lys Gly Asp Leu Lys Val
    210                 215                 220

Gly Phe Asn
225
```

<210> SEQ ID NO 17
<211> LENGTH: 903
<212> TYPE: DNA
<213> ORGANISM: Bacillus thuringiensis

<400> SEQUENCE: 17

```
gcaataactc catatgctga atcttatatt gatactgttc aagatagaat gaaacaaaga     60

gatagggaat caaaactaac tggtaaacca ataaatatgc aagaacaaat aatagatgga    120

tggtttttag ctagattctg gatatttaaa gatcaaaata acaatcatca aacaaataga    180

tttatatcct ggtttaaaga taatcttgct agttcgaagg ggtatgacag tatagcagaa    240

caaatgggct taaaaataga agcattaaat gatatggatg taacaaatat tgattataca    300

tctaaaacag gtgataccat atataatgga atttctgaac taacaaatta tacaggaaca    360

acccaaaaaa tgaaaaccga tagttttcaa agagattata caaaatctga atccacttca    420

gtaacaaatg ggttacaatt aggatttaaa gttgctgcta agggagtagt tgcattagca    480
```

-continued ggtgcagatt ttgaaacaag tgttacctat aatttatcat ctactacaac tgaaacaaat 540
acaatatcgg ataagtttac tgttccatct caagaagtta cattatcccc aggacataaa 600
gcagtggtga aacatgattt gagaaaaatg gtgtattttg ggactcatga tttaaagggt 660
gatttaaaag taggttttaa tgataaagag attgtacaaa aatttattta tccaaattat 720
agatcaattg atttatctga tattcgtaaa acaatgattg aaattgataa atggaatcat 780
gtaaatacca ttgactttta tcaattagtt ggagttaaaa atcatataaa aaatggtgat 840
actttatata tagatacccc ggccgaattt acatttaatg gagctaatcc atattataga 900
gca 903

<210> SEQ ID NO 18
<211> LENGTH: 301
<212> TYPE: PRT
<213> ORGANISM: Artificial sequence
<220> FEATURE:
<223> OTHER INFORMATION: an amino acid sequence translation of SEQ ID
NO: 17.

<400> SEQUENCE: 18

Met Ile Thr Pro Tyr Ala Glu Ser Tyr Ile Asp Thr Val Gln Asp Arg
1 5 10 15

Met Lys Gln Arg Asp Arg Glu Ser Lys Leu Thr Gly Lys Pro Ile Asn
20 25 30

Met Gln Glu Gln Ile Ile Asp Gly Trp Phe Leu Ala Arg Phe Trp Ile
35 40 45

Phe Lys Asp Gln Asn Asn Asn His Gln Thr Asn Arg Phe Ile Ser Trp
50 55 60

Phe Lys Asp Asn Leu Ala Ser Ser Lys Gly Tyr Asp Ser Ile Ala Glu
65 70 75 80

Gln Met Gly Leu Lys Ile Glu Ala Leu Asn Asp Met Asp Val Thr Asn
85 90 95

Ile Asp Tyr Thr Ser Lys Thr Gly Asp Thr Ile Tyr Asn Gly Ile Ser
100 105 110

Glu Leu Thr Asn Tyr Thr Gly Thr Thr Gln Lys Met Lys Thr Asp Ser
115 120 125

Phe Gln Arg Asp Tyr Thr Lys Ser Glu Ser Thr Ser Val Thr Asn Gly
130 135 140

Leu Gln Leu Gly Phe Lys Val Ala Ala Lys Gly Val Val Ala Leu Ala
145 150 155 160

Gly Ala Asp Phe Glu Thr Ser Val Thr Tyr Asn Leu Ser Ser Thr Thr
165 170 175

Thr Glu Thr Asn Thr Ile Ser Asp Lys Phe Thr Val Pro Ser Gln Glu
180 185 190

Val Thr Leu Ser Pro Gly His Lys Ala Val Val Lys His Asp Leu Arg
195 200 205

Lys Met Val Tyr Phe Gly Thr His Asp Leu Lys Gly Asp Leu Lys Val
210 215 220

Gly Phe Asn Asp Lys Glu Ile Val Gln Lys Phe Ile Tyr Pro Asn Tyr
225 230 235 240

Arg Ser Ile Asp Leu Ser Asp Ile Arg Lys Thr Met Ile Glu Ile Asp
245 250 255

Lys Trp Asn His Val Asn Thr Ile Asp Phe Tyr Gln Leu Val Gly Val
260 265 270

-continued

```
Lys Asn His Ile Lys Asn Gly Asp Thr Leu Tyr Ile Asp Thr Pro Ala
        275                 280                 285

Glu Phe Thr Phe Asn Gly Ala Asn Pro Tyr Tyr Arg Ala
    290                 295                 300


<210> SEQ ID NO 19
<211> LENGTH: 906
<212> TYPE: DNA
<213> ORGANISM: Artificial sequence
<220> FEATURE:
<223> OTHER INFORMATION: a recombinant polynucleotide sequence encoding
      a TIC1503 protein.

<400> SEQUENCE: 19

atgattactc cttacgctga gtcttacatt gatactgttc aagatcgcat gaagcaacgt      60

gatcgtgagt ctaagttgac tggcaagcct attaacatgc aagagcaaat tatcgacggt     120

tggttcctag ccagattctg gatcttcaag gatcagaaca ataaccacca gaccaaccgc     180

ttcatcagtt ggttcaagga taacttggct agttctaagg gttacgatag tattgctgag     240

caaatgggtt tgaagattga ggctttgaac gatatggatg ttaccaacat tgattacact     300

tccaagactg gtgatacgat ctacaacggt atttctgagt tgactaacta cactggtact     360

actcagaaga tgaagaccga cagcttccag agggattaca ccaagtctga gtcaacctca     420

gttaccaacg gacttcagct tggattcaag gttgcagcca agggagttgt ggcacttgct     480

ggagcagatt tcgagacctc agttacctac aacctttcat ccaccacaac cgaaacgaac     540

accatctccg ataagtttac cgttccatcc caggaagtga cactttcccc aggacacaag     600

gccgtggtca agcacgatct caggaagatg gtgtacttcg gaacacacga cctcaaaggc     660

gacctcaaag tgggctttaa cgacaaagaa atcgtgcaga agttcatcta tccaaattat     720

cgcagcatcg acctcagcga catccgaaag acaatgatcg aaatcgacaa atggaatcac     780

gtcaacacaa tcgacttcta tcaactggtc ggcgtaaaga accacatcaa gaacggcgac     840

acactctaca tcgacacacc cgccgagttt acattcaatg gggccaatcc ctattatcgg     900

gcgtga                                                                906


<210> SEQ ID NO 20
<211> LENGTH: 301
<212> TYPE: PRT
<213> ORGANISM: Artificial sequence
<220> FEATURE:
<223> OTHER INFORMATION: an amino acid sequence translation of SEQ ID
      NO: 19.

<400> SEQUENCE: 20

Met Ile Thr Pro Tyr Ala Glu Ser Tyr Ile Asp Thr Val Gln Asp Arg
1               5                   10                  15

Met Lys Gln Arg Asp Arg Glu Ser Lys Leu Thr Gly Lys Pro Ile Asn
            20                  25                  30

Met Gln Glu Gln Ile Ile Asp Gly Trp Phe Leu Ala Arg Phe Trp Ile
        35                  40                  45

Phe Lys Asp Gln Asn Asn Asn His Gln Thr Asn Arg Phe Ile Ser Trp
    50                  55                  60

Phe Lys Asp Asn Leu Ala Ser Ser Lys Gly Tyr Asp Ser Ile Ala Glu
65                  70                  75                  80

Gln Met Gly Leu Lys Ile Glu Ala Leu Asn Asp Met Asp Val Thr Asn
                85                  90                  95

Ile Asp Tyr Thr Ser Lys Thr Gly Asp Thr Ile Tyr Asn Gly Ile Ser
```

-continued

```
            100                 105                 110

Glu Leu Thr Asn Tyr Thr Gly Thr Thr Gln Lys Met Lys Thr Asp Ser
        115                 120                 125

Phe Gln Arg Asp Tyr Thr Lys Ser Glu Ser Thr Ser Val Thr Asn Gly
    130                 135                 140

Leu Gln Leu Gly Phe Lys Val Ala Ala Lys Gly Val Val Ala Leu Ala
145                 150                 155                 160

Gly Ala Asp Phe Glu Thr Ser Val Thr Tyr Asn Leu Ser Ser Thr Thr
                165                 170                 175

Thr Glu Thr Asn Thr Ile Ser Asp Lys Phe Thr Val Pro Ser Gln Glu
            180                 185                 190

Val Thr Leu Ser Pro Gly His Lys Ala Val Val Lys His Asp Leu Arg
        195                 200                 205

Lys Met Val Tyr Phe Gly Thr His Asp Leu Lys Gly Asp Leu Lys Val
    210                 215                 220

Gly Phe Asn Asp Lys Glu Ile Val Gln Lys Phe Ile Tyr Pro Asn Tyr
225                 230                 235                 240

Arg Ser Ile Asp Leu Ser Asp Ile Arg Lys Thr Met Ile Glu Ile Asp
                245                 250                 255

Lys Trp Asn His Val Asn Thr Ile Asp Phe Tyr Gln Leu Val Gly Val
            260                 265                 270

Lys Asn His Ile Lys Asn Gly Asp Thr Leu Tyr Ile Asp Thr Pro Ala
        275                 280                 285

Glu Phe Thr Phe Asn Gly Ala Asn Pro Tyr Tyr Arg Ala
    290                 295                 300
```

<210> SEQ ID NO 21
<211> LENGTH: 774
<212> TYPE: DNA
<213> ORGANISM: Bacillus thuringiensis

<400> SEQUENCE: 21

```
atggacattc aagatgtaat agaattaatt agtgactatg ccaacaagtg gaaggaacaa      60

caaaatggaa gtcgtagtga catgaaattc attgatgcac gctttgcgaa caatgcatta     120

aaagtagaag ctgatcgtac tatgtacctg gagcctacag agcaagatat gccagatgta     180

aaattagata cccaagtgtt taccaatact tccacacagc ccaaaaactgt ccagtttgat     240

atgtttggag aatacgatac ttggcaaaca tggagaatcg aagatggtgc aacagaagca     300

ggaaaatgtc gctttgccat tgagccattg tttagatcag aggatgtttc tagtccacta     360

tctttatttt taaacgacac acttaccctc tcagggaaaa agccattttc cgttgagggt     420

cgtgatttta cagttcgacc acgtttcaaa gtaacgggta cactcatggc aaaacccaaa     480

acatcaaccc gtgcttttga cgtaaaacgt gacgtcacag gatatgtggg acttgtcaca     540

actttagcat ccggagaact gcaagaatcg ttacacaatg tgggcgctat tttccaacaa     600

tattatagtc cctatatcga agtaaatggt ggaagagtga catttcatga tcgtggtgaa     660

tatcaatcat tagatgtaag cagcatctat attcatattt ttgcagagag cttagatatt     720

cccggattaa cggaggaata taatatttat gacctaagca atggacgggt ataa           774
```

<210> SEQ ID NO 22
<211> LENGTH: 257
<212> TYPE: PRT
<213> ORGANISM: Bacillus thuringiensis

<400> SEQUENCE: 22

```
Met Asp Ile Gln Asp Val Ile Glu Leu Ile Ser Asp Tyr Ala Asn Lys
1               5                   10                  15

Trp Lys Glu Gln Gln Asn Gly Ser Arg Ser Asp Met Lys Phe Ile Asp
            20                  25                  30

Ala Arg Phe Ala Asn Asn Ala Leu Lys Val Glu Ala Asp Arg Thr Met
        35                  40                  45

Tyr Leu Glu Pro Thr Glu Gln Asp Met Pro Asp Val Lys Leu Asp Thr
    50                  55                  60

Gln Val Phe Thr Asn Thr Ser Thr Gln Pro Lys Thr Val Gln Phe Asp
65                  70                  75                  80

Met Phe Gly Glu Tyr Asp Thr Trp Gln Thr Trp Arg Ile Glu Asp Gly
                85                  90                  95

Ala Thr Glu Ala Gly Lys Cys Arg Phe Ala Ile Glu Pro Leu Phe Arg
            100                 105                 110

Ser Glu Asp Val Ser Ser Pro Leu Ser Leu Phe Leu Asn Asp Thr Leu
        115                 120                 125

Thr Leu Ser Gly Lys Lys Pro Phe Ser Val Glu Gly Arg Asp Phe Thr
    130                 135                 140

Val Arg Pro Arg Phe Lys Val Thr Gly Thr Leu Met Ala Lys Pro Lys
145                 150                 155                 160

Thr Ser Thr Arg Ala Phe Asp Val Lys Arg Asp Val Thr Gly Tyr Val
                165                 170                 175

Gly Leu Val Thr Thr Leu Ala Ser Gly Glu Leu Gln Glu Ser Leu His
            180                 185                 190

Asn Val Gly Ala Ile Phe Gln Gln Tyr Tyr Ser Pro Tyr Ile Glu Val
        195                 200                 205

Asn Gly Gly Arg Val Thr Phe His Asp Arg Gly Glu Tyr Gln Ser Leu
    210                 215                 220

Asp Val Ser Ser Ile Tyr Ile His Ile Phe Ala Glu Ser Leu Asp Ile
225                 230                 235                 240

Pro Gly Leu Thr Glu Glu Tyr Asn Ile Tyr Asp Leu Ser Asn Gly Arg
                245                 250                 255

Val
```

<210> SEQ ID NO 23
<211> LENGTH: 774
<212> TYPE: DNA
<213> ORGANISM: Artificial sequence
<220> FEATURE:
<223> OTHER INFORMATION: Synthetic

<400> SEQUENCE: 23

```
atggacattc aagatgtgat tgagttgatt tctgattacg ccaacaagtg gaaggagcaa      60

cagaacggta gtcgtagtga catgaagttc attgatgctc gcttcgccaa caacgctttg     120

aaggttgagg ctgatcgcac tatgtaccta gagcctactg agcaagacat gcctgatgtt     180

aagttggata ctcaagtgtt cacgaacacc agtacccaac ctaagactgt tcagttcgac     240

atgttcggtg agtacgatac ctggcagacc tggagaattg aggatggtgc taccgaggcg     300

ggcaagtgca gattcgcaat tgagccattg ttccgctctg aggatgtttc ttcaccactt     360

tctctcttcc ttaatgacac ccttaccctt tctggtaaga aaccattcag cgttgaagga     420

agggacttta ccgtgaggcc aaggtttaaa gtgaccggaa cactcatggc caaacccaag     480

acttcaaccc gtgcctttga cgtgaaacgc gacgtgacag gatacgtggg actcgtgaca     540
```

-continued

```
acgctcgcct caggagaact ccaggaatca ctgcacaatg tcggtgccat ctttcagcag    600

tactacagcc cctacatcga agtcaatggc gggcgcgtca cattccatga ccgaggcgag    660

tatcagtccc tagacgtatc cagcatctac atccacatct ttgcggaaag cctcgacata    720

cctgggctca cggaggagta caacatctac gacctgtcga atgggcgggt atga          774
```

```
<210> SEQ ID NO 24
<211> LENGTH: 257
<212> TYPE: PRT
<213> ORGANISM: Artificial sequence
<220> FEATURE:
<223> OTHER INFORMATION: Synthetic

<400> SEQUENCE: 24

Met Asp Ile Gln Asp Val Ile Glu Leu Ile Ser Asp Tyr Ala Asn Lys
1               5                   10                  15

Trp Lys Glu Gln Gln Asn Gly Ser Arg Ser Asp Met Lys Phe Ile Asp
            20                  25                  30

Ala Arg Phe Ala Asn Asn Ala Leu Lys Val Glu Ala Asp Arg Thr Met
        35                  40                  45

Tyr Leu Glu Pro Thr Glu Gln Asp Met Pro Asp Val Lys Leu Asp Thr
    50                  55                  60

Gln Val Phe Thr Asn Thr Ser Thr Gln Pro Lys Thr Val Gln Phe Asp
65                  70                  75                  80

Met Phe Gly Glu Tyr Asp Thr Trp Gln Thr Trp Arg Ile Glu Asp Gly
                85                  90                  95

Ala Thr Glu Ala Gly Lys Cys Arg Phe Ala Ile Glu Pro Leu Phe Arg
            100                 105                 110

Ser Glu Asp Val Ser Ser Pro Leu Ser Leu Phe Leu Asn Asp Thr Leu
        115                 120                 125

Thr Leu Ser Gly Lys Lys Pro Phe Ser Val Glu Gly Arg Asp Phe Thr
    130                 135                 140

Val Arg Pro Arg Phe Lys Val Thr Gly Thr Leu Met Ala Lys Pro Lys
145                 150                 155                 160

Thr Ser Thr Arg Ala Phe Asp Val Lys Arg Asp Val Thr Gly Tyr Val
                165                 170                 175

Gly Leu Val Thr Thr Leu Ala Ser Gly Glu Leu Gln Glu Ser Leu His
            180                 185                 190

Asn Val Gly Ala Ile Phe Gln Gln Tyr Tyr Ser Pro Tyr Ile Glu Val
        195                 200                 205

Asn Gly Gly Arg Val Thr Phe His Asp Arg Gly Glu Tyr Gln Ser Leu
    210                 215                 220

Asp Val Ser Ser Ile Tyr Ile His Ile Phe Ala Glu Ser Leu Asp Ile
225                 230                 235                 240

Pro Gly Leu Thr Glu Glu Tyr Asn Ile Tyr Asp Leu Ser Asn Gly Arg
                245                 250                 255

Val
```

```
<210> SEQ ID NO 25
<211> LENGTH: 900
<212> TYPE: DNA
<213> ORGANISM: Bacillus thuringiensis

<400> SEQUENCE: 25

atggctattt ttaattttga cgcaaaagta gtagagttta ttaattggtg gacagcagag     60

ttcggtggca aagatcccag aaatattcaa attggttatg agaatcgaga catcaatgtt    120
```

-continued

```
gttccatcat caagtaaccc tagtgtcaat gtaataccta agttagcaag atcatctgtt    180

caagaattgc aaaataatac aagtgtaacg cagacacaag agctggcatt ttcagaaact    240

acaactgaaa gtcagtcttc tacaacaaca catggggctt cattttctac aacggtcacc    300

tctgttacgc aatttacagc tgaagttaat ttcaaagcga ttggttcctc aattgagcaa    360

actatcggcg tttctatgac aggagattat aattacagtt cttcactaac aaaaacaaca    420

gaaaagagta gatcttggac tctcacacaa ccggtagttg tcccaccttt ttcacgtgta    480

acttgcacat tattgatata taatgcacca ttttcagtac ctgtggactt aaattgtaat    540

gtattcggta cacttggcgg agatttttta gctagctaca cttacactgt tattagtact    600

ggtcgaacag taaatactag tataactgct agtcaaatga ctcttacctc ttggccaggt    660

aaaccatctg aaattattgg tatcgcacca aagcatggac ttatttttaa agggacaggt    720

acacaggctg cagtacatgg attatactca accgttaaat ttgttgaatc cccattgcca    780

ggtcaccaag gagaaaaaag aacgtattac cttccagcgc aacctgtaaa tgaagatgat    840

ctgatttctt ctgtatttag taacattcca attattaatc ctgtttctaa tctataatga    900
```

<210> SEQ ID NO 26
<211> LENGTH: 298
<212> TYPE: PRT
<213> ORGANISM: Bacillus thuringiensis

<400> SEQUENCE: 26

```
Met Ala Ile Phe Asn Phe Asp Ala Lys Val Val Glu Phe Ile Asn Trp
1               5                   10                  15

Trp Thr Ala Glu Phe Gly Gly Lys Asp Pro Arg Asn Ile Gln Ile Gly
            20                  25                  30

Tyr Glu Asn Arg Asp Ile Asn Val Val Pro Ser Ser Ser Asn Pro Ser
        35                  40                  45

Val Asn Val Ile Pro Lys Leu Ala Arg Ser Ser Val Gln Glu Leu Gln
    50                  55                  60

Asn Asn Thr Ser Val Thr Gln Thr Gln Glu Leu Ala Phe Ser Glu Thr
65                  70                  75                  80

Thr Thr Glu Ser Gln Ser Ser Thr Thr Thr His Gly Ala Ser Phe Ser
                85                  90                  95

Thr Thr Val Thr Ser Val Thr Gln Phe Thr Ala Glu Val Asn Phe Lys
            100                 105                 110

Ala Ile Gly Ser Ser Ile Glu Gln Thr Ile Gly Val Ser Met Thr Gly
        115                 120                 125

Asp Tyr Asn Tyr Ser Ser Ser Leu Thr Lys Thr Thr Glu Lys Ser Arg
    130                 135                 140

Ser Trp Thr Leu Thr Gln Pro Val Val Val Pro Pro Phe Ser Arg Val
145                 150                 155                 160

Thr Cys Thr Leu Leu Ile Tyr Asn Ala Pro Phe Ser Val Pro Val Asp
                165                 170                 175

Leu Asn Cys Asn Val Phe Gly Thr Leu Gly Gly Asp Phe Leu Ala Ser
            180                 185                 190

Tyr Thr Tyr Thr Val Ile Ser Thr Gly Arg Thr Val Asn Thr Ser Ile
        195                 200                 205

Thr Ala Ser Gln Met Thr Leu Thr Ser Trp Pro Gly Lys Pro Ser Glu
    210                 215                 220

Ile Ile Gly Ile Ala Pro Lys His Gly Leu Ile Phe Lys Gly Thr Gly
225                 230                 235                 240
```

```
Thr Gln Ala Ala Val His Gly Leu Tyr Ser Thr Val Lys Phe Val Glu
                245                 250                 255

Ser Pro Leu Pro Gly His Gln Gly Glu Lys Arg Thr Tyr Tyr Leu Pro
            260                 265                 270

Ala Gln Pro Val Asn Glu Asp Asp Leu Ile Ser Ser Val Phe Ser Asn
        275                 280                 285

Ile Pro Ile Ile Asn Pro Val Ser Asn Leu
    290                 295


<210> SEQ ID NO 27
<211> LENGTH: 897
<212> TYPE: DNA
<213> ORGANISM: Artificial sequence
<220> FEATURE:
<223> OTHER INFORMATION: Synthetic

<400> SEQUENCE: 27

atggctatct tcaacttcga cgccaaggtg gtcgagttca tcaactggtg gactgctgag      60

ttcggcggca aagatccaag gaacatccag atcggctacg agaatcgtga catcaacgtg     120

gtccctagct ctagcaaccc tagcgtgaat gtgatcccga agctcgctag gtccagcgta     180

caggagcttc agaacaacac cagcgttacc cagactcagg agctggcctt ctccgaaacg     240

acaaccgaat cccagtcctc tactaccact cacggcgctt cctttagcac taccgtgacc     300

tcagtgaccc aattcaccgc cgaggtcaac ttcaaggcaa tcggtagctc tattgagcaa     360

acaatcggcg tgagcatgac aggcgattac aactactcct cttcgttgac caagacaacc     420

gagaaatcac gctcctggac gctgacgcag cctgttgtgg ttcctccctt ctctcgcgtc     480

acgtgcaccc tcctaatcta caacgcgccc ttcagtgttc cagtcgatct caattgcaac     540

gtcttcggaa cgcttggagg cgactttctg gcctcgtaca cttacaccgt gatctcaacg     600

ggaagaactg tcaacacctc gattaccgcc tctcagatga ctctcaccag ttggcctggg     660

aagcccagtg agatcattgg tatcgctccg aagcacggcc tcatcttcaa gggcactggt     720

acacaggcgg ccgtccacgg gttgtactca acggtcaagt tcgttgaatc gccgctccct     780

ggccatcagg gcgagaaacg gacctactat ctgccagcac aaccagtgaa cgaggacgat     840

cttatttcct cggtgttctc caacattccg atcatcaacc cagtgtccaa tctgtga        897


<210> SEQ ID NO 28
<211> LENGTH: 298
<212> TYPE: PRT
<213> ORGANISM: Artificial sequence
<220> FEATURE:
<223> OTHER INFORMATION: Synthetic

<400> SEQUENCE: 28

Met Ala Ile Phe Asn Phe Asp Ala Lys Val Val Glu Phe Ile Asn Trp
1               5                   10                  15

Trp Thr Ala Glu Phe Gly Gly Lys Asp Pro Arg Asn Ile Gln Ile Gly
            20                  25                  30

Tyr Glu Asn Arg Asp Ile Asn Val Val Pro Ser Ser Ser Asn Pro Ser
        35                  40                  45

Val Asn Val Ile Pro Lys Leu Ala Arg Ser Ser Val Gln Glu Leu Gln
    50                  55                  60

Asn Asn Thr Ser Val Thr Gln Thr Gln Glu Leu Ala Phe Ser Glu Thr
65                  70                  75                  80

Thr Thr Glu Ser Gln Ser Ser Thr Thr Thr His Gly Ala Ser Phe Ser
```

-continued

```
                85                  90                  95

Thr Thr Val Thr Ser Val Thr Gln Phe Thr Ala Glu Val Asn Phe Lys
            100                 105                 110

Ala Ile Gly Ser Ser Ile Glu Gln Thr Ile Gly Val Ser Met Thr Gly
        115                 120                 125

Asp Tyr Asn Tyr Ser Ser Ser Leu Thr Lys Thr Thr Glu Lys Ser Arg
    130                 135                 140

Ser Trp Thr Leu Thr Gln Pro Val Val Val Pro Pro Phe Ser Arg Val
145                 150                 155                 160

Thr Cys Thr Leu Leu Ile Tyr Asn Ala Pro Phe Ser Val Pro Val Asp
                165                 170                 175

Leu Asn Cys Asn Val Phe Gly Thr Leu Gly Gly Asp Phe Leu Ala Ser
            180                 185                 190

Tyr Thr Tyr Thr Val Ile Ser Thr Gly Arg Thr Val Asn Thr Ser Ile
        195                 200                 205

Thr Ala Ser Gln Met Thr Leu Thr Ser Trp Pro Gly Lys Pro Ser Glu
    210                 215                 220

Ile Ile Gly Ile Ala Pro Lys His Gly Leu Ile Phe Lys Gly Thr Gly
225                 230                 235                 240

Thr Gln Ala Ala Val His Gly Leu Tyr Ser Thr Val Lys Phe Val Glu
                245                 250                 255

Ser Pro Leu Pro Gly His Gln Gly Glu Lys Arg Thr Tyr Tyr Leu Pro
            260                 265                 270

Ala Gln Pro Val Asn Glu Asp Asp Leu Ile Ser Ser Val Phe Ser Asn
        275                 280                 285

Ile Pro Ile Ile Asn Pro Val Ser Asn Leu
    290                 295


<210> SEQ ID NO 29
<211> LENGTH: 807
<212> TYPE: DNA
<213> ORGANISM: Bacillus thuringiensis

<400> SEQUENCE: 29

atgggaatta tcaacattca agacgaaatt aatgactaca tgaaaggtat gtatggtgca     60

acatctgtta aaagcacata tgacccctca ttcaaagtat ttaacgaatc tgtaacacct    120

caatatgatg tgatttcaac agaacctgta aataatcata ttactactaa agcaataaat    180

aatccagcgt cttcagaagt aaccagtaca gtaaccttca catggacgga aaccgacact    240

gtaacctctg cagtgactaa agggtataaa gtcggtggtt cagtaagctc aaaagcaact    300

tttaaatttg cttttgttac ttctgatgtt actgtaactg tatcagcaga atataattat    360

agtacaacag atacaacaac aaaaacagat acacgcacat ggacggattc gacgacagta    420

aaagcccctc caagaactaa tgtagaagtt gcatatatta tccaaactgg aaattataac    480

gttccggtta atgtagagtc tgatatgact ggaacgctat tttgcagagg gtatagagat    540

ggtgcactaa ttgcagcgac ttatatttct ataacagatt tagcagatta caagcctaat    600

ttgggtctta caaataaagg ggatggggtt gctcatttta aaggtgaagg ttatatagag    660

ggtgcacaag gcttaagaag ctatattcaa gttacagaat atccaatgga tgataaagac    720

agacgttcga caccaaaaac ttatacaatt gaaggttcat tagcacccaa tgttacttta    780

ataaatgata gaaaggaagg tagataa                                        807


<210> SEQ ID NO 30
```

-continued

<211> LENGTH: 268
<212> TYPE: PRT
<213> ORGANISM: Bacillus thuringiensis

<400> SEQUENCE: 30

Met Gly Ile Ile Asn Ile Gln Asp Glu Ile Asn Asp Tyr Met Lys Gly
1 5 10 15

Met Tyr Gly Ala Thr Ser Val Lys Ser Thr Tyr Asp Pro Ser Phe Lys
20 25 30

Val Phe Asn Glu Ser Val Thr Pro Gln Tyr Asp Val Ile Ser Thr Glu
35 40 45

Pro Val Asn Asn His Ile Thr Thr Lys Ala Ile Asn Asn Pro Ala Ser
50 55 60

Ser Glu Val Thr Ser Thr Val Thr Phe Thr Trp Thr Glu Thr Asp Thr
65 70 75 80

Val Thr Ser Ala Val Thr Lys Gly Tyr Lys Val Gly Gly Ser Val Ser
85 90 95

Ser Lys Ala Thr Phe Lys Phe Ala Phe Val Thr Ser Asp Val Thr Val
100 105 110

Thr Val Ser Ala Glu Tyr Asn Tyr Ser Thr Thr Asp Thr Thr Thr Lys
115 120 125

Thr Asp Thr Arg Thr Trp Thr Asp Ser Thr Thr Val Lys Ala Pro Pro
130 135 140

Arg Thr Asn Val Glu Val Ala Tyr Ile Ile Gln Thr Gly Asn Tyr Asn
145 150 155 160

Val Pro Val Asn Val Glu Ser Asp Met Thr Gly Thr Leu Phe Cys Arg
165 170 175

Gly Tyr Arg Asp Gly Ala Leu Ile Ala Ala Thr Tyr Ile Ser Ile Thr
180 185 190

Asp Leu Ala Asp Tyr Lys Pro Asn Leu Gly Leu Thr Asn Lys Gly Asp
195 200 205

Gly Val Ala His Phe Lys Gly Glu Gly Tyr Ile Glu Gly Ala Gln Gly
210 215 220

Leu Arg Ser Tyr Ile Gln Val Thr Glu Tyr Pro Met Asp Asp Lys Asp
225 230 235 240

Arg Arg Ser Thr Pro Lys Thr Tyr Thr Ile Glu Gly Ser Leu Ala Pro
245 250 255

Asn Val Thr Leu Ile Asn Asp Arg Lys Glu Gly Arg
260 265

<210> SEQ ID NO 31
<211> LENGTH: 807
<212> TYPE: DNA
<213> ORGANISM: Artificial sequence
<220> FEATURE:
<223> OTHER INFORMATION: Synthetic

<400> SEQUENCE: 31
atgggcatta tcaacattca agatgagatt aacgattaca tgaagggtat gtacggtgct 60
accagtgtga agtccactta cgatcctagt ttcaaggtct tcaacgagtc tgtgactcct 120
caatacgatg tgatttctac tgagcctgtg aacaatcaca ttactactaa ggctattaac 180
aatcctgcta gttctgaggt tactagcact gttactttca cttggactga gactgatact 240
gttactagcg ctgttactaa gggttacaag gttggtggat ctgtttcttc aaaggctacc 300
ttcaagtttg ctttcgttac ctcagatgtt accgttaccg tgagcgctga gtacaactac 360

-continued

```
tcaaccacag ataccaccac caagaccgat accagaacct ggaccgattc aaccacagtg    420

aaggcaccac ctcgcaccaa cgtggaggtc gcctacatta tccaaacagg caactacaat    480

gtcccagtca atgtcgaatc cgacatgaca ggaacactct tctgccgtgg ctacagggat    540

ggagcactta ttgcagccac ctacatctcc atcacagacc ttgccgacta caagccaaat    600

ctcggactca caaacaaggg agacggcgtc gcccacttca aaggcgaagg ctacatcgaa    660

ggtgcccagg gtctaaggag ctacatccaa gtgacagaat acccaatgga cgacaaagac    720

cgtcgctcca cacccaagac gtacaccatc gaagggtcgt tagcgccgaa tgtaacgctg    780

ataaatgacc gaaaggaagg gcggtga                                        807


<210> SEQ ID NO 32
<211> LENGTH: 268
<212> TYPE: PRT
<213> ORGANISM: Artificial sequence
<220> FEATURE:
<223> OTHER INFORMATION: Synthetic

<400> SEQUENCE: 32

Met Gly Ile Ile Asn Ile Gln Asp Glu Ile Asn Asp Tyr Met Lys Gly
1               5                   10                  15

Met Tyr Gly Ala Thr Ser Val Lys Ser Thr Tyr Asp Pro Ser Phe Lys
            20                  25                  30

Val Phe Asn Glu Ser Val Thr Pro Gln Tyr Asp Val Ile Ser Thr Glu
        35                  40                  45

Pro Val Asn Asn His Ile Thr Thr Lys Ala Ile Asn Asn Pro Ala Ser
    50                  55                  60

Ser Glu Val Thr Ser Thr Val Thr Phe Thr Trp Thr Glu Thr Asp Thr
65                  70                  75                  80

Val Thr Ser Ala Val Thr Lys Gly Tyr Lys Val Gly Gly Ser Val Ser
                85                  90                  95

Ser Lys Ala Thr Phe Lys Phe Ala Phe Val Thr Ser Asp Val Thr Val
            100                 105                 110

Thr Val Ser Ala Glu Tyr Asn Tyr Ser Thr Thr Asp Thr Thr Thr Lys
        115                 120                 125

Thr Asp Thr Arg Thr Trp Thr Asp Ser Thr Thr Val Lys Ala Pro Pro
    130                 135                 140

Arg Thr Asn Val Glu Val Ala Tyr Ile Ile Gln Thr Gly Asn Tyr Asn
145                 150                 155                 160

Val Pro Val Asn Val Glu Ser Asp Met Thr Gly Thr Leu Phe Cys Arg
                165                 170                 175

Gly Tyr Arg Asp Gly Ala Leu Ile Ala Ala Thr Tyr Ile Ser Ile Thr
            180                 185                 190

Asp Leu Ala Asp Tyr Lys Pro Asn Leu Gly Leu Thr Asn Lys Gly Asp
        195                 200                 205

Gly Val Ala His Phe Lys Gly Glu Gly Tyr Ile Glu Gly Ala Gln Gly
    210                 215                 220

Leu Arg Ser Tyr Ile Gln Val Thr Glu Tyr Pro Met Asp Asp Lys Asp
225                 230                 235                 240

Arg Arg Ser Thr Pro Lys Thr Tyr Thr Ile Glu Gly Ser Leu Ala Pro
                245                 250                 255

Asn Val Thr Leu Ile Asn Asp Arg Lys Glu Gly Arg
            260                 265


<210> SEQ ID NO 33
```

```
<211> LENGTH: 381
<212> TYPE: DNA
<213> ORGANISM: Bacillus thuringiensis

<400> SEQUENCE: 33

atgacagtat ataacgtaac ttttaccatt aaattcttta atcacggtga atgggggggg      60

ccagaacctt acggtaagat atatgcatat cttcaaaatc cagatcataa tttcgaaatt     120

tggtcacaag ataattgggg gaaggatacg cctgagaaaa gttctcacac tcaaacaatt     180

aaaataagta gcccaacagg ggggcctata gaccaaatgt gtttttatgg tgatgtaaaa     240

gaattcgacg taggaaattc agatgatgtt ctcgcctctc caagtcaaaa agtatgcagt     300

acgcctggca caacaataag gcttaacgga gatgagagtg gttcttatat agagattagt     360

tattccttgg ccccagctta a                                               381


<210> SEQ ID NO 34
<211> LENGTH: 126
<212> TYPE: PRT
<213> ORGANISM: Bacillus thuringiensis

<400> SEQUENCE: 34

Met Thr Val Tyr Asn Val Thr Phe Thr Ile Lys Phe Phe Asn His Gly
1               5                   10                  15

Glu Trp Gly Gly Pro Glu Pro Tyr Gly Lys Ile Tyr Ala Tyr Leu Gln
            20                  25                  30

Asn Pro Asp His Asn Phe Glu Ile Trp Ser Gln Asp Asn Trp Gly Lys
        35                  40                  45

Asp Thr Pro Glu Lys Ser Ser His Thr Gln Thr Ile Lys Ile Ser Ser
    50                  55                  60

Pro Thr Gly Gly Pro Ile Asp Gln Met Cys Phe Tyr Gly Asp Val Lys
65                  70                  75                  80

Glu Phe Asp Val Gly Asn Ser Asp Asp Val Leu Ala Ser Pro Ser Gln
                85                  90                  95

Lys Val Cys Ser Thr Pro Gly Thr Thr Ile Arg Leu Asn Gly Asp Glu
            100                 105                 110

Ser Gly Ser Tyr Ile Glu Ile Ser Tyr Ser Leu Ala Pro Ala
        115                 120                 125


<210> SEQ ID NO 35
<211> LENGTH: 381
<212> TYPE: DNA
<213> ORGANISM: Artificial sequence
<220> FEATURE:
<223> OTHER INFORMATION: Synthetic

<400> SEQUENCE: 35

atgaccgtgt acaacgtgac cttcaccatt aagttcttca atcacggtga gtggggcggt      60

cctgagccct acggcaaaat ctacgcctat ctccagaacc ctgaccacaa cttcgaaatc     120

tggtcccagg acaactgggg caaggacact cccgagaagt ccagccatac gcagaccatc     180

aagatcagca gcccgactgg cggcccgatt gaccagatgt gcttctacgg cgacgtcaag     240

gaatttgacg tgggaaactc agatgacgtc ctcgccagcc cgtcccagaa ggtttgctcg     300

acgccaggaa ctaccatccg cctgaatggc gatgaatctg ggtcgtacat cgagatcagt     360

tacagccttg cgcctgcatg a                                               381


<210> SEQ ID NO 36
<211> LENGTH: 126
```

<212> TYPE: PRT
<213> ORGANISM: Artificial sequence
<220> FEATURE:
<223> OTHER INFORMATION: Synthetic

<400> SEQUENCE: 36

```
Met Thr Val Tyr Asn Val Thr Phe Thr Ile Lys Phe Phe Asn His Gly
1               5                   10                  15

Glu Trp Gly Gly Pro Glu Pro Tyr Gly Lys Ile Tyr Ala Tyr Leu Gln
            20                  25                  30

Asn Pro Asp His Asn Phe Glu Ile Trp Ser Gln Asp Asn Trp Gly Lys
        35                  40                  45

Asp Thr Pro Glu Lys Ser Ser His Thr Gln Thr Ile Lys Ile Ser Ser
    50                  55                  60

Pro Thr Gly Gly Pro Ile Asp Gln Met Cys Phe Tyr Gly Asp Val Lys
65                  70                  75                  80

Glu Phe Asp Val Gly Asn Ser Asp Asp Val Leu Ala Ser Pro Ser Gln
                85                  90                  95

Lys Val Cys Ser Thr Pro Gly Thr Thr Ile Arg Leu Asn Gly Asp Glu
            100                 105                 110

Ser Gly Ser Tyr Ile Glu Ile Ser Tyr Ser Leu Ala Pro Ala
        115                 120                 125
```

<210> SEQ ID NO 37
<211> LENGTH: 906
<212> TYPE: DNA
<213> ORGANISM: Bacillus thuringiensis

<400> SEQUENCE: 37

```
atgaacaata attctaaatt tttattctca cctataaatg ctaatggaaa taatccttat      60

tttttagatg tagataattg gaaagatgta ttttgttatc ttgtaaatac tctggaaatg     120

aaatatacaa aagtagttaa taaatctcaa ttaatagatg cattatttcc agatcctaat     180

gatcaaagaa taggtccatt ttattggaat atatatgata attataaatt agataatgta     240

ttaaaaccat tatatgattt tcatagttca ttattaggaa atattcttga atggggatta     300

tttggaacaa taagaatggg tagtttggct tatcatattc aagattttgt aaatatcata     360

tgtgtaaaac atataaatga atttaatcaa attatagatg atttacaaca agataatgtt     420

tcaacaaaaa ctgttgataa atttagaaat atatgtattg aactacgtac taaatcactt     480

ctttttcctc aagaagtaaa taaaatatta gatgcaagta gaaatcttgc aaataatctt     540

ataaaagtta atgctatttt agattcaaca gtgcaacaat ttgaaaacgt ttatcaatca     600

tcacaatcaa ataacgataa atattatttg agaatcgtaa aagaatattt aggaaacgaa     660

caacaagatt tagaaaaaca aactcctaat catcttaata ctcttcaaaa attacgtgga     720

atatggactg tttttggaga taatttagaa aaattaattc atgcttgtga tgatgatctt     780

atagattttg atgcaatgat agctagtata aatttagagg atgctataac ttcttggaaa     840

gaagtaaaaa ataatataga taaatttata ccagaatggg aaatctttaa aaaacaagga     900

tgctaa                                                                906
```

<210> SEQ ID NO 38
<211> LENGTH: 301
<212> TYPE: PRT
<213> ORGANISM: Bacillus thuringiensis

<400> SEQUENCE: 38

```
Met Asn Asn Asn Ser Lys Phe Leu Phe Ser Pro Ile Asn Ala Asn Gly
1               5                   10                  15

Asn Asn Pro Tyr Phe Leu Asp Val Asp Asn Trp Lys Asp Val Phe Cys
            20                  25                  30

Tyr Leu Val Asn Thr Leu Glu Met Lys Tyr Thr Lys Val Val Asn Lys
        35                  40                  45

Ser Gln Leu Ile Asp Ala Leu Phe Pro Asp Pro Asn Asp Gln Arg Ile
    50                  55                  60

Gly Pro Phe Tyr Trp Asn Ile Tyr Asp Asn Tyr Lys Leu Asp Asn Val
65                  70                  75                  80

Leu Lys Pro Leu Tyr Asp Phe His Ser Ser Leu Leu Gly Asn Ile Leu
                85                  90                  95

Glu Trp Gly Leu Phe Gly Thr Ile Arg Met Gly Ser Leu Ala Tyr His
            100                 105                 110

Ile Gln Asp Phe Val Asn Ile Ile Cys Val Lys His Ile Asn Glu Phe
        115                 120                 125

Asn Gln Ile Ile Asp Asp Leu Gln Gln Asp Asn Val Ser Thr Lys Thr
    130                 135                 140

Val Asp Lys Phe Arg Asn Ile Cys Ile Glu Leu Arg Thr Lys Ser Leu
145                 150                 155                 160

Leu Phe Pro Gln Glu Val Asn Lys Ile Leu Asp Ala Ser Arg Asn Leu
                165                 170                 175

Ala Asn Asn Leu Ile Lys Val Asn Ala Ile Leu Asp Ser Thr Val Gln
            180                 185                 190

Gln Phe Glu Asn Val Tyr Gln Ser Ser Gln Ser Asn Asn Asp Lys Tyr
        195                 200                 205

Tyr Leu Arg Ile Val Lys Glu Tyr Leu Gly Asn Glu Gln Gln Asp Leu
    210                 215                 220

Glu Lys Gln Thr Pro Asn His Leu Asn Thr Leu Gln Lys Leu Arg Gly
225                 230                 235                 240

Ile Trp Thr Val Phe Gly Asp Asn Leu Glu Lys Leu Ile His Ala Cys
                245                 250                 255

Asp Asp Asp Leu Ile Asp Phe Asp Ala Met Ile Ala Ser Ile Asn Leu
            260                 265                 270

Glu Asp Ala Ile Thr Ser Trp Lys Glu Val Lys Asn Asn Ile Asp Lys
        275                 280                 285

Phe Ile Pro Glu Trp Glu Ile Phe Lys Lys Gln Gly Cys
    290                 295                 300


<210> SEQ ID NO 39
<211> LENGTH: 906
<212> TYPE: DNA
<213> ORGANISM: Artificial sequence
<220> FEATURE:
<223> OTHER INFORMATION: Synthetic

<400> SEQUENCE: 39

atgaacaaca actctaagtt cctcttctcg cccatcaacg ctaacggcaa caacccttac     60

ttcctagacg tggacaactg gaaggacgtc ttctgctacc tagtgaacac ccttgagatg    120

aagtacacta aggtggtgaa caagtcccag ctcattgacg ccctcttccc agatcctaac    180

gatcagcgta tcggaccctt ctactggaac atctacgata actacaagct cgacaacgtc    240

ctcaagccac tgtacgactt tcacagctca ctcctgggca acatccttga gtggggactc    300

tttgggacca ttcgcatggg ttctctggcc taccacatcc aagatttcgt caacattatc    360
```

-continued

```
tgcgttaagc acatcaacga gttcaaccag ataattgatg acctccagca agataacgtc    420

agcactaaga cggtggacaa gttccgcaac atctgcatcg aactccgcac gaagtccctt    480

ctgttccctc aggaggtcaa taagattctg gatgcgtcac ggaacctcgc aaataacctc    540

atcaaggtta atgcaatcct cgatagtacc gtccaacagt tcgagaacgt ttaccagtcg    600

tctcagtcta ataacgacaa gtactatttg agaatcgtaa aggagtatct cgggaatgag    660

cagcaagacc tggagaagca gacaccgaat cacctgaaca cccttcagaa gctccgtggc    720

atctggacag tcttcggcga caatcttgag aagctcattc atgcttgtga tgacgatctc    780

atcgacttcg acgctatgat cgcctccatc aacttggaag atgcgatcac ttcgtggaag    840

gaggttaaga ataacattga caaattcatc cctgaatggg aaatcttcaa gaaacagggc    900

tgctga                                                               906
```

```
<210> SEQ ID NO 40
<211> LENGTH: 301
<212> TYPE: PRT
<213> ORGANISM: Artificial sequence
<220> FEATURE:
<223> OTHER INFORMATION: Synthetic

<400> SEQUENCE: 40

Met Asn Asn Asn Ser Lys Phe Leu Phe Ser Pro Ile Asn Ala Asn Gly
1               5                   10                  15

Asn Asn Pro Tyr Phe Leu Asp Val Asp Asn Trp Lys Asp Val Phe Cys
            20                  25                  30

Tyr Leu Val Asn Thr Leu Glu Met Lys Tyr Thr Lys Val Val Asn Lys
        35                  40                  45

Ser Gln Leu Ile Asp Ala Leu Phe Pro Asp Pro Asn Asp Gln Arg Ile
    50                  55                  60

Gly Pro Phe Tyr Trp Asn Ile Tyr Asp Asn Tyr Lys Leu Asp Asn Val
65                  70                  75                  80

Leu Lys Pro Leu Tyr Asp Phe His Ser Ser Leu Leu Gly Asn Ile Leu
                85                  90                  95

Glu Trp Gly Leu Phe Gly Thr Ile Arg Met Gly Ser Leu Ala Tyr His
            100                 105                 110

Ile Gln Asp Phe Val Asn Ile Ile Cys Val Lys His Ile Asn Glu Phe
        115                 120                 125

Asn Gln Ile Ile Asp Asp Leu Gln Gln Asp Asn Val Ser Thr Lys Thr
    130                 135                 140

Val Asp Lys Phe Arg Asn Ile Cys Ile Glu Leu Arg Thr Lys Ser Leu
145                 150                 155                 160

Leu Phe Pro Gln Glu Val Asn Lys Ile Leu Asp Ala Ser Arg Asn Leu
                165                 170                 175

Ala Asn Asn Leu Ile Lys Val Asn Ala Ile Leu Asp Ser Thr Val Gln
            180                 185                 190

Gln Phe Glu Asn Val Tyr Gln Ser Ser Gln Ser Asn Asn Asp Lys Tyr
        195                 200                 205

Tyr Leu Arg Ile Val Lys Glu Tyr Leu Gly Asn Glu Gln Gln Asp Leu
    210                 215                 220

Glu Lys Gln Thr Pro Asn His Leu Asn Thr Leu Gln Lys Leu Arg Gly
225                 230                 235                 240

Ile Trp Thr Val Phe Gly Asp Asn Leu Glu Lys Leu Ile His Ala Cys
                245                 250                 255

Asp Asp Asp Leu Ile Asp Phe Asp Ala Met Ile Ala Ser Ile Asn Leu
```

```
            260                 265                 270

Glu Asp Ala Ile Thr Ser Trp Lys Glu Val Lys Asn Asn Ile Asp Lys
        275                 280                 285

Phe Ile Pro Glu Trp Glu Ile Phe Lys Lys Gln Gly Cys
    290                 295                 300


<210> SEQ ID NO 41
<211> LENGTH: 861
<212> TYPE: DNA
<213> ORGANISM: Bacillus thuringiensis

<400> SEQUENCE: 41

atgaataata ttaataagaa gtatagactt aatgatatga ttaataaaaa tcaatttatt      60

atttcaaaaa cagaatgggt tactataaga acatatattg aaattggatt aactttacca     120

gtaaatgaac aagatttacg aaaatatttc aatttaaatc cagatataac actatctaat     180

gatttttctg aattatttga tatttgttat tctattaaaa atttagctca atggtggaat     240

accactatac ttcctttaat tattaaatct gttaataata ttacatcata tggatttaaa     300

attgctggta atccttttaa taataaagaa ggatactttt caaaattaca aaatgaatta     360

catattatta ataattataa ttctaataaa acaacaaaaa ctattaaaca atttcaatct     420

cggtgtaaca ttttaattaa ggaagttaaa caatatgaag atgttaccaa aaatattgta     480

atattattaa ataaactttt atatggtaat cagcaaaaat tagaagggat tattaatatt     540

caaaaacgat taaaagtggt tcaaacaact tttaatccga tatctaatga aactaattta     600

atttataaaa aactatttga aaaaataaaa aaaataaata ttggtttttt tgaatgcgta     660

aataaatata taagtatatt taacaaaata attattatgt ggtcaaatac tgaacaacaa     720

attatagatt ttaaatcaat tttatttcaa gaatttaaaa atataaatga aacagttatt     780

gaatttgaag atattattga gatttggtta attatagcta aaaaatctcg tgaatttact     840

ttaaatgctt atatatctta g                                                861


<210> SEQ ID NO 42
<211> LENGTH: 286
<212> TYPE: PRT
<213> ORGANISM: Bacillus thuringiensis

<400> SEQUENCE: 42

Met Asn Asn Ile Asn Lys Lys Tyr Arg Leu Asn Asp Met Ile Asn Lys
1               5                   10                  15

Asn Gln Phe Ile Ile Ser Lys Thr Glu Trp Val Thr Ile Arg Thr Tyr
            20                  25                  30

Ile Glu Ile Gly Leu Thr Leu Pro Val Asn Glu Gln Asp Leu Arg Lys
        35                  40                  45

Tyr Phe Asn Leu Asn Pro Asp Ile Thr Leu Ser Asn Asp Phe Ser Glu
    50                  55                  60

Leu Phe Asp Ile Cys Tyr Ser Ile Lys Asn Leu Ala Gln Trp Trp Asn
65                  70                  75                  80

Thr Thr Ile Leu Pro Leu Ile Ile Lys Ser Val Asn Asn Ile Thr Ser
                85                  90                  95

Tyr Gly Phe Lys Ile Ala Gly Asn Pro Phe Asn Asn Lys Glu Gly Tyr
            100                 105                 110

Phe Ser Lys Leu Gln Asn Glu Leu His Ile Ile Asn Asn Tyr Asn Ser
        115                 120                 125

Asn Lys Thr Thr Lys Thr Ile Lys Gln Phe Gln Ser Arg Cys Asn Ile
```

```
    130                 135                 140

Leu Ile Lys Glu Val Lys Gln Tyr Glu Asp Val Thr Lys Asn Ile Val
145                 150                 155                 160

Ile Leu Leu Asn Lys Leu Leu Tyr Gly Asn Gln Gln Lys Leu Glu Gly
                165                 170                 175

Ile Ile Asn Ile Gln Lys Arg Leu Lys Val Val Gln Thr Thr Phe Asn
            180                 185                 190

Pro Ile Ser Asn Glu Thr Asn Leu Ile Tyr Lys Lys Leu Phe Glu Lys
        195                 200                 205

Ile Lys Lys Ile Asn Ile Gly Phe Phe Glu Cys Val Asn Lys Tyr Ile
    210                 215                 220

Ser Ile Phe Asn Lys Ile Ile Ile Met Trp Ser Asn Thr Glu Gln Gln
225                 230                 235                 240

Ile Ile Asp Phe Lys Ser Ile Leu Phe Gln Glu Phe Lys Asn Ile Asn
                245                 250                 255

Glu Thr Val Ile Glu Phe Glu Asp Ile Ile Glu Ile Trp Leu Ile Ile
            260                 265                 270

Ala Lys Lys Ser Arg Glu Phe Thr Leu Asn Ala Tyr Ile Ser
        275                 280                 285
```

<210> SEQ ID NO 43
<211> LENGTH: 861
<212> TYPE: DNA
<213> ORGANISM: Artificial sequence
<220> FEATURE:
<223> OTHER INFORMATION: Synthetic

<400> SEQUENCE: 43

```
atgaacaaca ttaacaagaa gtaccgcctg aacgacatga ttaacaagaa ccagttcatc     60

attagcaaga ctgagtgggt gaccatcagg acgtacatcg agatcggcct gaccctgccc    120

gtgaacgagc aagacctgag gaagtacttc aacctcaacc ctgacattac actgagcaac    180

gacttctcgg agctgttcga catctgctac tctatcaaga atctcgccca atggtggaac    240

acaacgatcc ttccgctaat cattaagtct gtgaacaaca tcactagcta tggcttcaag    300

atcgcgggca acccgttcaa caataaggag ggttacttta gtaagctcca gaacgaactc    360

cacatcatta acaattacaa ttcgaacaag acgactaaga cgatcaagca gtttcagtca    420

cggtgcaaca tcttgattaa ggaggttaaa caatacgaag atgtaacgaa gaacatcgtg    480

atcctcctta acaagctcct gtacggcaac cagcagaagc tcgaagggat cattaacata    540

cagaagcgtc tcaaggtggt ccagaccacg ttcaatccca tctccaatga gactaacctt    600

atctacaaga aactctttga gaagatcaag aagatcaaca tcggcttctt tgagtgtgtc    660

aacaagtaca tctccatctt caacaagata atcattatgt ggtcaaacac tgagcagcag    720

atcatcgact tcaagtccat actgttccag gagttcaaga acatcaatga gaccgtcatc    780

gagttcgaag acatcatcga gatttggctt atcatcgcta agaagtctag ggagttcacc    840

ctgaatgcgt acatctcctg a                                              861
```

<210> SEQ ID NO 44
<211> LENGTH: 286
<212> TYPE: PRT
<213> ORGANISM: Artificial sequence
<220> FEATURE:
<223> OTHER INFORMATION: Synthetic

<400> SEQUENCE: 44

-continued

Met Asn Asn Ile Asn Lys Lys Tyr Arg Leu Asn Asp Met Ile Asn Lys
1 5 10 15

Asn Gln Phe Ile Ile Ser Lys Thr Glu Trp Val Thr Ile Arg Thr Tyr
20 25 30

Ile Glu Ile Gly Leu Thr Leu Pro Val Asn Glu Gln Asp Leu Arg Lys
35 40 45

Tyr Phe Asn Leu Asn Pro Asp Ile Thr Leu Ser Asn Asp Phe Ser Glu
50 55 60

Leu Phe Asp Ile Cys Tyr Ser Ile Lys Asn Leu Ala Gln Trp Trp Asn
65 70 75 80

Thr Thr Ile Leu Pro Leu Ile Ile Lys Ser Val Asn Asn Ile Thr Ser
85 90 95

Tyr Gly Phe Lys Ile Ala Gly Asn Pro Phe Asn Asn Lys Glu Gly Tyr
100 105 110

Phe Ser Lys Leu Gln Asn Glu Leu His Ile Ile Asn Asn Tyr Asn Ser
115 120 125

Asn Lys Thr Thr Lys Thr Ile Lys Gln Phe Gln Ser Arg Cys Asn Ile
130 135 140

Leu Ile Lys Glu Val Lys Gln Tyr Glu Asp Val Thr Lys Asn Ile Val
145 150 155 160

Ile Leu Leu Asn Lys Leu Leu Tyr Gly Asn Gln Gln Lys Leu Glu Gly
165 170 175

Ile Ile Asn Ile Gln Lys Arg Leu Lys Val Val Gln Thr Thr Phe Asn
180 185 190

Pro Ile Ser Asn Glu Thr Asn Leu Ile Tyr Lys Lys Leu Phe Glu Lys
195 200 205

Ile Lys Lys Ile Asn Ile Gly Phe Phe Glu Cys Val Asn Lys Tyr Ile
210 215 220

Ser Ile Phe Asn Lys Ile Ile Ile Met Trp Ser Asn Thr Glu Gln Gln
225 230 235 240

Ile Ile Asp Phe Lys Ser Ile Leu Phe Gln Glu Phe Lys Asn Ile Asn
245 250 255

Glu Thr Val Ile Glu Phe Glu Asp Ile Ile Glu Ile Trp Leu Ile Ile
260 265 270

Ala Lys Lys Ser Arg Glu Phe Thr Leu Asn Ala Tyr Ile Ser
275 280 285

<210> SEQ ID NO 45
<211> LENGTH: 960
<212> TYPE: DNA
<213> ORGANISM: Bacillus thuringiensis

<400> SEQUENCE: 45
atgacaatta caaatatcga attagctata cgagattata caaattggga tggtactcgt 60
gaaattccgg gatacatcaa tcgtcaggtt atagatgggc caaatatata tgactatgta 120
attagtgact ctgtagctgt tccaaaaact gtaattttca atgtaaatcc aactccatat 180
accgggccta atataatatc agaaaataat acagatgtaa atcaaaataa acgtattaag 240
ttttctgaaa aagtagttga aactactaca catactacta caaagggttt taaaattggc 300
ggtggaatta aatctactac aaaaggaact ttaaaattaa aatttcctgt aggagaacta 360
gggtttgagc aaactcttga gctacctctt acaggagaat acaatagtag ttccactacg 420
gggaacactt gtgcaaatga aaaattatgg gaaataacag ataatataac tgtacctcca 480
cattcacgtg taacttcaac tttaataatt atgaaaacgg aagtaagggt tccaatggaa 540
ttaaccacta atcttagagg aactaattct agtggtgaag gctcgttccc tactagtaat 600
ggtctttttt catatactac ttcagctcgt ggaactgtag gcggtatttt tgttagttat 660
tacgtgaggc ctgcttctgc attgtataat acctcttggc ctgataaacc tgcaactttt 720
aattctattg gctcaaatga atctctaaat ttattgggat ctggatattc tgacgtagtt 780
ccatctctat atgttactat tagacaagat caaactccat tatcaggata tccaggtgaa 840
acgaaaacct ggtattcaga taaagtgata ttaagagatg gaagaattgt aacactacca 900
agcaatgctg atgtaaatat gtcacaaaca gccaaaattc catattgtga tagatcttaa 960

<210> SEQ ID NO 46
<211> LENGTH: 319
<212> TYPE: PRT
<213> ORGANISM: Bacillus thuringiensis

<400> SEQUENCE: 46

Met Thr Ile Thr Asn Ile Glu Leu Ala Ile Arg Asp Tyr Thr Asn Trp
1 5 10 15

Asp Gly Thr Arg Glu Ile Pro Gly Tyr Ile Asn Arg Gln Val Ile Asp
20 25 30

Gly Pro Asn Ile Tyr Asp Tyr Val Ile Ser Asp Ser Val Ala Val Pro
35 40 45

Lys Thr Val Ile Phe Asn Val Asn Pro Thr Pro Tyr Thr Gly Pro Asn
50 55 60

Ile Ile Ser Glu Asn Asn Thr Asp Val Asn Gln Asn Lys Arg Ile Lys
65 70 75 80

Phe Ser Glu Lys Val Val Glu Thr Thr Thr His Thr Thr Thr Lys Gly
85 90 95

Phe Lys Ile Gly Gly Gly Ile Lys Ser Thr Thr Lys Gly Thr Leu Lys
100 105 110

Leu Lys Phe Pro Val Gly Glu Leu Gly Phe Glu Gln Thr Leu Glu Leu
115 120 125

Pro Leu Thr Gly Glu Tyr Asn Ser Ser Ser Thr Thr Gly Asn Thr Cys
130 135 140

Ala Asn Glu Lys Leu Trp Glu Ile Thr Asp Asn Ile Thr Val Pro Pro
145 150 155 160

His Ser Arg Val Thr Ser Thr Leu Ile Ile Met Lys Thr Glu Val Arg
165 170 175

Val Pro Met Glu Leu Thr Thr Asn Leu Arg Gly Thr Asn Ser Ser Gly
180 185 190

Glu Gly Ser Phe Pro Thr Ser Asn Gly Leu Phe Ser Tyr Thr Thr Ser
195 200 205

Ala Arg Gly Thr Val Gly Gly Ile Phe Val Ser Tyr Tyr Val Arg Pro
210 215 220

Ala Ser Ala Leu Tyr Asn Thr Ser Trp Pro Asp Lys Pro Ala Thr Phe
225 230 235 240

Asn Ser Ile Gly Ser Asn Glu Ser Leu Asn Leu Leu Gly Ser Gly Tyr
245 250 255

Ser Asp Val Val Pro Ser Leu Tyr Val Thr Ile Arg Gln Asp Gln Thr
260 265 270

Pro Leu Ser Gly Tyr Pro Gly Glu Thr Lys Thr Trp Tyr Ser Asp Lys
275 280 285

Val Ile Leu Arg Asp Gly Arg Ile Val Thr Leu Pro Ser Asn Ala Asp
290 295 300

Val Asn Met Ser Gln Thr Ala Lys Ile Pro Tyr Cys Asp Arg Ser
305 310 315

<210> SEQ ID NO 47
<211> LENGTH: 960
<212> TYPE: DNA
<213> ORGANISM: Artificial sequence
<220> FEATURE:
<223> OTHER INFORMATION: Synthetic

<400> SEQUENCE: 47
atgaccatca ccaacatcga actcgccatc cgcgactaca ctaactggga cggcactagg 60
gagatccctg gctacatcaa ccgccaagtg atcgacggcc cgaacatcta cgactacgtg 120
atctctgact ccgtggccgt gcctaagacc gtcatcttca acgtgaaccc aactccgtac 180
actgggccaa acatcataag cgagaacaat actgacgtta atcagaacaa gcgcattaag 240
ttctcggaga aggttgtgga gaccactacc catacgacca caaagggctt caagatcggt 300
ggcggtatca agtccaccac gaagggcact ctcaagctga aattccctgt cggtgagctt 360
ggatttgagc aaaccctcga acttcctctg acgggcgagt acaactccag ctccaccact 420
gggaacacct gcgccaacga gaaactgtgg gaaattaccg acaacataac cgtcccgcca 480
cactcccgag tcacctctac gcttatcatt atgaagacag aagtaagggt gccgatggag 540
ttgacgacta acctgcgtgg aacaaacagt tccggcgaag ggagctttcc tacctctaat 600
ggcctcttta gctacaccac atcagctaga ggaaccgttg gcggtatctt cgtttcttac 660
tacgtccgtc cggccagcgc actctacaac acatcatggc ctgacaagcc cgcgaccttc 720
aatagcattg gtagcaatga gtcgctcaac ctgctcggtt ccggttacag cgatgttgtg 780
cccagtctct atgttacgat ccggcaagat cagactccgc tgtccggcta cccaggcgag 840
acaaagacat ggtactccga taaggtcatc cttcgtgatg ggcgcattgt caccctccct 900
tctaatgcgg atgtcaacat gagccagacg gctaagatcc cgtattgcga ccggtcctga 960

<210> SEQ ID NO 48
<211> LENGTH: 319
<212> TYPE: PRT
<213> ORGANISM: Artificial sequence
<220> FEATURE:
<223> OTHER INFORMATION: Synthetic

<400> SEQUENCE: 48

Met Thr Ile Thr Asn Ile Glu Leu Ala Ile Arg Asp Tyr Thr Asn Trp
1 5 10 15

Asp Gly Thr Arg Glu Ile Pro Gly Tyr Ile Asn Arg Gln Val Ile Asp
20 25 30

Gly Pro Asn Ile Tyr Asp Tyr Val Ile Ser Asp Ser Val Ala Val Pro
35 40 45

Lys Thr Val Ile Phe Asn Val Asn Pro Thr Pro Tyr Thr Gly Pro Asn
50 55 60

Ile Ile Ser Glu Asn Asn Thr Asp Val Asn Gln Asn Lys Arg Ile Lys
65 70 75 80

Phe Ser Glu Lys Val Val Glu Thr Thr Thr His Thr Thr Thr Lys Gly
85 90 95

Phe Lys Ile Gly Gly Gly Ile Lys Ser Thr Thr Lys Gly Thr Leu Lys
100 105 110

Leu Lys Phe Pro Val Gly Glu Leu Gly Phe Glu Gln Thr Leu Glu Leu
115 120 125

```
Pro Leu Thr Gly Glu Tyr Asn Ser Ser Ser Thr Thr Gly Asn Thr Cys
    130                 135                 140

Ala Asn Glu Lys Leu Trp Glu Ile Thr Asp Asn Ile Thr Val Pro Pro
145                 150                 155                 160

His Ser Arg Val Thr Ser Thr Leu Ile Ile Met Lys Thr Glu Val Arg
                165                 170                 175

Val Pro Met Glu Leu Thr Thr Asn Leu Arg Gly Thr Asn Ser Ser Gly
            180                 185                 190

Glu Gly Ser Phe Pro Thr Ser Asn Gly Leu Phe Ser Tyr Thr Thr Ser
        195                 200                 205

Ala Arg Gly Thr Val Gly Gly Ile Phe Val Ser Tyr Tyr Val Arg Pro
    210                 215                 220

Ala Ser Ala Leu Tyr Asn Thr Ser Trp Pro Asp Lys Pro Ala Thr Phe
225                 230                 235                 240

Asn Ser Ile Gly Ser Asn Glu Ser Leu Asn Leu Leu Gly Ser Gly Tyr
                245                 250                 255

Ser Asp Val Val Pro Ser Leu Tyr Val Thr Ile Arg Gln Asp Gln Thr
            260                 265                 270

Pro Leu Ser Gly Tyr Pro Gly Glu Thr Lys Thr Trp Tyr Ser Asp Lys
        275                 280                 285

Val Ile Leu Arg Asp Gly Arg Ile Val Thr Leu Pro Ser Asn Ala Asp
    290                 295                 300

Val Asn Met Ser Gln Thr Ala Lys Ile Pro Tyr Cys Asp Arg Ser
305                 310                 315
```

<210> SEQ ID NO 49
<211> LENGTH: 855
<212> TYPE: DNA
<213> ORGANISM: Bacillus thuringiensis

<400> SEQUENCE: 49

```
atgaaatatc acaaaaaatt tcatgaaata gcttgggagt ttgctgaaaa atggactgaa      60

caagaaggtt tggagttagc aaatgtcgat tatgtgaatc ctgctactgg taaagacacg     120

ttgaatttcg tgaataaatt tgaatatatc ggaaaaataa aagagggaaa tctttgccca     180

gagatagtag caaatgagtc tttttcaaat tcaaaatgtg atactttgaa aaataatctc     240

cataaaaaat tatttttgaa acaatattat ttatgggata tagactatca atttataatt     300

ccgccttcaa tttatacaaa tccaatatta ccgccatgtc ttagtaaaaa aatcaatcca     360

gcaatacagg tagatttatt taaaagagca taccattttg aatctcaact aaacaattct     420

gaaataatag aagcagggat ttatattgaa cctaatcaaa cgataaatgc taaagtaata     480

gcagaatata aaaatgtgca acaaaaatat tgtatacacc ttaaaatttc aggaagtatt     540

gttattgaag tgaaaaaaaa tcgtaattct tgtaaggatt ctaaaacatt ttatactatc     600

ccaatcgtag atttgtataa atcagagctt gcacataatc attcttttca tttagatggg     660

gagactgtta tatttactga aaaaggtatg tttaaaggcc taatttgttc taatgtattt     720

atcgaagggg aacggtttaa tttaaaaaca ggagaatgct taggtaaata tataatacca     780

ttaggtatgg acgaagaaaa agttctagaa aatagtaaat caatattttt taattcagaa     840

aaaggaggaa tttaa                                                      855
```

<210> SEQ ID NO 50
<211> LENGTH: 284
<212> TYPE: PRT

<213> ORGANISM: Bacillus thuringiensis

<400> SEQUENCE: 50

```
Met Lys Tyr His Lys Lys Phe His Glu Ile Ala Trp Glu Phe Ala Glu
1               5                   10                  15

Lys Trp Thr Glu Gln Glu Gly Leu Glu Leu Ala Asn Val Asp Tyr Val
            20                  25                  30

Asn Pro Ala Thr Gly Lys Asp Thr Leu Asn Phe Val Asn Lys Phe Glu
        35                  40                  45

Tyr Ile Gly Lys Ile Lys Glu Gly Asn Leu Cys Pro Glu Ile Val Ala
    50                  55                  60

Asn Glu Ser Phe Ser Asn Ser Lys Cys Asp Thr Leu Lys Asn Asn Leu
65                  70                  75                  80

His Lys Lys Leu Phe Leu Lys Gln Tyr Tyr Leu Trp Asp Ile Asp Tyr
                85                  90                  95

Gln Phe Ile Ile Pro Pro Ser Ile Tyr Thr Asn Pro Ile Leu Pro Pro
            100                 105                 110

Cys Leu Ser Lys Lys Ile Asn Pro Ala Ile Gln Val Asp Leu Phe Lys
        115                 120                 125

Arg Ala Tyr His Phe Glu Ser Gln Leu Asn Asn Ser Glu Ile Ile Glu
    130                 135                 140

Ala Gly Ile Tyr Ile Glu Pro Asn Gln Thr Ile Asn Ala Lys Val Ile
145                 150                 155                 160

Ala Glu Tyr Lys Asn Val Gln Gln Lys Tyr Cys Ile His Leu Lys Ile
                165                 170                 175

Ser Gly Ser Ile Val Ile Glu Val Lys Lys Asn Arg Asn Ser Cys Lys
            180                 185                 190

Asp Ser Lys Thr Phe Tyr Thr Ile Pro Ile Val Asp Leu Tyr Lys Ser
        195                 200                 205

Glu Leu Ala His Asn His Ser Phe His Leu Asp Gly Glu Thr Val Ile
    210                 215                 220

Phe Thr Glu Lys Gly Met Phe Lys Gly Leu Ile Cys Ser Asn Val Phe
225                 230                 235                 240

Ile Glu Gly Glu Arg Phe Asn Leu Lys Thr Gly Glu Cys Leu Gly Lys
                245                 250                 255

Tyr Ile Ile Pro Leu Gly Met Asp Glu Glu Lys Val Leu Glu Asn Ser
            260                 265                 270

Lys Ser Ile Phe Phe Asn Ser Glu Lys Gly Gly Ile
        275                 280
```

<210> SEQ ID NO 51
<211> LENGTH: 855
<212> TYPE: DNA
<213> ORGANISM: Artificial sequence
<220> FEATURE:
<223> OTHER INFORMATION: Synthetic

<400> SEQUENCE: 51

```
atgaagtacc acaagaagtt ccacgagatc gcctgggagt tcgctgagaa gtggactgag      60

caggagggcc tagagctggc taacgtggac tacgtgaacc ctgccaccgg caaggacacc     120

ctgaacttcg tgaacaagtt cgagtacatc ggaaagatta aggaggggaa cctctgtccc     180

gagattgttg ccaatgagtc tttcagcaat agcaagtgcg atacgctcaa gaataacctc     240

cacaagaaac tgttcttgaa gcagtactac ctgtgggaca tcgactacca gttcatcatt     300

ccaccgagca tctacaccaa ccctatcctc cctccatgcc tgtcgaagaa gatcaacccg     360
```

```
gccatccaag tggacctctt caagcgcgct taccactttg agtcccagct taacaatagc    420

gagatcatcg aggccggtat ctacattgaa cccaaccaga ccatcaatgc gaaggttatc    480

gcggagtaca agaacgtgca acagaagtat tgcatccacc tcaagatcag tggtagtatt    540

gtcatcgagg tcaagaagaa caggaactcg tgcaaggact caaagacgtt ctacactatc    600

ccgatagtgg acctttacaa gtctgaactc gcccacaacc attcattcca tctcgatgga    660

gagactgtaa tcttcaccga gaagggcatg tttaagggcc ttatttgctc caacgtcttc    720

atcgaaggcg aacgcttcaa ccttaagaca ggagaatgcc tggggaagta catcatccct    780

ttgggcatgg atgaggagaa ggttctggag aactccaagt ctatcttctt caactccgag    840

aagggcggga tctga                                                      855
```

<210> SEQ ID NO 52
<211> LENGTH: 284
<212> TYPE: PRT
<213> ORGANISM: Artificial sequence
<220> FEATURE:
<223> OTHER INFORMATION: Synthetic

<400> SEQUENCE: 52

```
Met Lys Tyr His Lys Lys Phe His Glu Ile Ala Trp Glu Phe Ala Glu
1               5                   10                  15

Lys Trp Thr Glu Gln Glu Gly Leu Glu Leu Ala Asn Val Asp Tyr Val
            20                  25                  30

Asn Pro Ala Thr Gly Lys Asp Thr Leu Asn Phe Val Asn Lys Phe Glu
        35                  40                  45

Tyr Ile Gly Lys Ile Lys Glu Gly Asn Leu Cys Pro Glu Ile Val Ala
    50                  55                  60

Asn Glu Ser Phe Ser Asn Ser Lys Cys Asp Thr Leu Lys Asn Asn Leu
65                  70                  75                  80

His Lys Lys Leu Phe Leu Lys Gln Tyr Tyr Leu Trp Asp Ile Asp Tyr
                85                  90                  95

Gln Phe Ile Ile Pro Pro Ser Ile Tyr Thr Asn Pro Ile Leu Pro Pro
            100                 105                 110

Cys Leu Ser Lys Lys Ile Asn Pro Ala Ile Gln Val Asp Leu Phe Lys
        115                 120                 125

Arg Ala Tyr His Phe Glu Ser Gln Leu Asn Asn Ser Glu Ile Ile Glu
    130                 135                 140

Ala Gly Ile Tyr Ile Glu Pro Asn Gln Thr Ile Asn Ala Lys Val Ile
145                 150                 155                 160

Ala Glu Tyr Lys Asn Val Gln Gln Lys Tyr Cys Ile His Leu Lys Ile
                165                 170                 175

Ser Gly Ser Ile Val Ile Glu Val Lys Lys Asn Arg Asn Ser Cys Lys
            180                 185                 190

Asp Ser Lys Thr Phe Tyr Thr Ile Pro Ile Val Asp Leu Tyr Lys Ser
        195                 200                 205

Glu Leu Ala His Asn His Ser Phe His Leu Asp Gly Glu Thr Val Ile
    210                 215                 220

Phe Thr Glu Lys Gly Met Phe Lys Gly Leu Ile Cys Ser Asn Val Phe
225                 230                 235                 240

Ile Glu Gly Glu Arg Phe Asn Leu Lys Thr Gly Glu Cys Leu Gly Lys
                245                 250                 255

Tyr Ile Ile Pro Leu Gly Met Asp Glu Glu Lys Val Leu Glu Asn Ser
            260                 265                 270
```

-continued

Lys Ser Ile Phe Phe Asn Ser Glu Lys Gly Gly Ile
275 280

<210> SEQ ID NO 53
<211> LENGTH: 903
<212> TYPE: DNA
<213> ORGANISM: Bacillus thuringiensis

<400> SEQUENCE: 53
atgctagcat tcatattttc aggaggaagt agccaacttt gtacgtcaat acgtaatgaa 60
tataataaca tattgcaagg ggggggatg gatgtatctt catccttccg tgtagatcct 120
tctaaaataa atataaatga tttggaagtg acatatccag agttaaatat tcccgataac 180
ataatagctt ctatagtatc taataatagc ttcgagaata gaggatttat aactaacgaa 240
acttacgcta ccgctgaggt aaccagagca ttaaccgaaa caattactac agctactact 300
agagggttta aattcacgca aggttttacc tatacaaata agattaacct cagaatacca 360
attgccggtt cagaatcaac aatttccttt tcaacatctt ttgaacaaaa tatttcaacc 420
actgaaacaa taacaaaaac tgaaacgata actatacttg tacctagaca aacggttaca 480
gtaaggccta gaacaagaaa agttgttcaa ataagacttt atcaattacg aattcctaga 540
gtattcaccg aaatatctgc ttatgtaaca ggtactctta gacaaccaat tcctcaagcg 600
aatcctgatg tttatgctac tctggtaagt gtcaataatg catgtcctaa tgcatttgtt 660
aaccgtgaca attttttgag aatagatcgc gaaaagcggg gcttagcgtt aagaggagaa 720
ggtgaattta gtggaaatat agtttcatta gatttcctga ttacgactac tgaatatgat 780
ttggatacaa atgctattat taatatagat aataccttgg gcagagcagc tattctagga 840
agtgagcctt gtggaactat tgcttataca gaaccaattg acattattca cactgattgt 900
taa 903

<210> SEQ ID NO 54
<211> LENGTH: 300
<212> TYPE: PRT
<213> ORGANISM: Bacillus thuringiensis

<400> SEQUENCE: 54

Met Leu Ala Phe Ile Phe Ser Gly Gly Ser Ser Gln Leu Cys Thr Ser
1 5 10 15

Ile Arg Asn Glu Tyr Asn Asn Ile Leu Gln Gly Gly Gly Met Asp Val
20 25 30

Ser Ser Ser Phe Arg Val Asp Pro Ser Lys Ile Asn Ile Asn Asp Leu
35 40 45

Glu Val Thr Tyr Pro Glu Leu Asn Ile Pro Asp Asn Ile Ile Ala Ser
50 55 60

Ile Val Ser Asn Asn Ser Phe Glu Asn Arg Gly Phe Ile Thr Asn Glu
65 70 75 80

Thr Tyr Ala Thr Ala Glu Val Thr Arg Ala Leu Thr Glu Thr Ile Thr
85 90 95

Thr Ala Thr Thr Arg Gly Phe Lys Phe Thr Gln Gly Phe Thr Tyr Thr
100 105 110

Asn Lys Ile Asn Leu Arg Ile Pro Ile Ala Gly Ser Glu Ser Thr Ile
115 120 125

Ser Phe Ser Thr Ser Phe Glu Gln Asn Ile Ser Thr Thr Glu Thr Ile
130 135 140

-continued

Thr Lys Thr Glu Thr Ile Thr Ile Leu Val Pro Arg Gln Thr Val Thr
145 150 155 160

Val Arg Pro Arg Thr Arg Lys Val Val Gln Ile Arg Leu Tyr Gln Leu
165 170 175

Arg Ile Pro Arg Val Phe Thr Glu Ile Ser Ala Tyr Val Thr Gly Thr
180 185 190

Leu Arg Gln Pro Ile Pro Gln Ala Asn Pro Asp Val Tyr Ala Thr Leu
195 200 205

Val Ser Val Asn Asn Ala Cys Pro Asn Ala Phe Val Asn Arg Asp Asn
210 215 220

Phe Leu Arg Ile Asp Arg Glu Lys Arg Gly Leu Ala Leu Arg Gly Glu
225 230 235 240

Gly Glu Phe Ser Gly Asn Ile Val Ser Leu Asp Phe Leu Ile Thr Thr
245 250 255

Thr Glu Tyr Asp Leu Asp Thr Asn Ala Ile Ile Asn Ile Asp Asn Thr
260 265 270

Leu Gly Arg Ala Ala Ile Leu Gly Ser Glu Pro Cys Gly Thr Ile Ala
275 280 285

Tyr Thr Glu Pro Ile Asp Ile Ile His Thr Asp Cys
290 295 300

<210> SEQ ID NO 55
<211> LENGTH: 903
<212> TYPE: DNA
<213> ORGANISM: Artificial sequence
<220> FEATURE:
<223> OTHER INFORMATION: Synthetic

<400> SEQUENCE: 55
atgcttgcct tcatcttctc cggcggtagc tcccagctct gcactagcat ccgtaacgag 60
tacaacaaca tcctccaggg cggtggcatg gacgtcagct ccagcttccg cgtggaccct 120
agcaagatca acatcaacga ccttgaggtg acctatcctg agttgaacat tccagataac 180
attatcgcta gtattgtttc caacaacagt ttcgagaaca ggggattcat cactaacgag 240
acttacgcca cggccgaagt aacccgcgct cttactgaga cgattacgac tgccaccacg 300
cgcggattca agtttaccca ggggttcacc tacaccaaca agatcaacct ccgcatccca 360
atcgctggct ctgagtccac catctccttc tctacgtcgt tcgaacagaa catctcgacc 420
actgagacca tcacaaagac cgagactatc accatccttg tgccaaggca gaccgtcacc 480
gtcagacctc ggaccaggaa ggtcgtgcaa atccgtcttt atcagttgcg tattccgagg 540
gtgttcaccg agatttcagc gtatgttact ggcactctcc ggcagccgat ccctcaagca 600
aacccggacg tttacgctac ccttgtttcc gtcaacaatg cctgccccaa tgctttcgtg 660
aaccgagaca acttccttcg catcgaccgg gagaagcgcg gtctcgcgct gcgtggcgag 720
ggcgagttct ctggaaacat cgtctccctg gatttcctga ttactacaac ggagtacgat 780
ctggatacaa acgctatcat caacattgac aacacgctcg ggcgcgcggc catacttggg 840
tcggaaccct gcggtacaat agcatacaca gagcccatcg acatcattca cacagattgt 900
tga 903

<210> SEQ ID NO 56
<211> LENGTH: 300
<212> TYPE: PRT
<213> ORGANISM: Artificial sequence
<220> FEATURE:
<223> OTHER INFORMATION: Synthetic

<400> SEQUENCE: 56

Met Leu Ala Phe Ile Phe Ser Gly Gly Ser Ser Gln Leu Cys Thr Ser
1               5                   10                  15

Ile Arg Asn Glu Tyr Asn Asn Ile Leu Gln Gly Gly Gly Met Asp Val
            20                  25                  30

Ser Ser Ser Phe Arg Val Asp Pro Ser Lys Ile Asn Ile Asn Asp Leu
        35                  40                  45

Glu Val Thr Tyr Pro Glu Leu Asn Ile Pro Asp Asn Ile Ile Ala Ser
    50                  55                  60

Ile Val Ser Asn Asn Ser Phe Glu Asn Arg Gly Phe Ile Thr Asn Glu
65                  70                  75                  80

Thr Tyr Ala Thr Ala Glu Val Thr Arg Ala Leu Thr Glu Thr Ile Thr
                85                  90                  95

Thr Ala Thr Thr Arg Gly Phe Lys Phe Thr Gln Gly Phe Thr Tyr Thr
            100                 105                 110

Asn Lys Ile Asn Leu Arg Ile Pro Ile Ala Gly Ser Glu Ser Thr Ile
        115                 120                 125

Ser Phe Ser Thr Ser Phe Glu Gln Asn Ile Ser Thr Thr Glu Thr Ile
    130                 135                 140

Thr Lys Thr Glu Thr Ile Thr Ile Leu Val Pro Arg Gln Thr Val Thr
145                 150                 155                 160

Val Arg Pro Arg Thr Arg Lys Val Val Gln Ile Arg Leu Tyr Gln Leu
                165                 170                 175

Arg Ile Pro Arg Val Phe Thr Glu Ile Ser Ala Tyr Val Thr Gly Thr
            180                 185                 190

Leu Arg Gln Pro Ile Pro Gln Ala Asn Pro Asp Val Tyr Ala Thr Leu
        195                 200                 205

Val Ser Val Asn Asn Ala Cys Pro Asn Ala Phe Val Asn Arg Asp Asn
    210                 215                 220

Phe Leu Arg Ile Asp Arg Glu Lys Arg Gly Leu Ala Leu Arg Gly Glu
225                 230                 235                 240

Gly Glu Phe Ser Gly Asn Ile Val Ser Leu Asp Phe Leu Ile Thr Thr
                245                 250                 255

Thr Glu Tyr Asp Leu Asp Thr Asn Ala Ile Ile Asn Ile Asp Asn Thr
            260                 265                 270

Leu Gly Arg Ala Ala Ile Leu Gly Ser Glu Pro Cys Gly Thr Ile Ala
        275                 280                 285

Tyr Thr Glu Pro Ile Asp Ile Ile His Thr Asp Cys
    290                 295                 300

<210> SEQ ID NO 57
<211> LENGTH: 597
<212> TYPE: DNA
<213> ORGANISM: Bacillus thuringiensis

<400> SEQUENCE: 57
atgaatacgt atcataaaat atgttctggt ccttatcagt ataatcacaa aggtccctac 60
acggaatgtg ggcctactcc taggagatcc aatcccgatg aagaacattc aactttaaaa 120
gattcatacg gtgatcctgt cctctattac atgccctatt atatggatcc atatgaattt 180
cctggtgaaa gatttgtgta cgaatggact tctgatggag atcgtggagt taaattagga 240
acgtcttatg cgaaagttta tttgcacttt tggaaagcta atggttccga tagtgcttta 300
cgtatcaata tattggatcg tgagggaaac ccagaaaatc agtacttatc taagaaacgt 360

```
ggtactgacg aagtactatt atataatcat gaccctctag aatccgaatg ggttccggag    420

aattcatctg atcctaattt ttcagtagga aactacttct cactccaaaa tgcttcggat    480

catattattt ccaatgaaaa attcttatcc tatagcattc caggtgaatg gttaaccaca    540

gttcagccta ctatgaattc aaaaacaatg tggcgtttaa ttccaacatg gaaataa       597


<210> SEQ ID NO 58
<211> LENGTH: 198
<212> TYPE: PRT
<213> ORGANISM: Bacillus thuringiensis

<400> SEQUENCE: 58

Met Asn Thr Tyr His Lys Ile Cys Ser Gly Pro Tyr Gln Tyr Asn His
1               5                   10                  15

Lys Gly Pro Tyr Thr Glu Cys Gly Pro Thr Pro Arg Arg Ser Asn Pro
            20                  25                  30

Asp Glu Glu His Ser Thr Leu Lys Asp Ser Tyr Gly Asp Pro Val Leu
        35                  40                  45

Tyr Tyr Met Pro Tyr Tyr Met Asp Pro Tyr Glu Phe Pro Gly Glu Arg
    50                  55                  60

Phe Val Tyr Glu Trp Thr Ser Asp Gly Asp Arg Gly Val Lys Leu Gly
65                  70                  75                  80

Thr Ser Tyr Ala Lys Val Tyr Leu His Phe Trp Lys Ala Asn Gly Ser
                85                  90                  95

Asp Ser Ala Leu Arg Ile Asn Ile Leu Asp Arg Glu Gly Asn Pro Glu
            100                 105                 110

Asn Gln Tyr Leu Ser Lys Lys Arg Gly Thr Asp Glu Val Leu Leu Tyr
        115                 120                 125

Asn His Asp Pro Leu Glu Ser Glu Trp Val Pro Glu Asn Ser Ser Asp
    130                 135                 140

Pro Asn Phe Ser Val Gly Asn Tyr Phe Ser Leu Gln Asn Ala Ser Asp
145                 150                 155                 160

His Ile Ile Ser Asn Glu Lys Phe Leu Ser Tyr Ser Ile Pro Gly Glu
                165                 170                 175

Trp Leu Thr Thr Val Gln Pro Thr Met Asn Ser Lys Thr Met Trp Arg
            180                 185                 190

Leu Ile Pro Thr Trp Lys
        195


<210> SEQ ID NO 59
<211> LENGTH: 660
<212> TYPE: DNA
<213> ORGANISM: Bacillus thuringiensis

<400> SEQUENCE: 59

atgaatacgc atcataaaat gtgttctagt ccttatcgat ataatcatag acataaggat     60

tgcgattgtc atttatataa ccataacggt ccttatcagt ataatcacag aggtccctac    120

acggaatgtg gacctactcc taggagatca aatcccgatg aagaacattc aactttaaaa    180

gattcatacg gtgatccagt ccgctatagc atgccctatt atatggatcc atatgaattt    240

cctggtgaaa gatttgtgta cgaatggact tctgatggag atcgtggagt taaattagga    300

acgtcttatg cgagtgttta tttgtacttt tggaaaatta ataatggtac cgatagtgct    360

ttacgtatca atatattgga tcgtgaggga aacccagaaa atcagtactt atctaagaaa    420

cgtggtactg acgaagtact attatataat cgtgaccctc tagaatccga atgggttccg    480
```

gagaattcat ctgatcctaa tttttcagta ggaaactact tctcactcca aagtgcttcg 540
gatcatatta tttccaatga aaaattctta tcctatagca ttcccggtga atggttaacc 600
acagttcagc ctactatgaa ttcaaaaaca atgtggcgtt taattccagc atggaaataa 660

<210> SEQ ID NO 60
<211> LENGTH: 219
<212> TYPE: PRT
<213> ORGANISM: Bacillus thuringiensis

<400> SEQUENCE: 60

Met Asn Thr His His Lys Met Cys Ser Ser Pro Tyr Arg Tyr Asn His
1 5 10 15

Arg His Lys Asp Cys Asp Cys His Leu Tyr Asn His Asn Gly Pro Tyr
20 25 30

Gln Tyr Asn His Arg Gly Pro Tyr Thr Glu Cys Gly Pro Thr Pro Arg
35 40 45

Arg Ser Asn Pro Asp Glu Glu His Ser Thr Leu Lys Asp Ser Tyr Gly
50 55 60

Asp Pro Val Arg Tyr Ser Met Pro Tyr Tyr Met Asp Pro Tyr Glu Phe
65 70 75 80

Pro Gly Glu Arg Phe Val Tyr Glu Trp Thr Ser Asp Gly Asp Arg Gly
85 90 95

Val Lys Leu Gly Thr Ser Tyr Ala Ser Val Tyr Leu Tyr Phe Trp Lys
100 105 110

Ile Asn Asn Gly Thr Asp Ser Ala Leu Arg Ile Asn Ile Leu Asp Arg
115 120 125

Glu Gly Asn Pro Glu Asn Gln Tyr Leu Ser Lys Lys Arg Gly Thr Asp
130 135 140

Glu Val Leu Leu Tyr Asn Arg Asp Pro Leu Glu Ser Glu Trp Val Pro
145 150 155 160

Glu Asn Ser Ser Asp Pro Asn Phe Ser Val Gly Asn Tyr Phe Ser Leu
165 170 175

Gln Ser Ala Ser Asp His Ile Ile Ser Asn Glu Lys Phe Leu Ser Tyr
180 185 190

Ser Ile Pro Gly Glu Trp Leu Thr Thr Val Gln Pro Thr Met Asn Ser
195 200 205

Lys Thr Met Trp Arg Leu Ile Pro Ala Trp Lys
210 215

<210> SEQ ID NO 61
<211> LENGTH: 597
<212> TYPE: DNA
<213> ORGANISM: Artificial sequence
<220> FEATURE:
<223> OTHER INFORMATION: Synthetic

<400> SEQUENCE: 61
atgaacacct accacaagat ttgctccggc ccttaccagt acaaccacaa gggaccgtac 60
actgagtgcg gccctacccc taggcgtagc aaccctgacg aggagcactc cacccttaag 120
gactcctacg gtgacccagt gctctactac atgccgtact acatggaccc atacgagttc 180
cctggcgaaa ggttcgtgta cgagtggacg tcagatggcg atagaggagt caagctcggt 240
actagctatg cgaaagttta cctacacttc tggaaggcta acgggtctga ctccgccttg 300
cggatcaaca ttctcgatag ggagggcaac cctgagaacc agtatctctc caagaagcgc 360

-continued

```
ggcaccgatg aggttcttct gtacaaccac gacccacttg agtccgaatg ggttccagaa    420

aacagctcgg acccgaactt cagcgtggga aactacttca gtctccagaa cgcatcagat    480

cacatcatct cgaatgagaa gtttctctct tattctatcc caggcgagtg gctgactacc    540

gtgcaaccta cgatgaatag taagacaatg tggaggctca ttccgacatg gaagtga       597


<210> SEQ ID NO 62
<211> LENGTH: 198
<212> TYPE: PRT
<213> ORGANISM: Artificial sequence
<220> FEATURE:
<223> OTHER INFORMATION: Synthetic

<400> SEQUENCE: 62

Met Asn Thr Tyr His Lys Ile Cys Ser Gly Pro Tyr Gln Tyr Asn His
1               5                   10                  15

Lys Gly Pro Tyr Thr Glu Cys Gly Pro Thr Pro Arg Arg Ser Asn Pro
            20                  25                  30

Asp Glu Glu His Ser Thr Leu Lys Asp Ser Tyr Gly Asp Pro Val Leu
        35                  40                  45

Tyr Tyr Met Pro Tyr Tyr Met Asp Pro Tyr Glu Phe Pro Gly Glu Arg
    50                  55                  60

Phe Val Tyr Glu Trp Thr Ser Asp Gly Asp Arg Gly Val Lys Leu Gly
65                  70                  75                  80

Thr Ser Tyr Ala Lys Val Tyr Leu His Phe Trp Lys Ala Asn Gly Ser
                85                  90                  95

Asp Ser Ala Leu Arg Ile Asn Ile Leu Asp Arg Glu Gly Asn Pro Glu
            100                 105                 110

Asn Gln Tyr Leu Ser Lys Lys Arg Gly Thr Asp Glu Val Leu Leu Tyr
        115                 120                 125

Asn His Asp Pro Leu Glu Ser Glu Trp Val Pro Glu Asn Ser Ser Asp
    130                 135                 140

Pro Asn Phe Ser Val Gly Asn Tyr Phe Ser Leu Gln Asn Ala Ser Asp
145                 150                 155                 160

His Ile Ile Ser Asn Glu Lys Phe Leu Ser Tyr Ser Ile Pro Gly Glu
                165                 170                 175

Trp Leu Thr Thr Val Gln Pro Thr Met Asn Ser Lys Thr Met Trp Arg
            180                 185                 190

Leu Ile Pro Thr Trp Lys
        195


<210> SEQ ID NO 63
<211> LENGTH: 660
<212> TYPE: DNA
<213> ORGANISM: Artificial sequence
<220> FEATURE:
<223> OTHER INFORMATION: Synthetic

<400> SEQUENCE: 63

atgaacaccc accacaagat gtgctctagc ccttaccgct acaaccaccg ccacaaggac     60

tgcgactgcc acctctacaa ccacaacgga ccctaccagt acaaccatag ggcccccttac   120

actgagtgtg gccctactcc taggcgtagc aacccggacg aggaacacag caccctcaag    180

gactcctacg gcgaccctgt gagatactcc atgccttact acatggaccc ttacgagttc    240

ccaggcgagc gcttcgtgta cgagtggacc tccgacggcg acagaggtgt gaagctcggc    300

acctcctacg cctccgtgta cctctacttc tggaagatca acaatggtac tgattccgct    360
```

-continued

```
cttcggatca acatcctgga tagggagggc aacccggaga accagtatct gagcaagaaa    420

cgcggcactg atgaggtgct gctttacaac cgtgatccgc tggagagcga gtgggtgccg    480

gagaactctt cggaccctaa cttcagtgtt ggaaattact tcagtctcca gtcagcgtca    540

gatcacatca tctctaatga gaagttcctg tcctactcga tcccaggaga atggctcacg    600

acagttcaac ccacgatgaa ctcgaagaca atgtggcgat tgataccagc atggaaatga    660


<210> SEQ ID NO 64
<211> LENGTH: 219
<212> TYPE: PRT
<213> ORGANISM: Artificial sequence
<220> FEATURE:
<223> OTHER INFORMATION: an amino acid sequence translation of SEQ ID
      NO: 63.

<400> SEQUENCE: 64

Met Asn Thr His His Lys Met Cys Ser Ser Pro Tyr Arg Tyr Asn His
1               5                   10                  15

Arg His Lys Asp Cys Asp Cys His Leu Tyr Asn His Asn Gly Pro Tyr
            20                  25                  30

Gln Tyr Asn His Arg Gly Pro Tyr Thr Glu Cys Gly Pro Thr Pro Arg
        35                  40                  45

Arg Ser Asn Pro Asp Glu Glu His Ser Thr Leu Lys Asp Ser Tyr Gly
    50                  55                  60

Asp Pro Val Arg Tyr Ser Met Pro Tyr Tyr Met Asp Pro Tyr Glu Phe
65                  70                  75                  80

Pro Gly Glu Arg Phe Val Tyr Glu Trp Thr Ser Asp Gly Asp Arg Gly
                85                  90                  95

Val Lys Leu Gly Thr Ser Tyr Ala Ser Val Tyr Leu Tyr Phe Trp Lys
            100                 105                 110

Ile Asn Asn Gly Thr Asp Ser Ala Leu Arg Ile Asn Ile Leu Asp Arg
        115                 120                 125

Glu Gly Asn Pro Glu Asn Gln Tyr Leu Ser Lys Lys Arg Gly Thr Asp
    130                 135                 140

Glu Val Leu Leu Tyr Asn Arg Asp Pro Leu Glu Ser Glu Trp Val Pro
145                 150                 155                 160

Glu Asn Ser Ser Asp Pro Asn Phe Ser Val Gly Asn Tyr Phe Ser Leu
                165                 170                 175

Gln Ser Ala Ser Asp His Ile Ile Ser Asn Glu Lys Phe Leu Ser Tyr
            180                 185                 190

Ser Ile Pro Gly Glu Trp Leu Thr Thr Val Gln Pro Thr Met Asn Ser
        195                 200                 205

Lys Thr Met Trp Arg Leu Ile Pro Ala Trp Lys
    210                 215
```